US012692396B2

(12) United States Patent
Yokokura et al.

(10) Patent No.: US 12,692,396 B2
(45) Date of Patent: Jul. 28, 2026

(54) FLUORESCENT LABELING AGENT AND FLUORESCENT DYE

(71) Applicant: artience Co., Ltd., Tokyo (JP)

(72) Inventors: Rino Yokokura, Tokyo (JP); Ryutaro Yamamoto, Tokyo (JP); Hidenori Minashima, Tokyo (JP)

(73) Assignee: artience Co., Ltd., Tokyo (JP)

( * ) Notice: Subject to any disclaimer, the term of this patent is extended or adjusted under 35 U.S.C. 154(b) by 729 days.

(21) Appl. No.: 17/915,474

(22) PCT Filed: Apr. 2, 2021

(86) PCT No.: PCT/JP2021/014351
§ 371 (c)(1),
(2) Date: Sep. 28, 2022

(87) PCT Pub. No.: WO2021/201284
PCT Pub. Date: Oct. 7, 2021

(65) Prior Publication Data

US 2023/0145826 A1 May 11, 2023

(30) Foreign Application Priority Data

Apr. 2, 2020 (JP) ................................ 2020-066924

(51) Int. Cl.
*C09B 47/04* (2006.01)
*C07F 5/06* (2006.01)
*C09K 11/06* (2006.01)
*G01N 21/64* (2006.01)
*G01N 33/58* (2006.01)

(52) U.S. Cl.
CPC .............. *C09B 47/045* (2013.01); *C07F 5/06* (2013.01); *C07F 5/062* (2013.01); *C07F 5/064* (2013.01); *C07F 5/065* (2013.01); *C07F 5/066* (2013.01); *C07F 5/067* (2013.01); *C07F 5/069* (2013.01); *C09K 11/06* (2013.01); *G01N 21/6428* (2013.01); *G01N 33/582* (2013.01); *C09K 2211/1096* (2013.01); *C09K 2211/186* (2013.01); *G01N 2021/6439* (2013.01)

(58) Field of Classification Search
CPC ...................... C09K 2211/186; C09K 2211/18
See application file for complete search history.

(56) References Cited

U.S. PATENT DOCUMENTS 5,135,717 A * 8/1992 Renzoni ............ A61K 41/0071 435/6.12
5,166,197 A * 11/1992 Kenney ................ C09B 47/045 514/183
5,438,135 A 8/1995 Tai et al.
5,627,028 A 5/1997 Tai et al.
6,060,598 A 5/2000 Devlin et al.
2009/0304598 A1 12/2009 Gray
2012/0323164 A1 12/2012 Kenney et al.
2014/0369935 A1 12/2014 Okamoto et al.
2019/0015510 A1 1/2019 Makings et al.
2023/0145826 A1 5/2023 Yokokura et al.
2024/0376378 A1* 11/2024 Yamamoto ............ C09K 11/06

FOREIGN PATENT DOCUMENTS

CN 1583762 A * 2/2005 ................ C07F 7/02
CN 103539799 A * 1/2014 ........... C07D 487/22
CN 103874482 6/2014
CN 109081852 12/2018
JP 02-048991 A * 2/1990 .............. B41M 5/26
JP 05-124354 A * 5/1993 .............. B41M 5/26
JP H05163439 6/1993
JP H05194942 8/1993
(Continued)

OTHER PUBLICATIONS

Eckert et al., Angewandte Chemie (1981), 93(5), pp. 477-479. (Year: 1981).*
A Human assisted English translation of Eckert et al., Angewandte Chemie (1981), 93(5), pp. 477-479. (Year: 1981).*
A Human assisted English translation of JP 02-048991 A (Kashima), 1990. (Year: 1990).*
Chemical Abstracts Registry No. 2306688-28-6, indexed in the Registry file on STN CAS Online May 9, 2019. (Year: 2019).*
A machine generated English translation of Tamano et al. , JP 05-124354 A, 1993. (Year: 1993).*
(Continued)

*Primary Examiner* — Laura L Stockton
(74) *Attorney, Agent, or Firm* — JCIPRNET

(57) ABSTRACT

A fluorescent labeling agent contains a fluorescent dye represented by general formula (1). General formula (1): Q-Z—$R_1$—$R_2$—$R_3$ (In the formula, Q represents the residue of a fluorescent dye. Z represents a direct bond, alkylene group, or arylene group. $R_1$ represents a direct bond, —O—, —OP(=O)$R_4$—, —OC(=O)—, —OS(=O)$_2$—, —OSi$R_5R_6$—, —C(=O)—, or —C(=O)NH—. $R_2$ represents a group selected from the group consisting of alkylene groups, arylene groups, and heterocyclic groups, or represents a group provided by combining these groups. $R_3$ represents —COO$M_1$, —N$R_7R_8$, or —$N^+R_9R_{10}R_{11}$. Here, $R_4$ represents a hydrogen atom, hydroxyl group, alkyl group, aryl group, alkoxy group, aryloxy group, or heterocyclic group. $R_5$ and $R_6$ each independently represent an alkyl group, aryl group, or heterocyclic group. $R_7$-$R_{11}$ each independently represent a hydrogen atom, alkyl group, or aryl group. $M_1$ represents a monovalent cation).

5 Claims, 5 Drawing Sheets

(56) References Cited

FOREIGN PATENT DOCUMENTS

| | | |
|---|---|---|
| JP | H06200177 | 7/1994 |
| JP | 2008209361 | 9/2008 |
| JP | 2009524580 | 7/2009 |
| JP | 2019172826 | 10/2019 |
| JP | 2019218374 | 12/2019 |
| JP | 2020023676 | 2/2020 |
| JP | 2020177014 | 10/2020 |
| JP | 2021193353 | 12/2021 |
| WO | 2004038378 | 5/2004 |
| WO | 2013051732 | 4/2013 |
| WO | 2021201284 | 10/2021 |

OTHER PUBLICATIONS

"Office Action of China Counterpart Application", issued on Mar. 13, 2024, with English translation thereof, p. 1-p. 23.
"Search Report of Europe Counterpart Application", issued on Mar. 26, 2024, p. 1-p. 7.
"Decision of Rejection of China Counterpart Application", issued on Jan. 9, 2025, with English translation thereof, p. 1-p. 15.
"Office Action of China Counterpart Application", issued on Aug. 1, 2024, with English translation thereof, p. 1-p. 14.
"Office Action of Japan Counterpart Application", issued on Aug. 22, 2023, with English translation thereof, p. 1-p. 8.
"Office Action of Japan Counterpart Application", issued on Jan. 30, 2024, with English translation thereof, p. 1-p. 6.
"International Search Report (Form PCT/ISA/210) of PCT/JP2021/014351", mailed on May 11, 2021, with English translation thereof, pp. 1-6.
Yuki Takahashi et al., "In vivo fate of exogenously-administered exosomes," Drug Delivery System, Jun. 2014, pp. 116-124.
"Search Report of Europe Counterpart Application", issued on Sep. 19, 2025, p. 1-p. 8.
"Trial and Appeal Decision of Japan Counterpart Application", issued on Jan. 20, 2026, with English translation thereof, p. 1-p. 59.

* cited by examiner

FLUORESCENT LABELING AGENT AND FLUORESCENT DYE

CROSS-REFERENCE TO RELATED APPLICATION

This application is a 371 application of the international PCT application serial no. PCT/JP2021/014351, filed on Apr. 2, 2021, which claims the priority benefit of Japan application no. 2020-066924, filed on Apr. 2, 2020.

TECHNICAL FIELD

An embodiment of the present invention relates to a fluorescent labeling agent and a fluorescent dye that is used in a fluorescent labeling agent.

BACKGROUND ART

Bioimaging is a technique that visualizes proteins, cells, tissues, and the like in living organisms. Bioimaging is in wide use in the research area of biology and medical science such as clarification of the functions of molecules and cells in living organisms and research of drug discovery.

In particular, a fluorescence bioimaging method is an imaging method capable of dynamic observation, multicolor observation and high-sensitivity observation of phenomena. Recently, the fluorescence bioimaging method also has attracted attention as an imaging method capable of non-invasive diagnosis, and the application of this method in clinical practice such as diagnostic imaging with a small patient burden and real-time diagnosis during operations is expected.

The fluorescence bioimaging method is a method in which a target is visualized using a conjugate-type fluorescent dye that is specifically conjugated to a target substance or an accumulation-type fluorescent dye that is accumulated in a target site. In the method, fluorescence that is emitted when the fluorescent dye is irradiated with ultraviolet to near-infrared light is detected.

In accumulation-type fluorescence bioimaging in which accumulation in a target site is used, the labeling method is simple and rapid compared with that in conjugate-type fluorescence bioimaging in which specific conjugation to a target substance is used. In addition, the accumulation-type fluorescence bioimaging does not require specific conjugation to a target substance and thus has advantages in that no maturation time until the fluorescence intensity stabilizes is needed and the influence on target substances is minimized.

Patent Literature 1 and Patent Literature 2 disclose accumulation-type fluorescent dyes that are accumulated in phospholipids that form cell membranes.

Phospholipids form the surfaces of a variety of living substances such as cells, liposomes, and extracellular vesicles. In recent years, imaging of micro-substances having a phospholipid, such as liposome imaging for drug delivery system (DDS) and exosome imaging described in Patent Literature 1, has been gaining attention. In the case of using the fluorescent dyes described in Patent Literature 1 and Patent Literature 2 in order to perform such in vitro and in vivo imaging, there has been a problem of a low fluorescence intensity.

CITATION LIST

Patent Literature

[Patent Literature 1]
Japanese Patent Laid-Open No. 2009-524580
[Patent Literature 2]
Japanese Patent Laid-Open No. 2008-209361

Non-Patent Literature

[Non-Patent Literature 1]
Drug Delivery System Vol. 29, Issue 2, published Mar. 25, 2014, pp. 116 to 124

SUMMARY OF INVENTION

Technical Problem

In consideration of the above-described circumstances, an embodiment of the present invention provides a fluorescent dye that is excellent in terms of a property of being accumulated in phospholipids, exhibits a high fluorescence intensity, and, in particular, has a fluorescence intensity suitable for fluorescent labeling agents that are used for in vitro and in vivo imaging.

Solution to Problem

As a result of repeating intensive studies in order to solve the above-described problem, the present inventors found an excellent fluorescent dye and completed the present invention. That is, the embodiment of the present invention relates to the following. Here, the present invention is not limited to the following embodiments and includes a variety of embodiments.

One embodiment relates to a fluorescent labeling agent containing a fluorescent dye represented by the following general formula (1).

$$Q\text{-}Z—R_1—R_2—R_3 \qquad \text{General Formula (1):}$$

Here, Q represents a residue of the fluorescent dye.

Z represents a direct bond, a substituted or unsubstituted alkylene group, or a substituted or unsubstituted arylene group.

$R_1$ represents a direct bond, —O—, —OP(=O)$R_4$—, —OC(=O)—, —OS(=O)$_2$—, —OSi$R_5R_6$—, —C(=O)—, or —C(=O)NH—.

$R_2$ represents a group selected from the group consisting of substituted or unsubstituted alkylene groups, substituted or unsubstituted arylene groups, and substituted or unsubstituted heterocyclic groups, or represents a group provided by combining these groups.

$R_3$ represents —COO$M_1$, —N$R_7R_8$, —$N^+R_9R_{10}R_{11}$, —O$M_2$, or —P(=O)(O$M_3$)O$M_4$.

Here, $R_4$ represents a hydrogen atom, a hydroxyl group, a substituted or unsubstituted alkyl group, a substituted or unsubstituted aryl group, a substituted or unsubstituted alkoxy group, a substituted or unsubstituted aryloxy group, or a substituted or unsubstituted heterocyclic group.

$R_5$ and $R_6$ each independently represent a substituted or unsubstituted alkyl group, a substituted or unsubstituted aryl group, or a substituted or unsubstituted heterocyclic group.

$R_7$-$R_{11}$ each independently represent a hydrogen atom, a substituted or unsubstituted alkyl group, or a substituted or unsubstituted aryl group.

$M_1$, $M_2$, $M_3$, and $M_4$ each independently represent a hydrogen atom or a monovalent cation.

In one embodiment, the fluorescent labeling agent is preferably a phospholipid accumulation-type fluorescent labeling agent.

In one embodiment, the fluorescent dye is preferably a phthalocyanine dye represented by the following general formula (2).

General Formula (2)

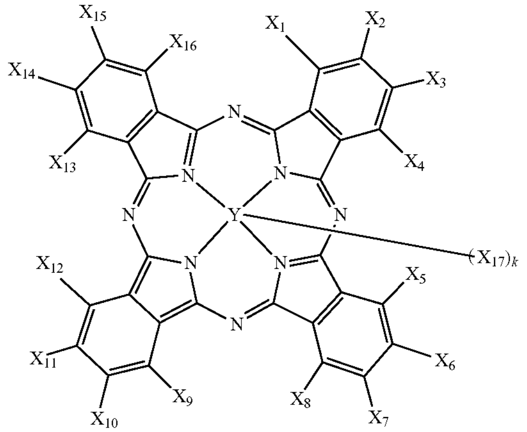

Here, $X_1$-$X_{16}$ each independently represent —Z—$R_1$—$R_2$—$R_3$, a hydrogen atom, a substituted or unsubstituted alkyl group, a substituted or unsubstituted aryl group, a substituted or unsubstituted cycloalkyl group, a substituted or unsubstituted alkenyl group, a substituted or unsubstituted heterocyclic group, -AB, —$SO_3M_5$, or —$COOM_6$.

In the above description, A represents a Group 16 element. B represents a hydrogen atom, a substituted or unsubstituted alkyl group, a substituted or unsubstituted aryl group, a substituted or unsubstituted cycloalkyl group, or a substituted or unsubstituted heterocyclic group. $M_5$ and $M_6$ each independently represent a monovalent cation, in the $X_1$-$X_{16}$, adjacent substituents may be linked to each other to form a ring.

$X_{17}$ represents —Z—$R_1$—$R_2$—$R_3$, a hydroxyl group, a halogen element, a substituted or unsubstituted alkoxy group, a substituted or unsubstituted aryloxy group, —OP(═O)$X_{18}X_{19}$, —OC(═O)$X_2$O, —OS(═O)$_2X_{21}$, or —OSi$X_{22}X_{23}X_{24}$.

Here, $X_{18}$ and $X_{19}$ each independently represent a hydrogen atom, a hydroxyl group, a substituted or unsubstituted alkyl group, a substituted or unsubstituted aryl group, a substituted or unsubstituted alkoxy group, a substituted or unsubstituted aryloxy group, or a substituted or unsubstituted heterocyclic group.

$X_{20}$ represents a hydrogen atom, a substituted or unsubstituted alkyl group, a substituted or unsubstituted aryl group, or a substituted or unsubstituted heterocyclic group.

$X_{21}$ represents a hydroxyl group, a substituted or unsubstituted alkyl group, a substituted or unsubstituted aryl group, or a substituted or unsubstituted heterocyclic group.

$X_{22}$-$X_{24}$ each independently represent a substituted or unsubstituted alkyl group, a substituted or unsubstituted aryl group, or a substituted or unsubstituted heterocyclic group.

Y represents a divalent to pentavalent metal atom, and k is an integer. In a case where Y is a divalent metal atom, k is 0, in a case where Y is a trivalent metal atom, k is 1, and, in a case where Y is a tetravalent or pentavalent metal atom, k is 2.

Here, in the above description, at least one of $X_1$-$X_{17}$ is —Z—$R_1$—$R_2$—$R_3$.

In one embodiment, the fluorescent labeling agent preferably contains a fluorescent dye in which $X_{17}$ in the general formula (2) is —Z—$R_1$—$R_2$—$R_3$.

One embodiment relates to a compound represented by the following general formula (3).

General Formula (3)

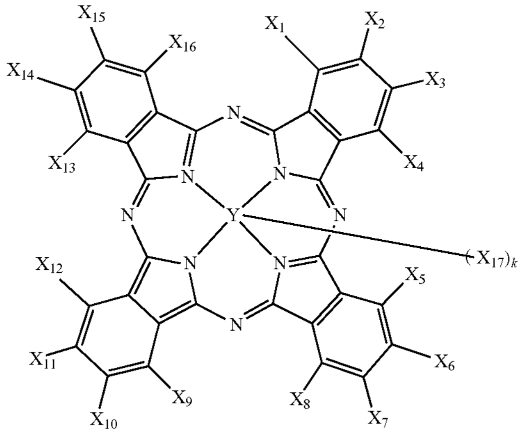

Here, $X_1$-$X_{16}$ each independently represent —Z—$R_1$—$R_2$—$R_3$, a hydrogen atom, a substituted or unsubstituted alkyl group, a substituted or unsubstituted aryl group, a substituted or unsubstituted cycloalkyl group, a substituted or unsubstituted alkenyl group, a substituted or unsubstituted heterocyclic group, -AB, —$SO_3M_5$, or —$COOM_6$.

In the above description, A represents a Group 16 element. B represents a hydrogen atom, a substituted or unsubstituted alkyl group, a substituted or unsubstituted aryl group, a substituted or unsubstituted cycloalkyl group, or a substituted or unsubstituted heterocyclic group. $M_5$ and $M_6$ each independently represent a monovalent cation, in the $X_1$-$X_{16}$, adjacent substituents may be linked to each other to form a ring.

$X_{17}$ represents —Z—$R_1$—$R_2$—$R_3$, a hydroxyl group, a halogen element, a substituted or unsubstituted alkoxy group, a substituted or unsubstituted aryloxy group, —OP(═O)$X_{18}X_{19}$, —OC(═O)$X_2$O, —OS(═O)$_2X_{21}$, or —OSi$X_{22}X_{23}X_{24}$.

Here, $X_{18}$ and $X_{19}$ each independently represent a hydrogen atom, a hydroxyl group, a substituted or unsubstituted alkyl group, a substituted or unsubstituted aryl group, a substituted or unsubstituted alkoxy group, a substituted or unsubstituted aryloxy group, or a substituted or unsubstituted heterocyclic group.

$X_{20}$ represents a hydrogen atom, a substituted or unsubstituted alkyl group, a substituted or unsubstituted aryl group, or a substituted or unsubstituted heterocyclic group.

$X_{21}$ represents a hydroxyl group, a substituted or unsubstituted alkyl group, a substituted or unsubstituted aryl group, or a substituted or unsubstituted heterocyclic group.

$X_{22}$-$X_{24}$ each independently represent a substituted or unsubstituted alkyl group, a substituted or unsubstituted aryl group, or a substituted or unsubstituted heterocyclic group.

Y represents a divalent to pentavalent metal atom, and k is an integer. In a case where Y is a divalent metal atom, k is 0, in a case where Y is a trivalent metal atom, k is 1, and, in a case where Y is a tetravalent or pentavalent metal atom, k is 2.

Here, in the above description, at least one of $X_1$-$X_{17}$ is —Z—$R_1$—$R_2$—$R_3$ and is as described below.

Z represents a direct bond, a substituted or unsubstituted alkylene group, or a substituted or unsubstituted arylene group.

$R_1$ represents a direct bond, —O—, —OP(=O)$R_4$—, —OC(=O)—, —OS(=O)$_2$—, —OSi$R_5R_6$—, —C(=O)—, or —C(=O)NH—.

$R_2$ represents a group selected from the group consisting of substituted or unsubstituted alkylene groups, substituted or unsubstituted arylene groups, and substituted or unsubstituted heterocyclic groups, or represents a group provided by combining these groups.

$R_3$ represents —COO$M_1$, —N$R_7R_8$, —$N^+R_9R_{10}R_{11}$, —O$M_2$, or —P(=O)(O$M_3$)O$M_4$.

Here, $R_4$ represents a hydrogen atom, a hydroxyl group, a substituted or unsubstituted alkyl group, a substituted or unsubstituted aryl group, a substituted or unsubstituted alkoxy group, a substituted or unsubstituted aryloxy group, or a substituted or unsubstituted heterocyclic group. $R_5$ and $R_6$ each independently represent a substituted or unsubstituted alkyl group, a substituted or unsubstituted aryl group, or a substituted or unsubstituted heterocyclic group. $R_7$-$R_{11}$ each independently represent a hydrogen atom, a substituted or unsubstituted alkyl group, or a substituted or unsubstituted aryl group. $M_1$, $M_2$, $M_3$, and $M_4$ each independently represent a hydrogen atom or a monovalent cation.

The disclosure of the present application is associated with the topic described in Japanese Patent Application No. 2020-066924, filed Apr. 2, 2020, and the entire disclosed content thereof is incorporated herein by reference.

Advantageous Effects of Invention

According to the embodiments of the present invention, it becomes possible to provide a fluorescent dye having a fluorescence intensity suitable for fluorescent labeling agents that are used for in vitro and in vivo imaging by the introduction of a functional group having an excellent property of being accumulated in phospholipids.

DESCRIPTION OF EMBODIMENTS

Figure 1:
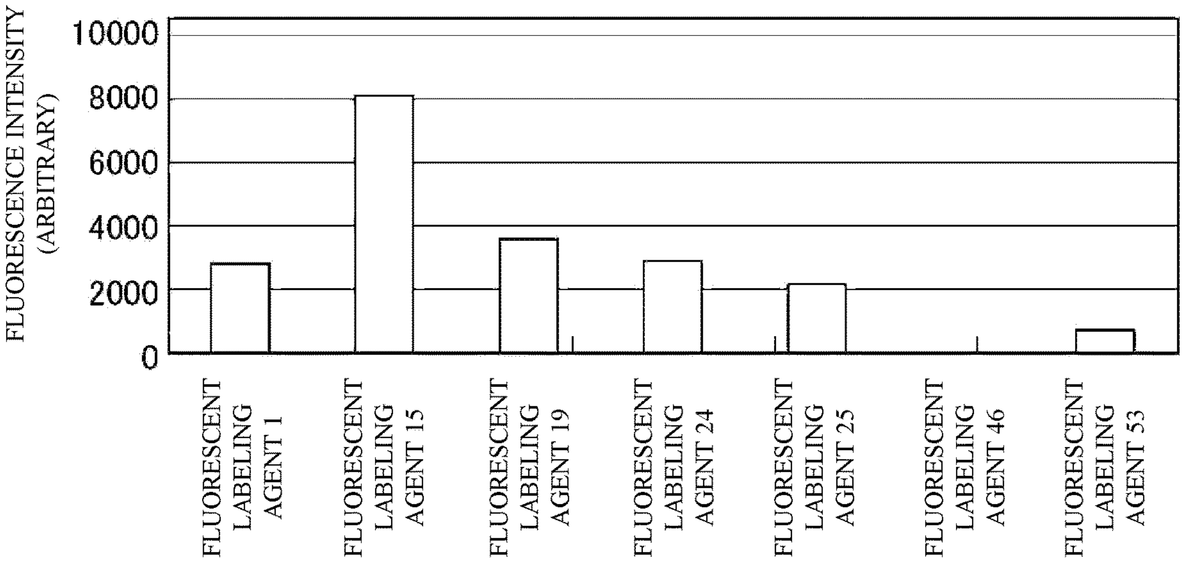
FIG. 1 is a graph showing the evaluation results of the fluorescence intensities of fluorescent labeling agents 1, 15, 19, 24, 25, 68, and 75.
Figure 2:
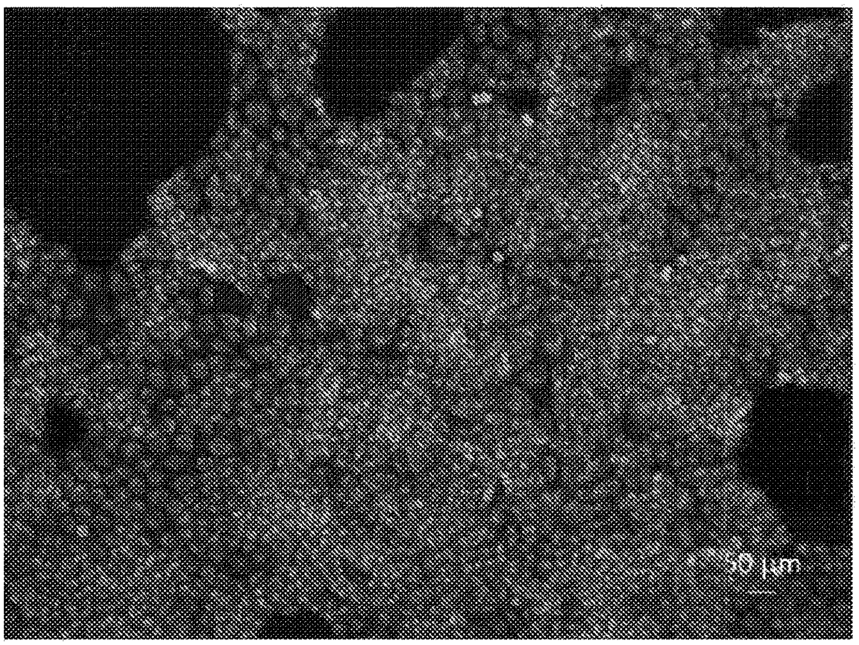
FIG. 2 is a fluorescence micrograph of a cell labeled with the fluorescent labeling agent 1.
Figure 3:
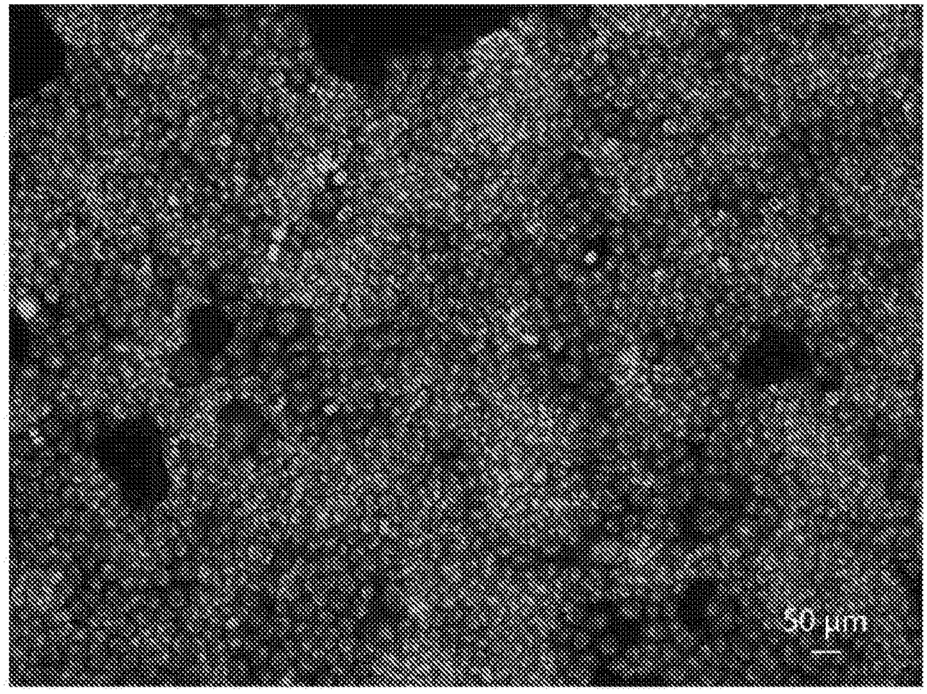
FIG. 3 is a fluorescence micrograph of a cell labeled with the fluorescent labeling agent 15.
Figure 4:
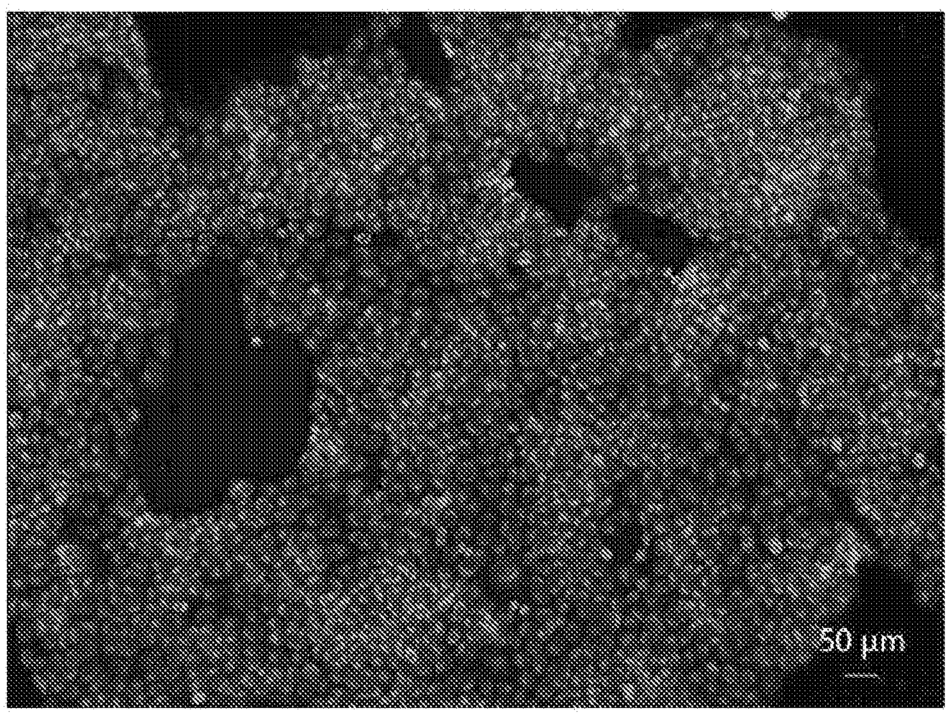
FIG. 4 is a fluorescence micrograph of a cell labeled with the fluorescent labeling agent 19.
Figure 5:
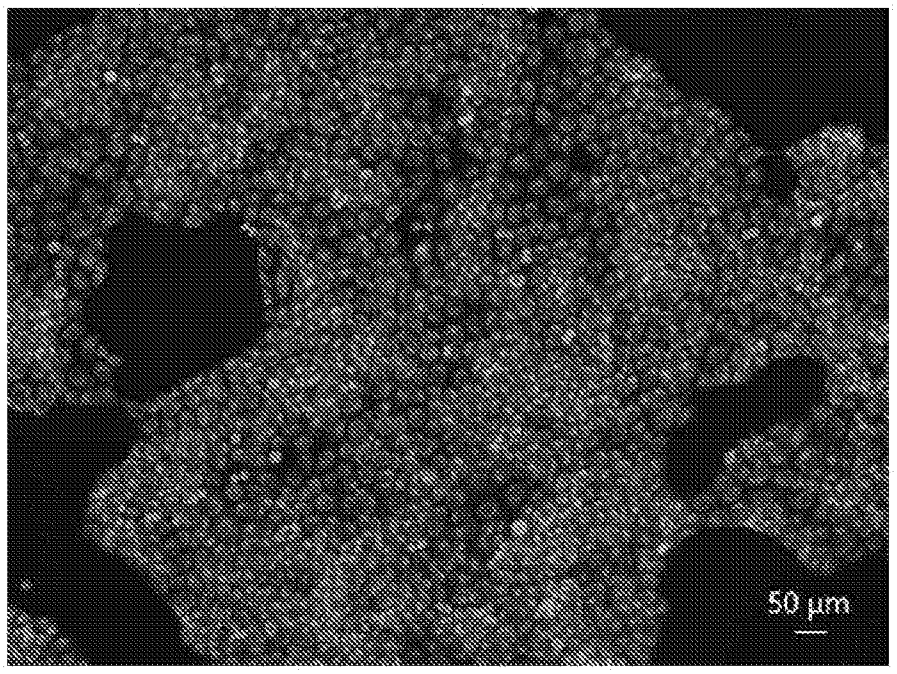
FIG. 5 is a fluorescence micrograph of a cell labeled with the fluorescent labeling agent 24.
Figure 6:
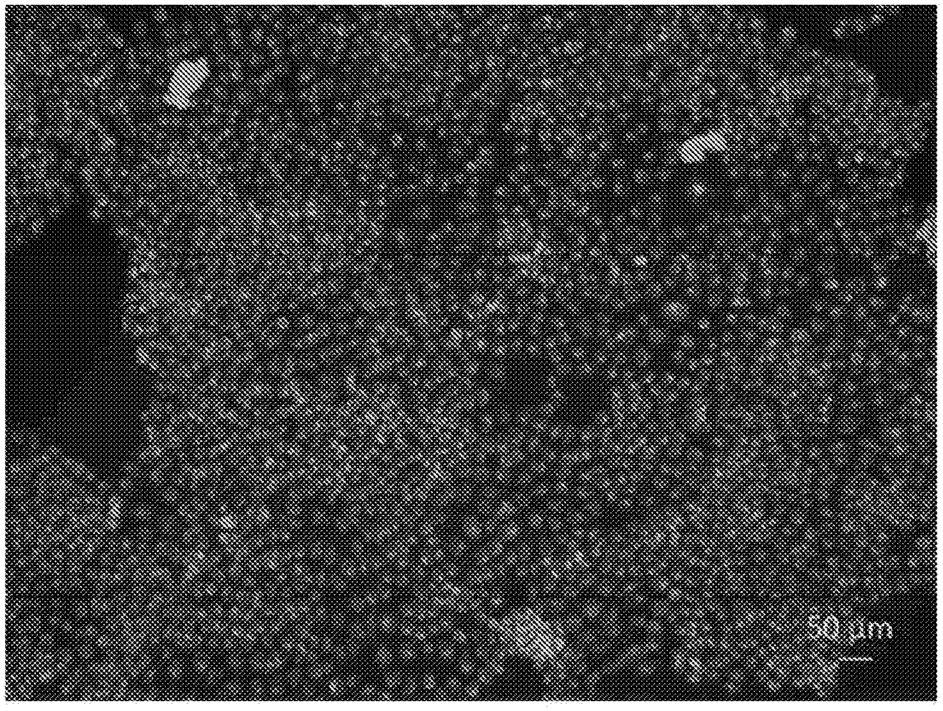
FIG. 6 is a fluorescence micrograph of a cell labeled with the fluorescent labeling agent 25.

Hereinafter, an embodiment of the present invention will be described in detail. Here, the embodiment of the present invention is not limited to the following description and includes a variety of embodiments.

A fluorescent labeling agent, which is one embodiment of the present invention, contains a fluorescent dye represented by the following general formula (1). The compound represented by the following general formula (1) is a fluorescent dye.

Q-Z—$R_1$—$R_2$—$R_3$ General Formula (1):

Here, Q represents a residue of the fluorescent dye. In the present specification, the fluorescent dye is a dye that emits fluorescence when irradiated with ultraviolet to near-infrared light (for example, light with a wavelength of 560 to 900 nm) and may be a well-known compound. The fluorescent dye is not particularly limited, and examples thereof include dyes of fluoresceins, rhodamines, coumarins, cyanines, phthalocyanines, diketopyrrolopyrroles, boron-dipyrromethenes (BODIPY), xanthenes, pyrenes, merocyanines, perylenes, acridines, stilbenes, pyrromethenes, unbelliferones, and the like.

In one embodiment, the compound represented by the general formula (1) (fluorescent dye) may have, for example, the skeleton of a dye exemplified above as the residue Q of the fluorescent dye. That is, the compound represented by the general formula (1) may be compound having a structure in which at least one substituent (functional group) represented by —Z—$R_1$—$R_2$—$R_3$ has been introduced into the skeleton of the dye exemplified above.

In one embodiment, the fluorescent dye is preferably phthalocyanines from the viewpoint of stability and fluorescence wavelength. In one embodiment, a compound represented by the following general formula (2) (phthalocyanine dye) can be preferably used as the fluorescent dye. Here, a premise is that at least one of $X_1$-$X_{17}$ is a substituent represented by —Z—$R_1$—$R_2$—$R_3$.

In a case where the fluorescent dye that configures the fluorescent labeling agent contains the compound represented by the following general formula (2), it is possible to easily obtain a fluorescent labeling agent having excellent durability from the skeleton of the phthalocyanine dye. In addition, it is possible to easily obtain luminance at wavelengths suitable for in vitro and in vivo bioimaging (for example, 650 to 900 nm) from the skeleton of the phthalocyanine dye.

General Formula (2)

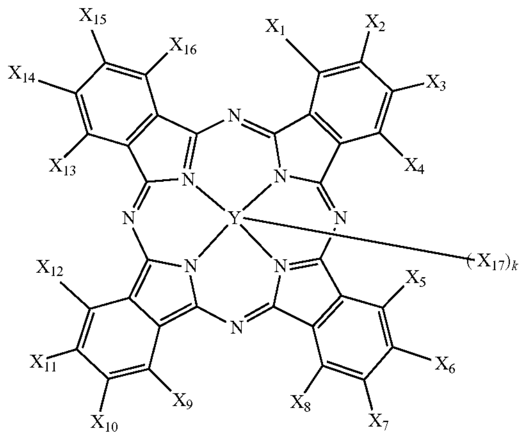

In the fluorescent dye of the embodiment, "—Z—$R_1$—$R_2$—$R_3$" is a substituent having a hydrophilic group and is capable of enhancing the property of the fluorescent dye being accumulated in phospholipids through the electrostatic interaction with a hydrophilic group in a phospholipid. The specific configuration of the substituent is as described below.

Z represents a direct bond, a substituted or unsubstituted alkylene group, or a substituted or unsubstituted arylene group. In one embodiment, Z is preferably a direct bond.

$R_1$ represents a direct bond, —O—, —OP(=O)$R_4$—, —OC(=O)—, —OS(=O)$_2$—, —OSi$R_5R_6$—, —C(=O)—, or —C(=O)NH—. In one embodiment, $R_1$ is preferably —OP(=O)$R_4$—, —OS(=O)$_2$—, or —OSi$R_5R_6$—.

$R_2$ represents a group selected from the group consisting of substituted or unsubstituted alkylene groups, substituted or unsubstituted arylene groups, and substituted or unsubstituted heterocyclic groups, or represents a group provided by combining these groups. In one embodiment, $R_2$ is preferably a substituted or unsubstituted alkylene group or a substituted or unsubstituted arylene group, and more preferably a substituted or unsubstituted alkylene group. In one embodiment, $R_2$ is preferably an alkylene group. The number of carbon atoms in the main chain of the alkylene group is preferably 1 to 10.

$R_3$ represents —COO$M_1$, —N$R_7R_8$, or —$N^+R_9R_{10}R_{11}$. In addition, $R_3$ represents —O$M_2$, or —P(=O)(O$M_3$)$_4$. In one embodiment, $R_3$ is preferably —COO$M_1$, —N$R_7R_8$, —O$M_2$, or —P(=O)(O$M_3$)O$M_4$.

Here, $R_4$ represents a hydrogen atom, a hydroxyl group, a substituted or unsubstituted alkyl group, a substituted or unsubstituted aryl group, a substituted or unsubstituted alkoxy group, a substituted or unsubstituted aryloxy group, or a substituted or unsubstituted heterocyclic group. In one embodiment, $R_4$ is preferably a hydrogen atom, a hydroxyl group, a substituted or unsubstituted alkyl group, or a substituted or unsubstituted aryl group.

$R_5$ and $R_6$ each independently represent a substituted or unsubstituted alkyl group, a substituted or unsubstituted aryl group, or a substituted or unsubstituted heterocyclic group. In one embodiment, $R_5$ and $R_6$ are each independently preferably a substituted or unsubstituted alkyl group or a substituted or unsubstituted aryl group. The alkyl group is more preferably a linear or branched alkyl group having 1 to 5 carbon atoms.

$R_7$-$R_{11}$ each independently represent a hydrogen atom, a substituted or unsubstituted alkyl group, or a substituted or unsubstituted aryl group. In one embodiment, $R_7$-$R_{11}$ are each independently preferably a hydrogen atom or a substituted or unsubstituted alkyl group. The alkyl group is more preferably a linear or branched alkyl group having 1 to 5 carbon atoms.

$M_1$, $M_2$, $M_3$, and $M_4$ each independently represent a hydrogen atom or a monovalent cation. Examples of the monovalent cation include alkali metals, quaternary amines, and the like. Examples of the alkali metals include lithium, sodium, potassium, rubidium, cesium, and the like. In one embodiment, $M_1$, $M_2$, $M_3$, and $M_4$ are each preferably a hydrogen atom.

$X_1$-$X_{16}$ each independently represent a hydrogen atom or a substituent selected from the group consisting of —Z—$R_1$—$R_2$—$R_3$, substituted or unsubstituted alkyl groups, substituted or unsubstituted aryl groups, substituted or unsubstituted cycloalkyl groups, substituted or unsubstituted alkenyl groups, substituted or unsubstituted heterocyclic groups, -AB, —$SO_3M_5$, and —COO$M_6$.

In the above description, $M_5$ and $M_6$ each independently represent a monovalent cation. Examples of the monovalent cation include alkali metals, quaternary amines, and the like. Examples of the alkali metals include lithium, sodium, potassium, rubidium, cesium, and the like.

In one embodiment, at least one, preferably four or more, of $X_1$-$X_{16}$ is preferably the above-described substituent. In one embodiment, the above-described substituents with respect to the dye skeleton are each independently preferably a substituted or unsubstituted alkyl group, a substituted or unsubstituted aryl group, or -AB.

In the above-described -AB, A represents a Group 16 element. Examples of the Group 16 element include oxygen, sulfur, selenium, tellurium, and the like. In one embodiment, A is preferably oxygen, sulfur, or selenium. From the viewpoint of easy synthesis and stability, oxygen or sulfur is more preferable. From the viewpoint of the fluorescence intensity, oxygen is still more preferable. B represents a hydrogen atom, a substituted or unsubstituted alkyl group, a substituted or unsubstituted aryl group, a substituted or unsubstituted cycloalkyl group, or a substituted or unsubstituted heterocyclic group, each of which is as described above. In one embodiment, B is preferably a hydrogen atom, a substituted or unsubstituted alkyl group, or a substituted or unsubstituted aryl group. Therefore, in one embodiment, -AB is preferably —OR, —OAr, —SR, or —SAr. Here, R represents an alkyl group, and Ar represents an aryl group.

Y represents a divalent to pentavalent metal atom, and k is an integer. In a case where Y is a divalent metal atom, k is 0, in a case where Y is a trivalent metal atom, k is 1, and, in a case where Y is a tetravalent or pentavalent metal atom, k is 2. Examples of the divalent metal atom include Mg, Cu, Zn, and the like. Examples of the trivalent metal atom include Al, Ga, In, and the like. Examples of the tetravalent metal atom include Si, Mn, Sn, Cr, Zr, and the like. Examples of the pentavalent metal atom include P and the like. From the viewpoint of the fluorescence intensity, Y is preferably Al, Si, or P and more preferably Al. From the viewpoint of light resistance, Y is preferably Al or Si.

In one embodiment, in $X_1$-$X_{16}$, adjacent substituents may be linked to each other to form a ring. The structure of the ring may be any of a cycloalkyl, a cycloalkenyl, an aryl, and a heteroaryl and forms a condensed ring with an aromatic ring in a phthalocyanine skeleton. Furthermore, the structure of the ring may be substituted or may not be substituted. The number of carbon atoms that form the structure of the ring may be 2 to 30 and is preferably in a range of 4 to 6. The ring is preferably a five-membered ring or a six-membered ring.

In one embodiment, adjacent substituents are preferably linked to each other to form a phenylene group. In this case, the phenylene group bonds to an aromatic ring in the phthalocyanine skeleton, whereby a naphthalene structure is formed. In a different embodiment, adjacent substituents may be linked to each other to form a ring having a nitrogen atom. In this case, the ring having a nitrogen atom bonds to an aromatic ring in the phthalocyanine skeleton, whereby, for example, an imidazole structure is formed. The ring structure such as the above-described naphthalene structure or imidazole structure may further have a substituent such as an alkyl group or an aryl group.

$X_{17}$ represents —Z—$R_1$—$R_2$—$R_3$, a hydroxyl group, a halogen element, a substituted or unsubstituted alkoxy group, a substituted or unsubstituted aryloxy group, —OP(═O)$X_{18}X_{19}$, —OC(═O)$X_2$O, —OS(═O)$_2X_{21}$, or —OSi$X_{22}X_{23}X_{24}$. In one embodiment, $X_{17}$ is preferably —Z—$R_1$—$R_2$—$R_3$ or a hydroxyl group. Z, $R_1$, $R_2$, and $R_3$ are as described above.

Here, $X_{18}$ and $X_{19}$ each independently represent a hydrogen atom, a hydroxyl group, a substituted or unsubstituted alkyl group, a substituted or unsubstituted aryl group, a substituted or unsubstituted alkoxy group, a substituted or unsubstituted aryloxy group, or a substituted or unsubstituted heterocyclic group.

$X_{20}$ represents a hydrogen atom, a substituted or unsubstituted alkyl group, a substituted or unsubstituted aryl group, or a substituted or unsubstituted heterocyclic group.

$X_{21}$ represents a hydroxyl group, a substituted or unsubstituted alkyl group, a substituted or unsubstituted aryl group, or a substituted or unsubstituted heterocyclic group.

$X_{22}$-$X_{24}$ each independently represent a substituted or unsubstituted alkyl group, a substituted or unsubstituted aryl group, or a substituted or unsubstituted heterocyclic group.

Here, the alkyl groups as the $R_4$-$R_{11}$ and $X_1$-$X_{24}$ are each independently selected. The alkyl groups may be substituted or may not be substituted.

Examples of the alkyl groups include linear or branched alkyl groups. Specific examples thereof include a methyl group, an ethyl group, a propyl group, a butyl group, a pentyl group, a hexyl group, a heptyl group, an octyl group, a nonyl group, a decyl group, a dodecyl group, an octadecyl group, an isopropyl group, an isobutyl group, an isopentyl group, a 2-ethylhexyl group, a sec-butyl group, a tert-butyl group, a sec-pentyl group, a tert-pentyl group, a tert-octyl group, a neopentyl group, and the like. The number of carbon atoms in the alkyl group is preferably in a range of 1 to 30. The number of carbon atoms is more preferably in a range of 1 to 20 and still more preferably in a range of 1 to 10.

Examples of the substituent in the alkyl group include, in addition to a halogen atom such as fluorine, chlorine, or bromine, a hydroxyl group, an amino group, a nitro group, a formyl group, a cyano group, and a carboxyl group, the above-described alkyl groups, an aryl group to be described below, a cycloalkyl group, and a heterocyclic group. In addition, in a case where a part of the structure is substituted by an amide bond (—NHCO—), an ester bond (—COO—), an ether bond (—O—), a urea bond (—NHCONH—), or a urethane bond (—NHCOO—), the substituted part is also regarded as "substituent".

Therefore, the substituted alkyl group means an alkyl group having the above-described substituent. The substituted alkyl groups may be alkyl groups having one or more substituents. For example, specific examples of the alkyl groups having a halogen atom as a substituent include a trifluoromethyl group, a 2,2,2-trifluoroethyl group, —$(CF_2)_4CF_3$, —$(CF_2)_5CF_3$, —$(CF_2)_6CF_3$, —$(CF_2)_7CF_3$, —$(CF_2)_8CF_3$, a trichloromethyl group, a 2,2-dibromoethyl group, and the like.

Specific examples of the alkyl groups having an amide bond as a substituent include —$CH_2$—$CH_2$—$CH_2$—NHCO—$CH_2$—$CH_3$, —$CH_2$—CH(—$CH_3$)—$CH_2$—COO—$CH_2$—$CH_3$, —$CH_2$—$CH_2$—$CH_2$—OCO—$CH_2$—$CH_3$, —$CH_2$—$CH_2$—$CH_2$—$CH_2$—NHCO—$CH_2$—CH($CH_2$—$CH_3$)—$CH_2$—$CH_2$—$CH_2$—$CH_3$, —$(CH_2)_5$-NHCO—$(CH_2)_{11}$—$CH_3$, —$CH_2$—$CH_2$—$CH_2$—C(—NHCO—$CH_2$—$CH_3$)$_3$, and the like. The number of carbon atoms in the alkyl group having an amide bond as a substituent is preferably in a range of 2 to 30. The number of carbon atoms is more preferably in a range of 2 to 10 and still more preferably in a range of 2 to 5.

Specific examples of the alkyl groups having an ester bond as a substituent include —$CH_2$—$CH_2$—$CH_2$—COO—$CH_2$—$CH_3$, —$CH_2$—CH(—$CH_3$)—$CH_2$—NHCO—$CH_2$—$CH_3$, —$CH_2$—$CH_2$—$CH_2$—COO—$CH_2$—$CH_3$, —$CH_2$—$CH_2$—$CH_2$—$CH_2$—COO—$CH_2$—CH($CH_2$—$CH_3$)—$CH_2$—$CH_2$—$CH_2$—$CH_3$, —$(CH_2)_5$-COO—$(CH_2)_{11}$—$CH_3$, —$CH_2$—$CH_2$—$CH_2$—CH—(COO—$CH_2$—$CH_3$)$_2$, and the like. The number of carbon atoms in the alkyl group having an ester bond as a substituent is preferably in a range of 2 to 30. The number of carbon atoms is more preferably in a range of 2 to 10 and still more preferably in a range of 2 to 5.

Specific examples of the alkyl groups having an ether bond as a substituent include —$CH_2$—O—$CH_3$, —$CH_2$—$CH_2$—O—$CH_2$—$CH_3$, —$CH_2$—$CH_2$—$CH_2$—O—$CH_2$—$CH_3$, —($CH_2$—$CH_2$—O)$_n$—$CH_3$ (here, n is an integer of 1 to 8), —($CH_2$—$CH_2$—$CH_2$—O)$_m$—$CH_3$ (here, m is an integer of 1 to 5), —$CH_2$—CH($CH_3$)—O—$CH_2$—$CH_3$, —$CH_2$—CH—($OCH_3$)$_2$, and the like, but are not limited thereto. The number of carbon atoms in the alkyl group having an ether bond as a substituent is preferably in a range of 2 to 30. The number of carbon atoms is more preferably in a range of 2 to 10 and still more preferably in a range of 2 to 5.

Specific examples of the alkyl groups having a urea bond (—NHCONH—) as a substituent include —$CH_2$—NHCONH—$CH_3$, —$CH_2$—$CH_2$—NHCONH—$CH_2$—$CH_3$, —$CH_2$—$CH_2$—$CH_2$—NHCONH—$CH_2$—$CH_3$, —($CH_2$—$CH_2$—NHCONH)$_n$—$CH_3$ (here, n is an integer of 1 to 8), —($CH_2$—$CH_2$—$CH_2$—NHCONH)$_m$—$CH_3$ (here, m is an integer of 1 to 5), —$CH_2$—CH($CH_3$)—NHCONH—$CH_2$—$CH_3$, —$CH_2$—CH—($NHCONHCH_3$)$_2$, and the like, but are not limited thereto. The number of carbon atoms in the alkyl group having a urea bond as a substituent is preferably in a range of 2 to 30. The number of carbon atoms is more preferably in a range of 2 to 10 and still more preferably in a range of 2 to 5.

Specific examples of the alkyl groups having a urethane bond as a substituent include —$CH_2$—$CH_2$—$CH_2$—NHCOO—$CH_2$—$CH_3$, —$CH_2$—CH(—$CH_3$)—$CH_2$—NHCOO—$CH_2$—$CH_3$, —$CH_2$—$CH_2$—$CH_2$—NHCOO—$CH_2$—$CH_3$, —$CH_2$—$CH_2$—$CH_2$—$CH_2$—NHCOO—$CH_2$—CH($CH_2$—$CH_3$)—$CH_2$—$CH_2$—$CH_2$—$CH_3$, $—(CH_2)_5—NHCOO—(CH_2)_{11}\text{-}CH_3$, $—CH_2—CH_2—CH_2—CH—(NHCOO—CH_2—CH_3)_2$, and the like. The number of carbon atoms in the alkyl group having a urethane bond as a substituent is preferably in a range of 2 to 30. The number of carbon atoms is more preferably in a range of 2 to 10 and still more preferably in a range of 2 to 5.

Specific examples of the alkyl groups having two or more of the amide bond (—NHCO—), the ester bond (—COO—), the ether bond (—O—), the urea bond (—NHCONH—), and the urethane bond (—NHCOO—) as substituents include $—CH_2—CH_2—NHCO—CH_2—CH_2—O—CH_2—CH(CH_2—CH_3)—CH_2—CH_2—CH_2—CH_3$, $—CH_2—CH_2—COO—CH_2—CH_2—O—CH_2—CH_2—NHCOO—CH_2—CH(CH_2—CH_3)—CH_2—CH_2—CH_2—CH_3$, $—CH_2—CH_2—NHCO—CH_2(OCO—CH_2)—CH_2—$. The number of carbon atoms in the alkyl group having two or more of the amide bond (—NHCO—), the ester bond (—COO—), the ether bond (—O—), the urea bond (—NHCONH—), and the urethane bond (—NHCOO—) as substituents is preferably in a range of 3 to 30. The number of carbon atoms is more preferably in a range of 3 to 10 and still more preferably in a range of 3 to 5.

The aryl groups as the $R_4$-$R_{11}$ and $X_1$-$X_{24}$ are each independently selected. The aryl groups may be substituted or may not be substituted.

Examples of the aryl groups include monocyclic or condensed polycyclic aryl groups. Examples thereof include a phenyl group, a 1-naphthyl group, a 2-naphthyl group, a p-biphenyl group, a m-biphenyl group, a 2-anthryl group, a 9-anthryl group, a 2-phenanthryl group, a 3-phenanthryl group, a 9-phenanthryl group, a 2-fluorenyl group, a 3-fluorenyl group, a 9-fluorenyl group, a 1-pyrenyl group, a 2-pyrenyl group, a 3-perylenyl group, an o-tolyl group, a m-tolyl group, a p-tolyl group, a 4-methylbiphenyl group, a terphenyl group, a 4-methyl-1-naphthyl group, a 4-tert-butyl-1-naphthyl group, a 4-naphthyl-1-naphthyl group, a 6-phenyl-2-naphthyl group, a 10-phenyl-9-anthryl group, a spirofluorenyl group, a 2-benzocyclobutenyl group, and the like. The number of carbon atoms in the aryl group is preferably in a range of 6 to 18. The number of carbon atoms is more preferably in a range of 6 to 10.

The substituent in the substituted aryl group may be the same as the substituent exemplified as the substituent in the alkyl group.

The cycloalkyl groups as $X_1$-$X_{16}$ are each independently selected. The cycloalkyl groups may be substituted or may not be substituted. Examples of the cycloalkyl groups include a cyclopentyl group, a cyclohexyl group, a 2,5-dimethylcyclopentyl group, a 4-tert-butylcyclohexyl group, and the like. In addition, the number of carbon atoms in the cycloalkyl group is preferably in a range of 3 to 12. The number of carbon atoms is more preferably in a range of 3 to 6. The substituent in the substituted cycloalkyl group may be the same as the substituent exemplified as the substituent in the alkyl group.

The alkenyl groups as $X_1$-$X_{16}$ are each independently selected. The alkenyl groups may be substituted or may not be substituted. Examples of the alkenyl groups include linear or branched alkenyl groups. The alkenyl group generally refers to a group having one double bonds in the structure; however, in the present specification, the alkenyl group may have a plurality of double bonds in the structure. Specific examples of the alkenyl groups include a vinyl group, a 1-propenyl group, an allyl group, a 2-butenyl group, a 3-butenyl group, an isopropenyl group, an isobutenyl group, a 1-pentenyl group, a 2-pentenyl group, a 3-pentenyl group, a 4-pentenyl group, a 1-hexenyl group, a 2-hexenyl group, a 3-hexenyl group, a 4-hexenyl group, a 1,3-butadienyl group, and the like. The number of carbon atoms in the alkenyl group is preferably in a range of 2 to 18. The number of carbon atoms is more preferably 2 to 10 and still more preferably 2 to 5. The substituent in the substituted alkenyl group may be the same as the substituent exemplified as the substituent in the alkyl group.

The heterocyclic groups as the $R_2$, $R_4$-$R_{11}$ and $X_1$-$X_{24}$ are each independently selected. The heterocyclic groups may be substituted or may not be substituted.

Examples of the heterocyclic groups include aliphatic heterocyclic groups or aromatic heterocyclic groups. Specific examples thereof include a pyridyl group, a pyrazyl group, a piperidino group, a pyranyl group, a morpholino group, an acridinyl group, and the like. In addition, specific examples thereof also include groups represented by the following structural formula. The number of carbon atoms of the heterocyclic group (the number of carbon atoms that configure the ring) is preferably 4 to 12. The number of ring members is preferably 5 to 13.

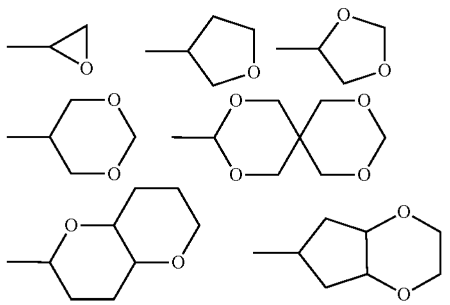

The substituent in the substituted heterocyclic group may be the same as the substituent exemplified as the substituent in the alkyl group. Examples of the substituted heterocyclic group include a 3-methylpyridyl group, a N-methylpiperidyl group, a N-methylpyrrolyl group, and the like.

The alkoxy groups as the $R_4$, $X_{18}$, and $X_{19}$ are each independently selected. The alkoxy groups may be substituted or may not be substituted.

Examples of the alkoxy groups include linear or branched alkoxyl groups. Specific examples thereof include a methoxy group, an ethoxy group, a propoxy group, an isopropoxy group, an n-butoxy group, an isobutoxy group, a tert-butoxy group, a neopentyloxy group, a 2,3-dimethyl-3-pentyloxy group, an n-hexyloxy group, an n-octyloxy group, a stearyloxy group, a 2-ethylhexyloxy group, and the like. The number of carbon atoms in the alkoxyl group is preferably in a range of 1 to 6.

The substituent in the substituted alkoxyl group may be the same as the substituent exemplified as the substituent in the alkyl group.

The substituent in the substituted alkoxy group may be the same as the substituent exemplified as the substituent in the alkyl group. Specific examples of the substituted alkoxy group include a trichloromethoxy group, a trifluoromethoxy group, a 2,2,2-trifluoroethoxy group, a 2,2,3,3-tetrafluoropropoxy group, a 2,2-bis(trifluoromethyl)propoxy group, a 2-ethoxyethoxy group, a 2-butoxyethoxy group, a 2-nitropropoxy group, a benzyloxy group, and the like.

The aryloxy groups as the $R_4$, $X_{18}$, and $X_{19}$ are each independently selected. The aryloxy groups may be substituted or may not be substituted.

Examples of the aryloxy groups include monocyclic or condensed polycyclic aryloxy groups. Specific examples thereof include a phenoxy group, a p-methylphenoxy group, a naphthyloxy group, an anthryloxy group, and the like. The aryloxy group is preferably a monocyclic aryloxy group. In addition, an aryloxy group having 6 to 12 carbon atoms is preferable.

The substituent in the substituted aryloxy group may be the same as the substituent exemplified as the substituent in the aryl group. Examples of the substituent aryloxy group include a p-nitrophenoxy group, a p-methoxyphenoxy group, a 2,4-dichlorophenoxy group, a pentafluorophenoxy group, a 2-methyl-4-chlorophenoxy group, and the like.

The alkylene groups as the Z and $R_2$ are each independently selected. The alkylene groups may be substituted or may not be substituted. Examples of the alkylene groups include divalent groups obtained by removing one hydrogen atom from the above-described alkyl group. Specific examples of the substituted or unsubstituted alkylene group include $—CH_2—CH_2—$, $—CH_2—CH_2—CH_2—NHCO—CH_2—CH_2—$, $—CH_2—CH_2—CH_2—OCO—CH_2—CH_2—$, $—CH_2—CH_2—CH_2—O—CH_2—CH_2—$, and the like.

The arylene groups as the Z and $R_2$ are each independently selected. The arylene groups may be substituted or may not be substituted. Examples of the arylene groups include divalent groups obtained by removing one hydrogen atom from the above-described aryl group. The number of carbon atoms in the arylene group is preferably in a range of 6 to 10. In one embodiment, the arylene groups may be a phenylene group or a naphthylene group. Specific examples of the substituted or unsubstituted arylene groups include groups represented by the following structural formula.

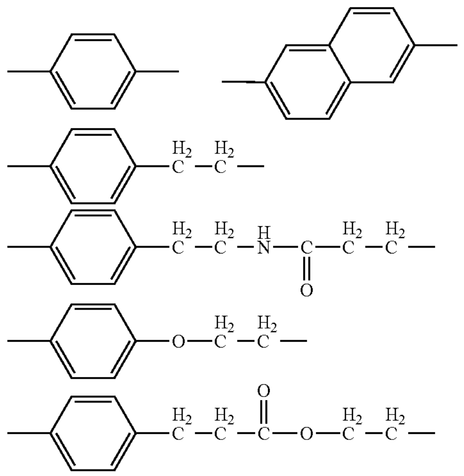

One embodiment of the present invention relates to a fluorescent labeling agent containing the fluorescent dye. This fluorescent labeling agent is applicable for fluorescent labeling in bioimaging in a wide range of fields from biochemical research to medical analyses. For example, the fluorescent labeling agent can be used for fluorescent labeling and other uses in the genetic diagnosis field, the immunodiagnosis field, the medical development field, the regenerative medicine field, the environmental testing field, the biotechnology field, the fluorescent inspection field, and other fields.

Particularly, in the fluorescent labeling agent of the embodiment, the structure represented by $—Z—R_1—R_2—R_3$ (substituent) in the fluorescent dye has a function of interacting with phospholipids. Therefore, the fluorescent labeling agent can be preferably used as a phospholipid accumulation-type fluorescent labeling agent. The phospholipid accumulation-type fluorescent labeling agent can be preferably used as a fluorescent labeling agent in the dyeing of cell membranes, tracking of exosomes, liposome imaging for drug delivery system (DDS), and the like.

In the fluorescent labeling agent of the embodiment, the concentration of the fluorescent dye is not particularly limited. For example, in the case of handling cells, the concentration of the fluorescent dye is preferably as low as possible in consideration of the influence on the functional disorder of the cells, the inhibition of growth, and the like. In one embodiment, the concentration of the fluorescent dye with respect to 10,000 cells/well of cells seeded in a 96-well plate is preferably 100 M or lower. The concentration is more preferably 50 M or lower and still more preferably 10 M or lower. The fluorescent labeling agent of the embodiment enables imaging with a high fluorescence intensity even when the concentration of the fluorescent dye is low due to the excellent property of being accumulated in phospholipids. Therefore, even when the concentration of the fluorescent dye is low, for example, 2 M or lower, the fluorescent labeling agent enables detection with higher accuracy.

The fluorescent labeling agent of the embodiment needs to contain the fluorescent dye of the embodiment and may also contain other components as necessary. The other components may be well-known components in the corresponding technical fields. Examples thereof include a solvent, an amphipathic substance, and the like.

The solvent may be water or an organic solvent and is more preferably water. In consideration of the solubility of the fluorescent dye, water and an organic solvent may be used as a mixture. For example, the organic solvent is preferably ethanol or dimethyl sulfoxide (DMSO).

The amphipathic substance is a generic term of compounds having a hydrophilic group and a hydrophobic group in one molecule. Specific examples thereof include surfactants, phospholipids, and the like. Only one kind of amphipathic substance may be used or two or more amphipathic substances may be used as a mixture. In the fluorescent labeling agent of the embodiment, the amphipathic substance is not particularly limited and may be any compound as long as the compound is capable of solubilizing water-insoluble fluorescent dyes that emit fluorescence in the near-infrared range in water. While not particularly limited, specific examples of the amphipathic substance that can be used include the followings.

Examples of the surfactants include nonionic surfactants, cationic surfactants, anionic surfactants, polymer surfactants, and the like.

Examples of the nonionic surfactants include polyoxyethylene sorbitan-based fatty acid esters such as Tween (registered trademark) 20, Tween (registered trademark) 40, Tween (registered trademark) 60, and Tween (registered trademark) 80, polyoxyethylene castor oil derivatives such as Cremophor (registered trademark) EL and Cremophor (registered trademark) RH60, 12-hydroxy stearic acid-polyethylene glycol copolymers such as Solutol (registered trademark) HS15, octylphenol ethoxylates such as Triton (registered trademark) X-100 and Triton (registered trademark) X-114, and the like.

Examples of the cationic surfactants include alkyltrimethylammonium salts such as stearyltrimethylammonium chloride and lauryltrimethylammonium chloride, alkylpyridinium salts such as cetylpyridinium chloride, alkyl quaternary ammonium salts such as distearyldimethylammonium chloride, dialkyldimethylammonium salt, and poly(N,N'-dimethyl-3,5-methylene piperidinium) chloride, alkyldimethylbenzylammonium salts, alkylisoquinolinium salts, dialkylmorpholinium salts, polyoxyethylenealkylamine, alkylamine salts, polyamine fatty acid derivatives, amyl alcohol fatty acid derivatives, benzalkonium chloride, benzethonium chloride, and the like.

Examples of the anionic surfactants include sodium dodecyl sulfate, dodecylbenzene sulfonate, decylbenzene sulfonate, undecylbenzene sulfonate, tridecylbenzene sulfonate, and nonylbenzene sulfonate, sodium, potassium and ammonium salts thereof, and the like.

Examples of the polymer surfactants include block copolymers of polyvinyl alcohol, polyoxyethylene polyoxypropylene glycol, polyethylene glycol-polyalkyl, polyethylene glycol-polylactic acid, polyethylene glycol-polycaprolactone, polyethylene glycol-polyglycolic acid, polyethylene glycol-poly(lactide-glycolide).

In one embodiment, the fluorescent labeling agent of the embodiment may contain one or more of the compounds exemplified as the amphipathic substance. However, the fluorescent labeling agent of the embodiment has an excellent property of being accumulated in a target site such as phospholipids and thus enables high-sensitivity detection with no need of any amphipathic substance.

In the fluorescent labeling agent of the embodiment, the fluorescent dye preferably contains a phthalocyanine dye. A method for synthesizing the phthalocyanine dye is not particularly limited. For example, first, a dye having a phthalocyanine skeleton (phthalocyanine metal complex) is synthesized by a well-known method using a phthalonitrile derivative as a raw material. Next, a component having a substituent (—Z—$R_1$—$R_2$—$R_3$) is added to the dye, and the component and the dye are reacted in a dimethyl sulfoxide solvent while being heated and stirred. Such a reaction makes it possible to obtain a desired fluorescent dye. As the component having a substituent, it is possible to use, for example, an acidic compound or a compound to be mentioned as an axial ligand in examples to be described below.

In a case where the phthalonitrile derivative, which is a raw material, is an asymmetric structure, phthalocyanine is obtained as a mixture of isomers each having a substituent at a different position. Hereinafter, in the present specification, only one example of the phthalocyanine structure will be shown, which does not exclude isomers each having a substituent at a different position.

Specific examples of the fluorescent dye, which is one embodiment of the present invention, include the following. Here, the fluorescent dye according to the present invention is not limited thereto.

TABLE 1-1

| | |
|---|---|
| 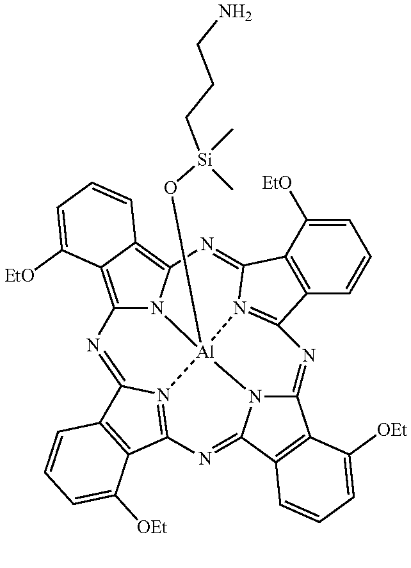 | Fluorescent dye 1 |

TABLE 1-1-continued
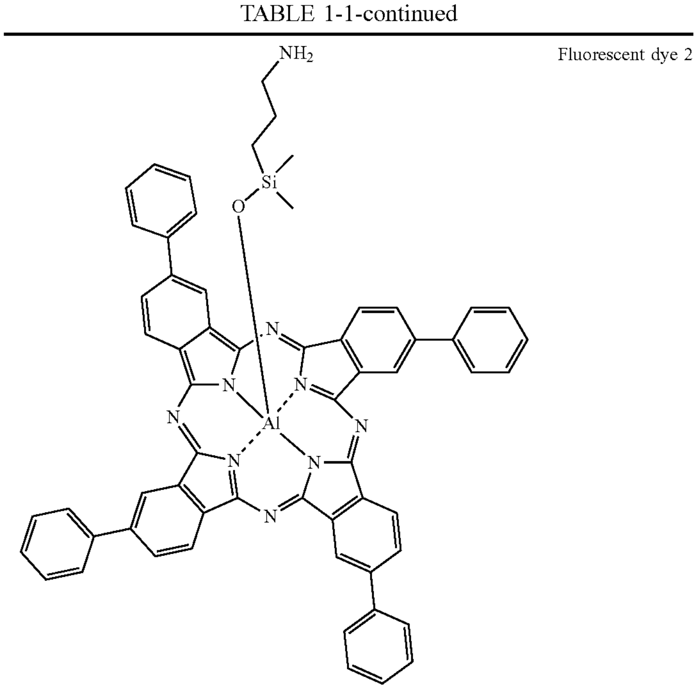
Fluorescent dye 2
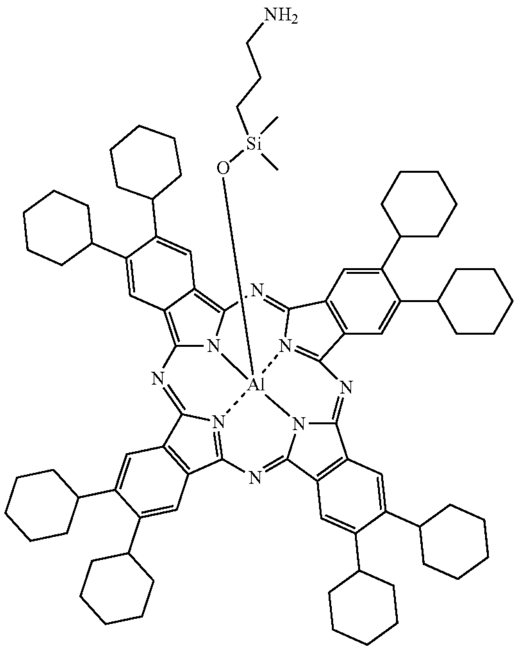
Fluorescent dye 3

TABLE 1-1-continued
Fluorescent dye 4
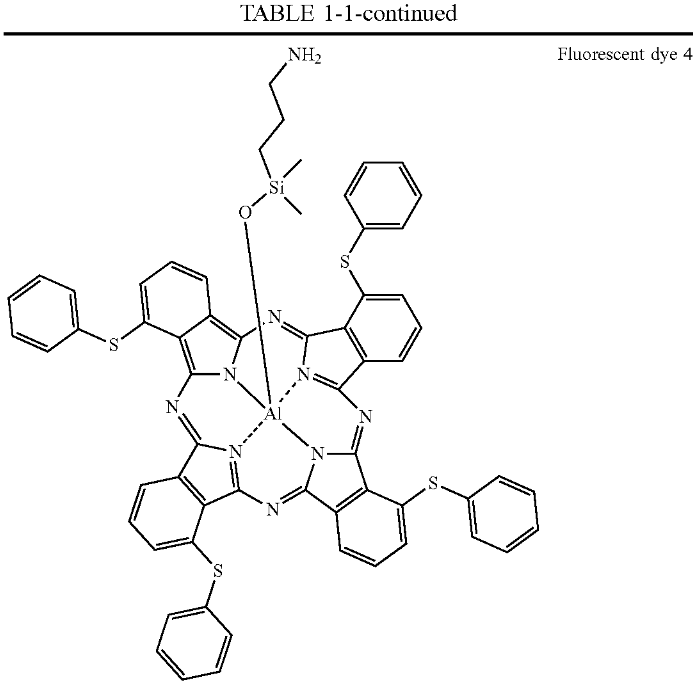
Fluorescent dye 5
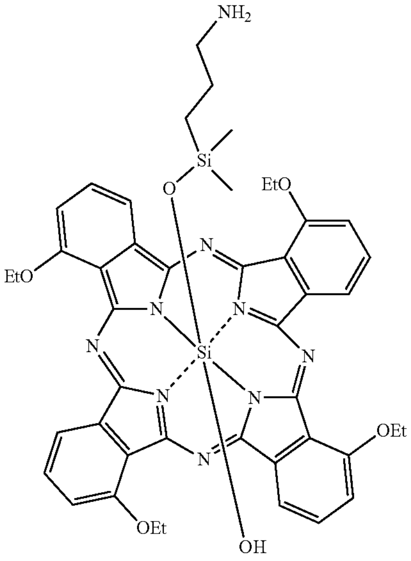

TABLE 1-1-continued
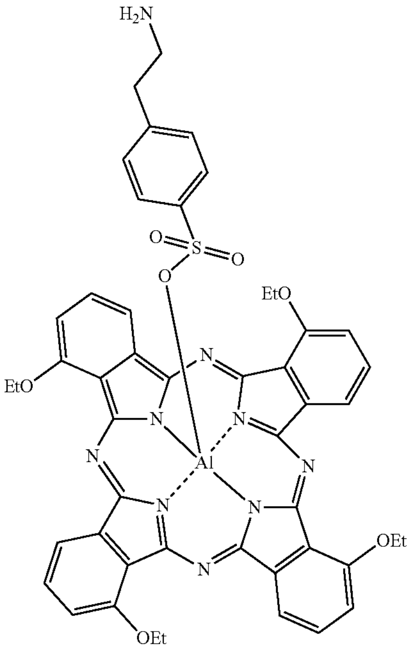
Fluorescent dye 6
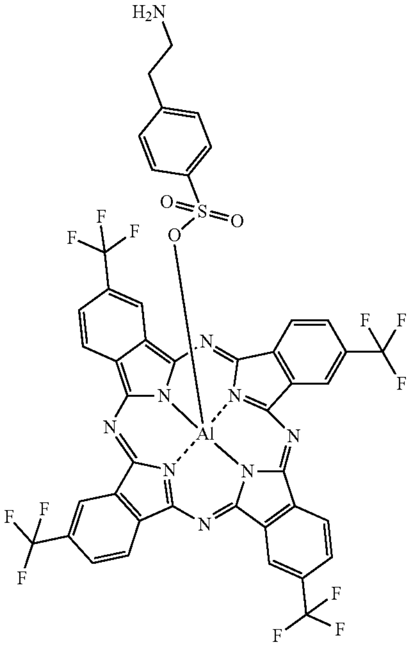
Fluorescent dye 7

TABLE 1-1-continued
Fluorescent dye 8
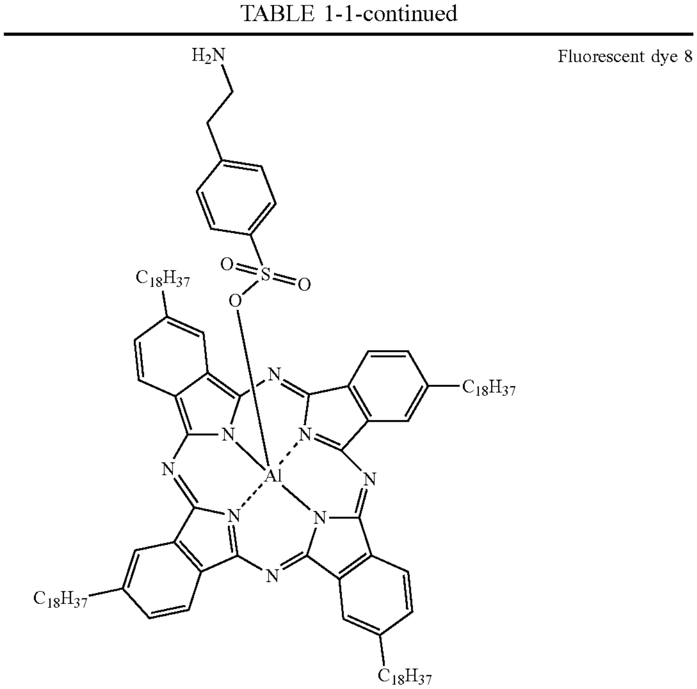
Fluorescent dye 9
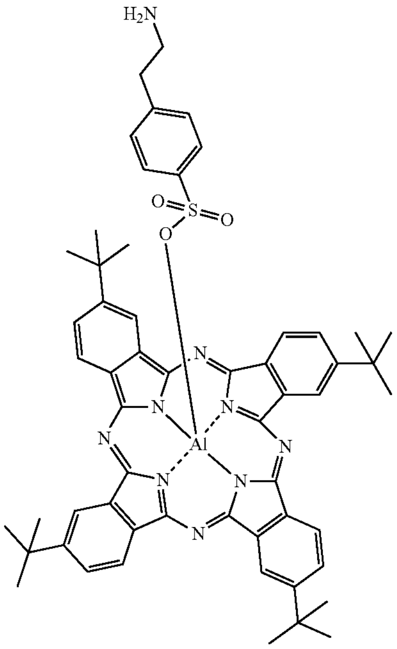

TABLE 1-1-continued
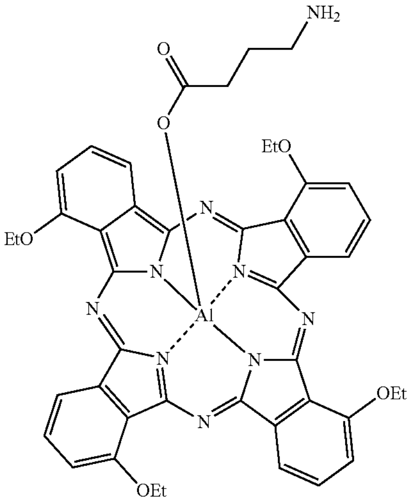
Fluorescent dye 10
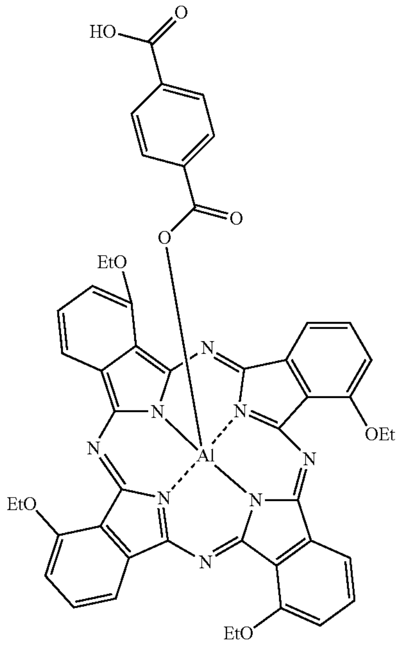
Fluorescent dye 11

TABLE 1-1-continued
| | |
|---|---|
| 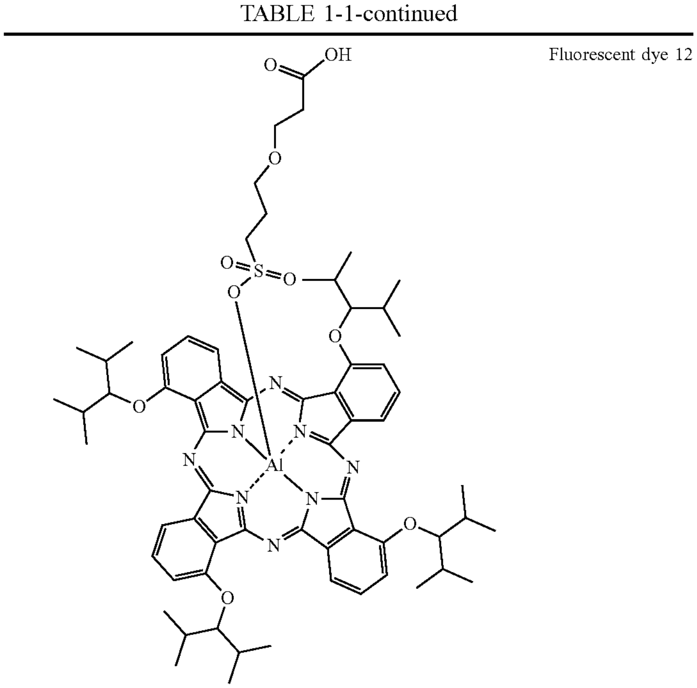 | Fluorescent dye 12 |
TABLE 1-2
| | |
|---|---|
| 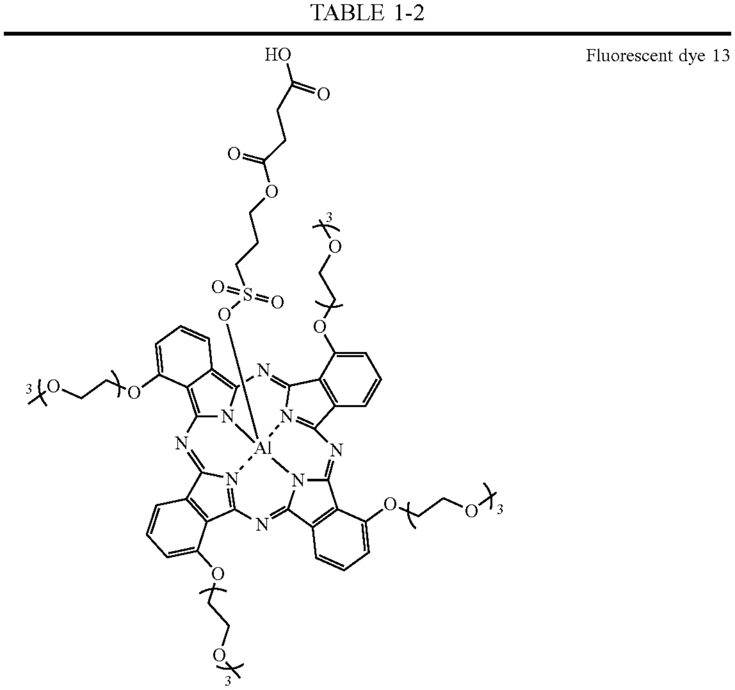 | Fluorescent dye 13 |

TABLE 1-2-continued
Fluorescent dye 14
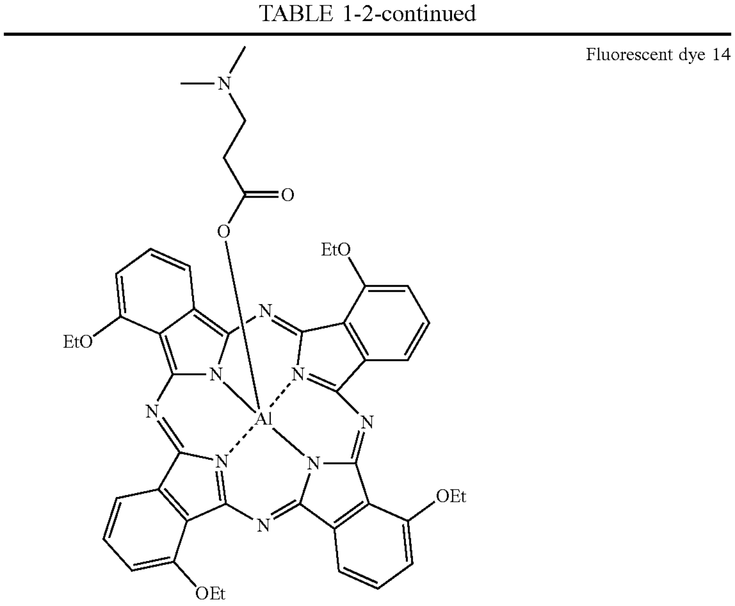
Fluorescent dye 15
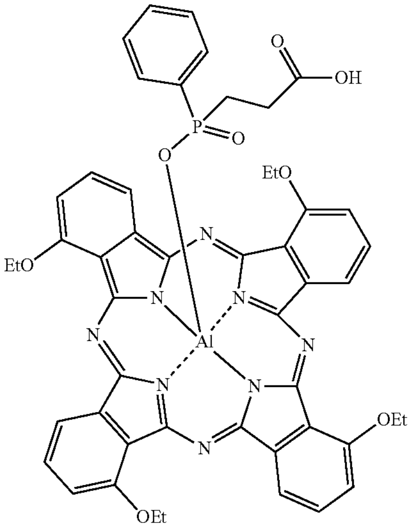
Fluorescent dye 16
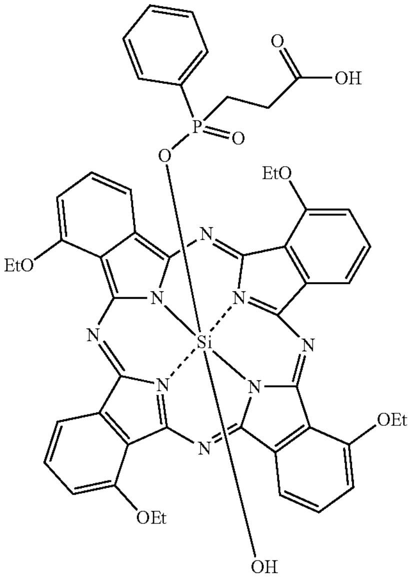

TABLE 1-2-continued
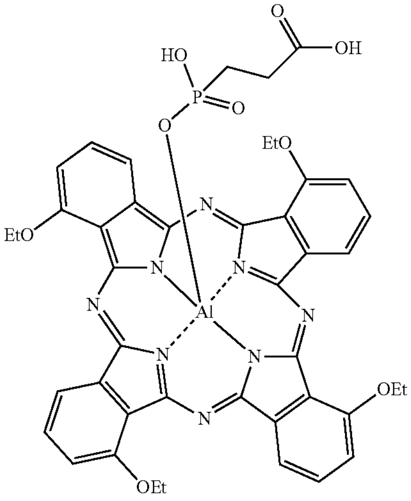
Fluorescent dye 17
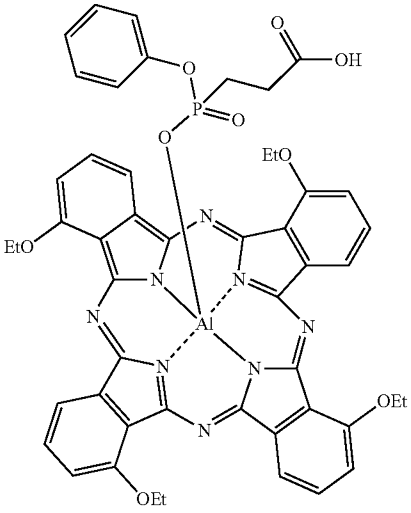
Fluorescent dye 18
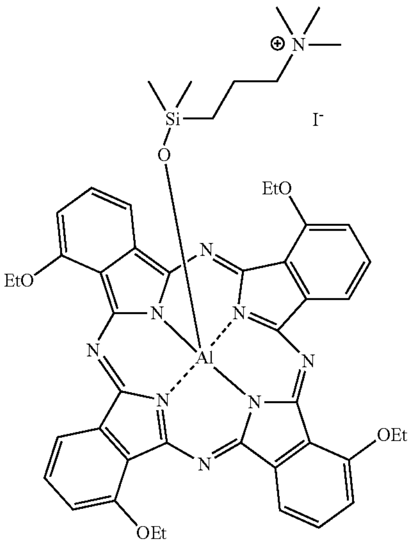
Fluorescent dye 19

TABLE 1-2-continued
Fluorescent dye 20
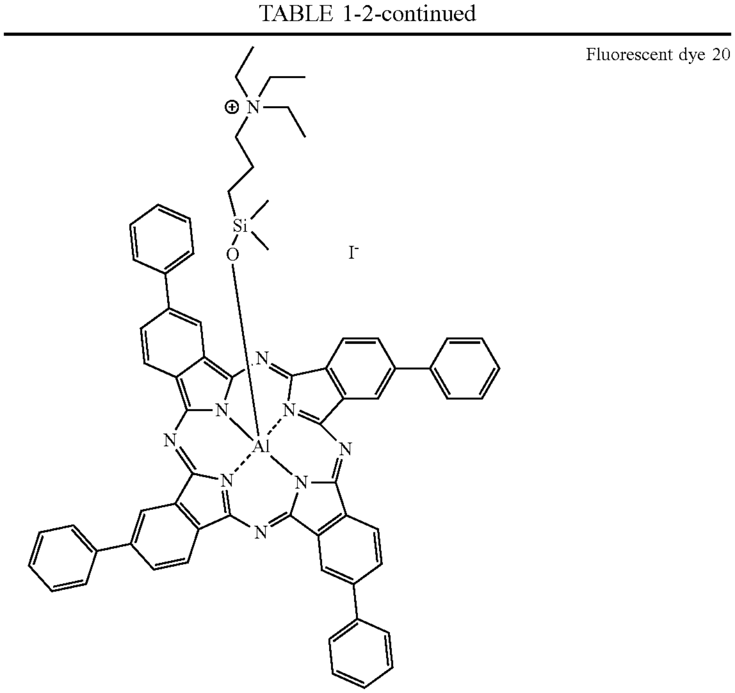
Fluorescent dye 21
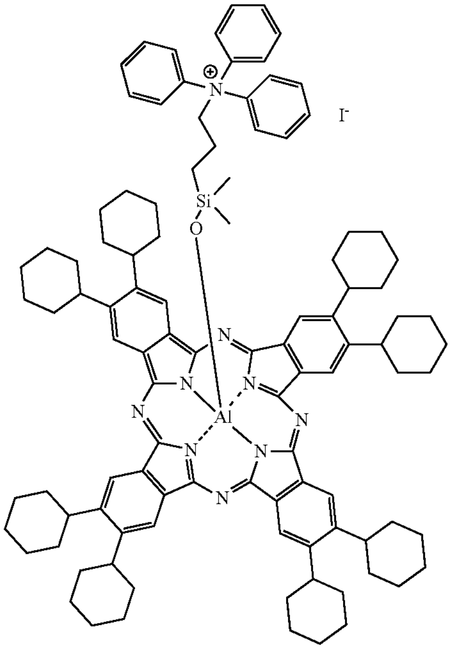

TABLE 1-2-continued
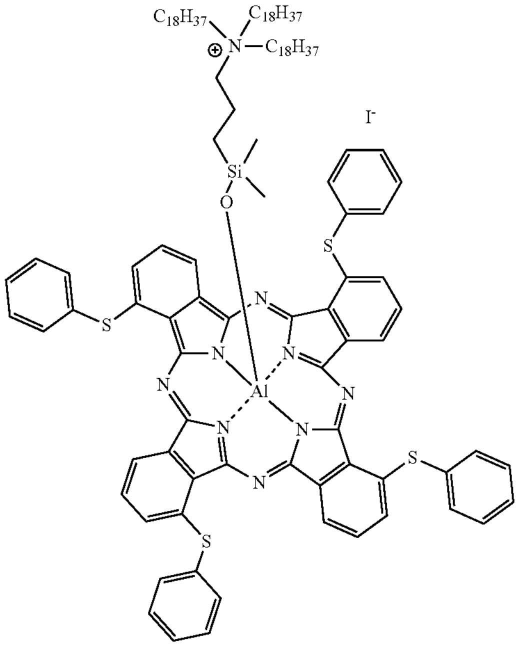
Fluorescent dye 22
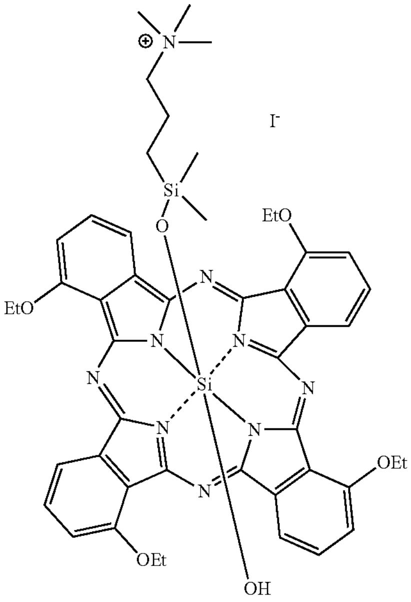
Fluorescent dye 23

TABLE 1-2-continued
| | |
|---|---|
| 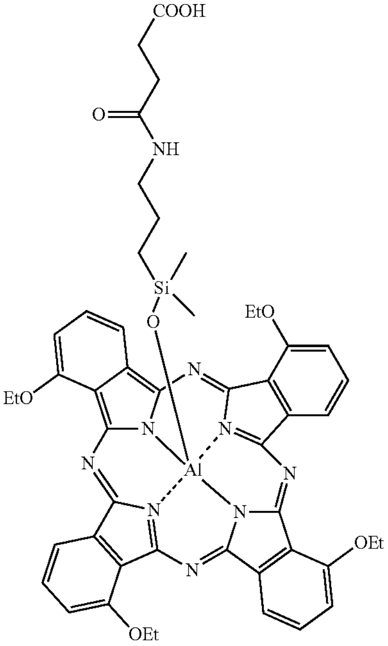 | Fluorescent dye 24 |
TABLE 1-3
| | |
|---|---|
| 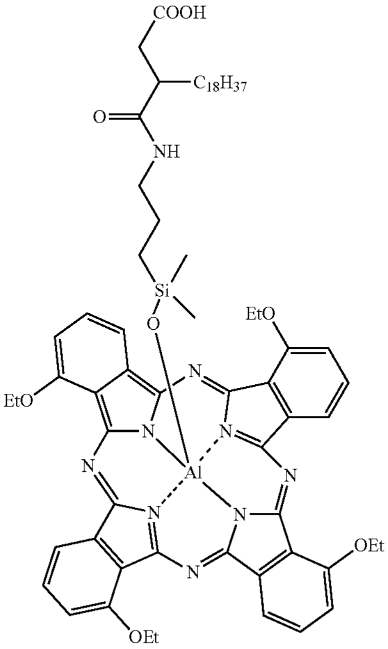 | Fluorescent dye 25 |

TABLE 1-3-continued
Fluorescent dye 26
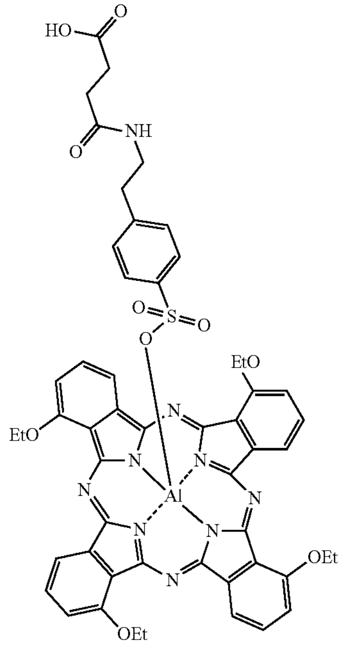
Fluorescent dye 27
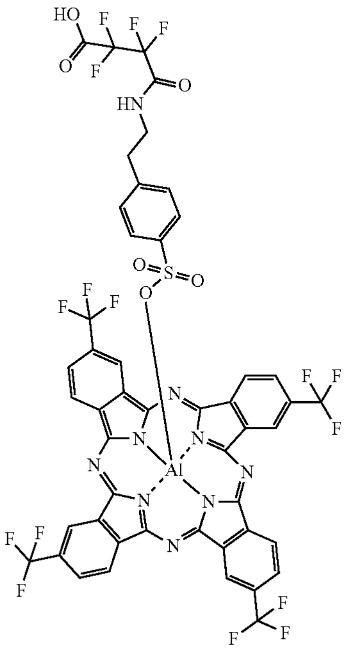

TABLE 1-3-continued
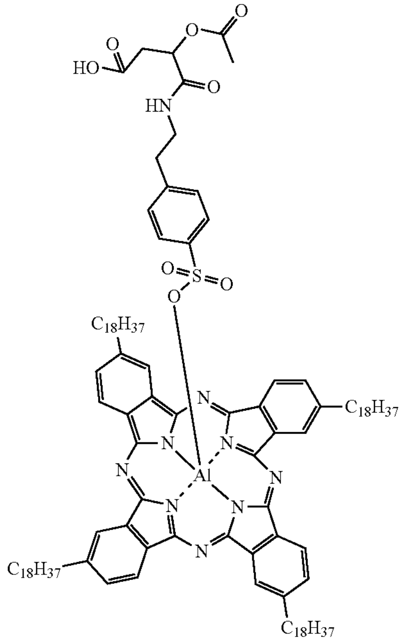
Fluorescent dye 28
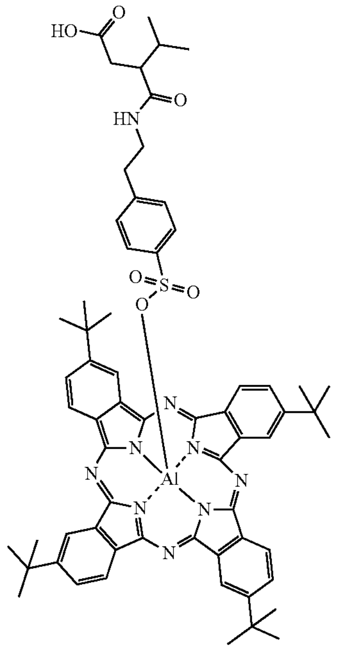
Fluorescent dye 29

TABLE 1-3-continued
Fluorescent dye 30
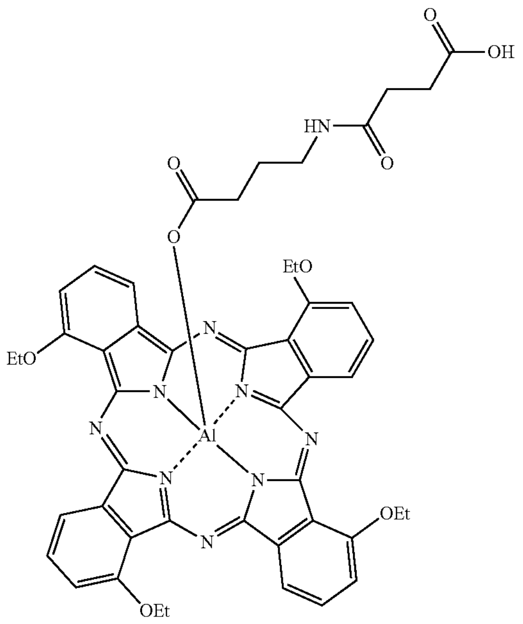
Fluorescent dye 31
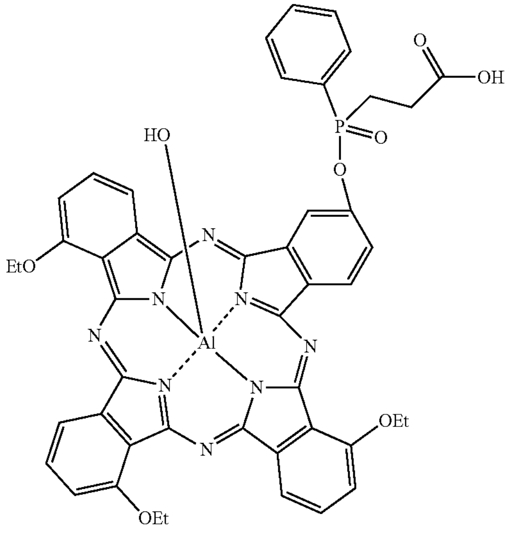
Fluorescent dye 32
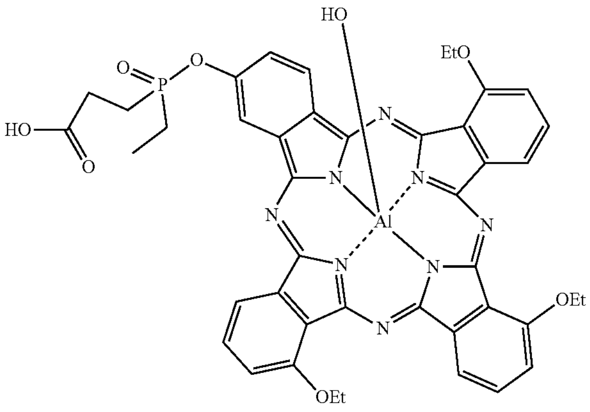

TABLE 1-3-continued
Fluorescent dye 33
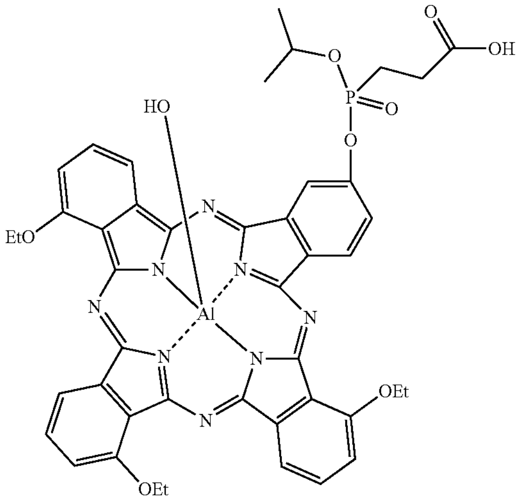
Fluorescent dye 34
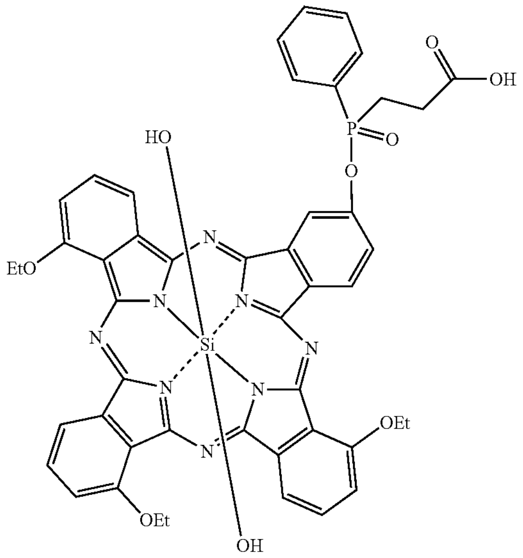
Fluorescent dye 35
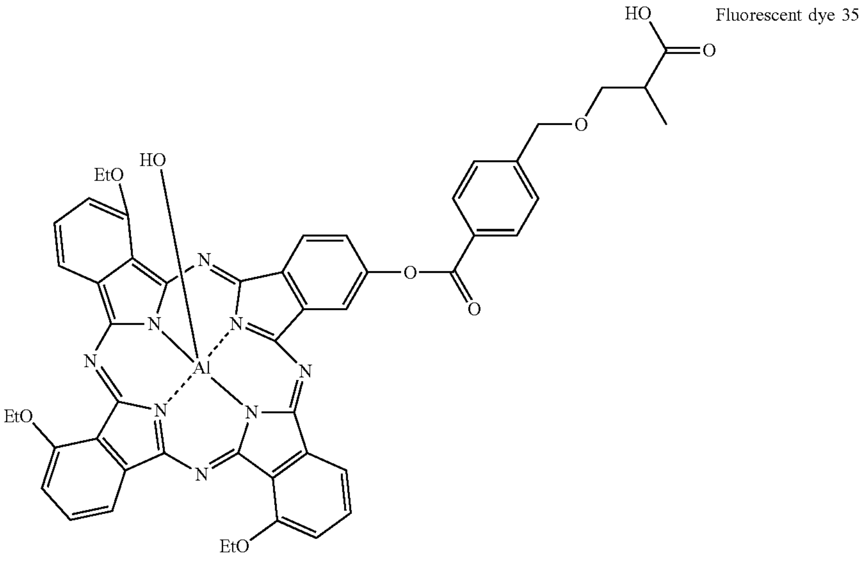

TABLE 1-4
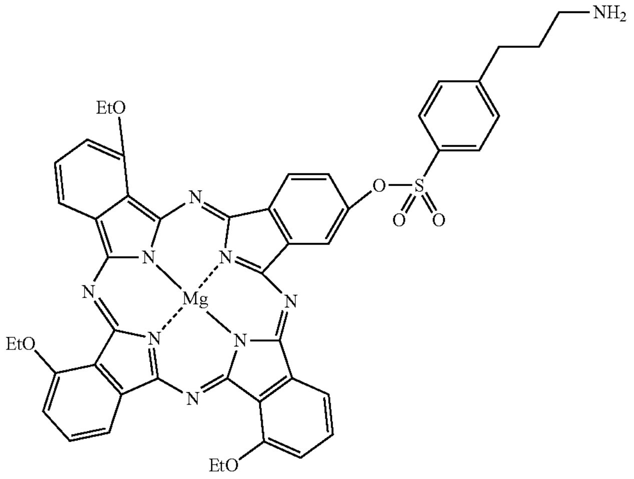
Fluorescent dye 36
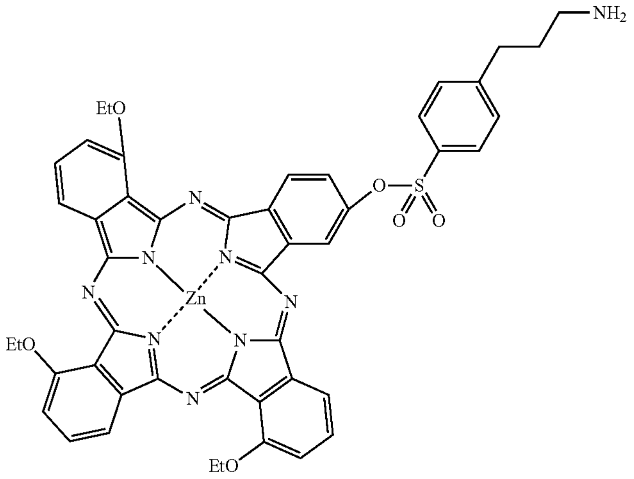
Fluorescent dye 37
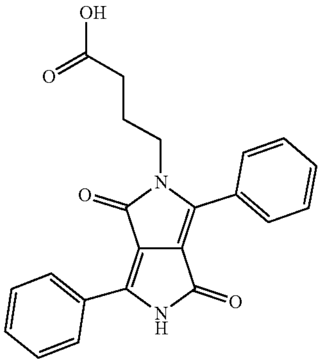 [SMILES: O=C(O)CCCN1C(=O)C2=C(c3ccccc3)NC(=O)C2=C1c1ccccc1]
Fluorescent dye 38
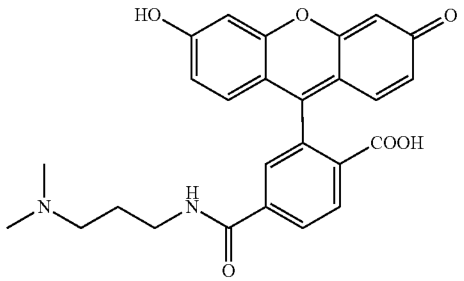 [SMILES: CN(C)CCCNC(=O)c1ccc(C(=O)O)c(-c2c3ccc(=O)cc-3oc3cc(O)ccc23)c1]
Fluorescent dye 39

TABLE 1-4-continued

Fluorescent dye 40

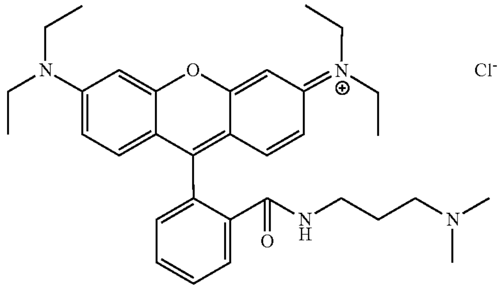 [SMILES: CCN(CC)c1ccc2c(-c3ccccc3C(=O)NCCCN(C)C)c3ccc(=[N+](CC)CC)cc-3oc2c1 ; [Cl-]]

Fluorescent dye 41

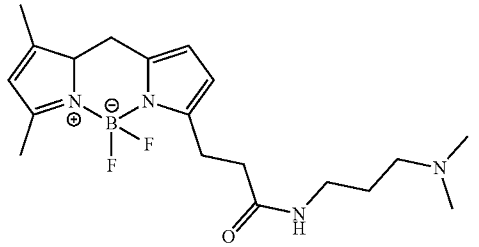 [SMILES: CC1=CC(C)=[N+]2C1Cc1ccc(CCC(=O)NCCCN(C)C)n1[B-]2(F)F]

In the above-exemplified fluorescent dyes, fluorescent dyes 1 to 37 are each a fluorescent dye having the skeleton of the phthalocyanine dye (the residue of the dye). A fluorescent dye 38 is a fluorescent dye having the skeleton of a diketopyrrolopyrrole dye. Fluorescent dyes 39 and 40 are fluorescent dyes having the skeleton of a xanthene dye.

A fluorescent dye 41 is a fluorescent dye having the skeleton of a boron-dipyrromethene dye (the residue of the dye). For example, in a substituent "—Z—$R_1$—$R_2$—$R_3$" in the fluorescent dye 41, Z is $C_2H_4$—, $R_1$ is —C(═O)NH—, $R_2$ is —$C_3H_6$—, and $R_3$ is —$N(CH_3)_2$.

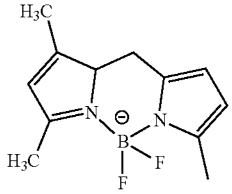

TABLE 1-5

Fluorescent dye 42

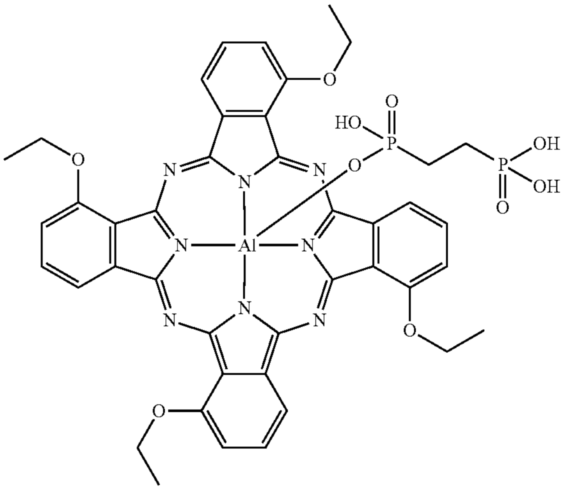

TABLE 1-5-continued
Fluorescent dye 43
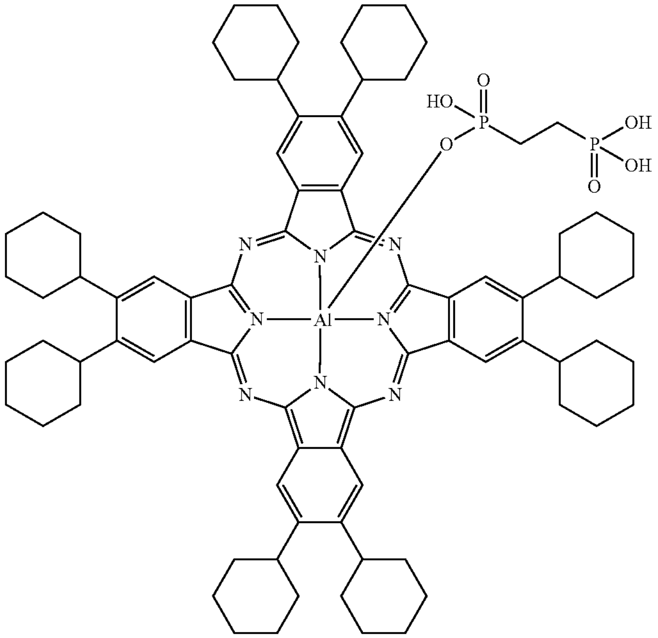
Fluorescent dye 44
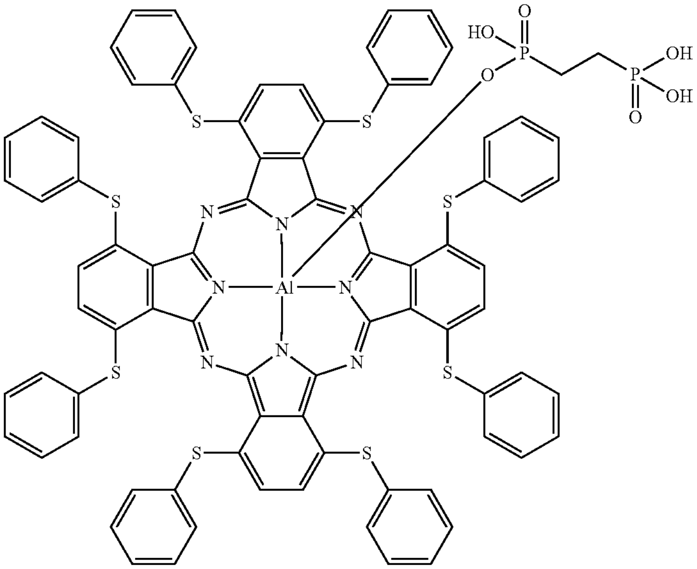

TABLE 1-5-continued
Fluorescent dye 45
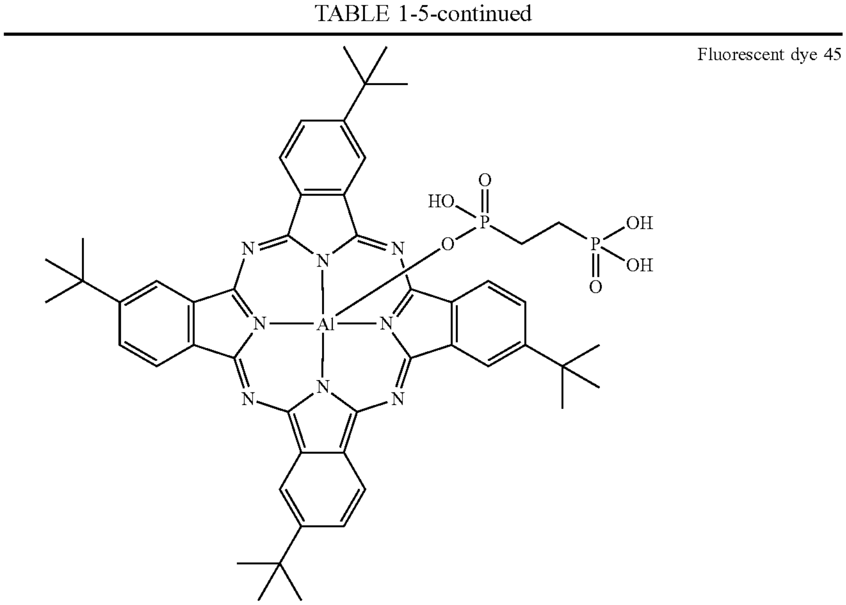
Fluorescent dye 46
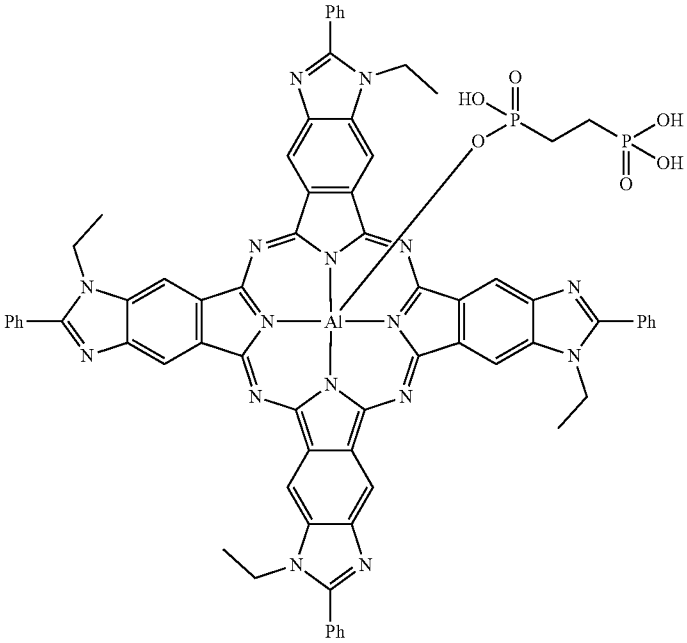

TABLE 1-5-continued
Fluorescent dye 47
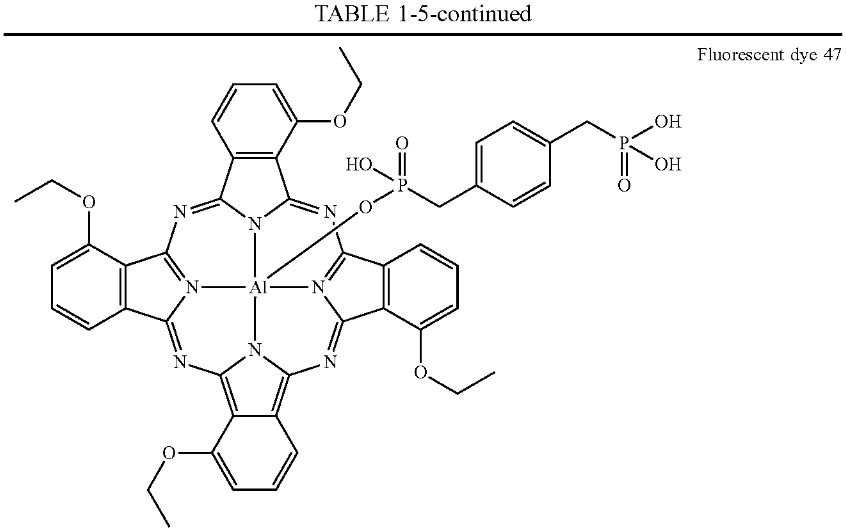
TABLE 1-6
Fluorescent dye 48
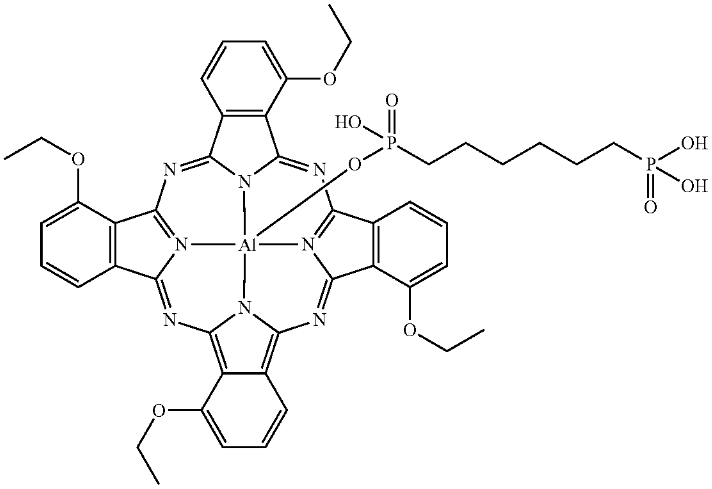
Fluorescent dye 49
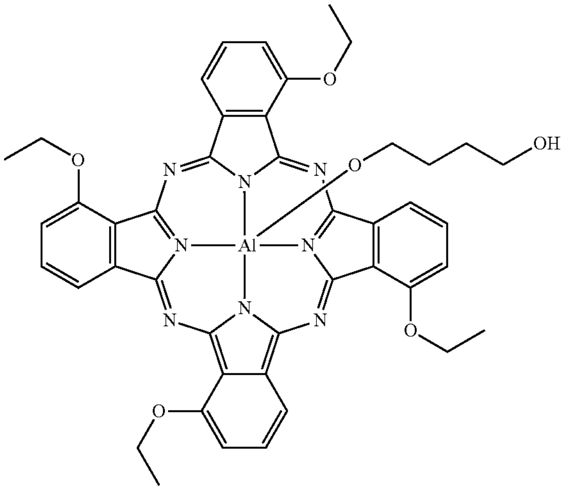

TABLE 1-6-continued
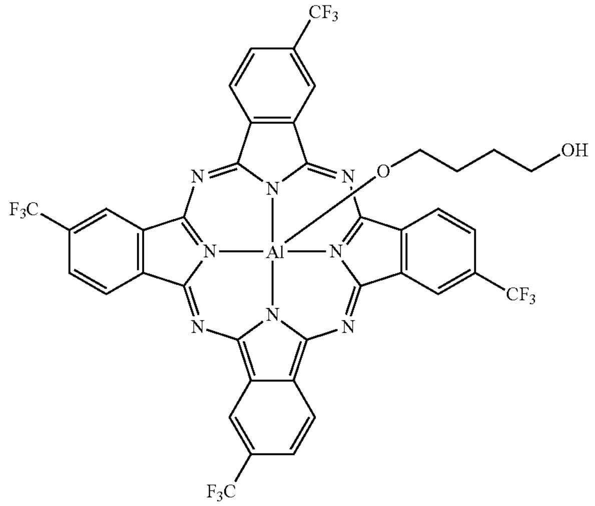
Fluorescent dye 50
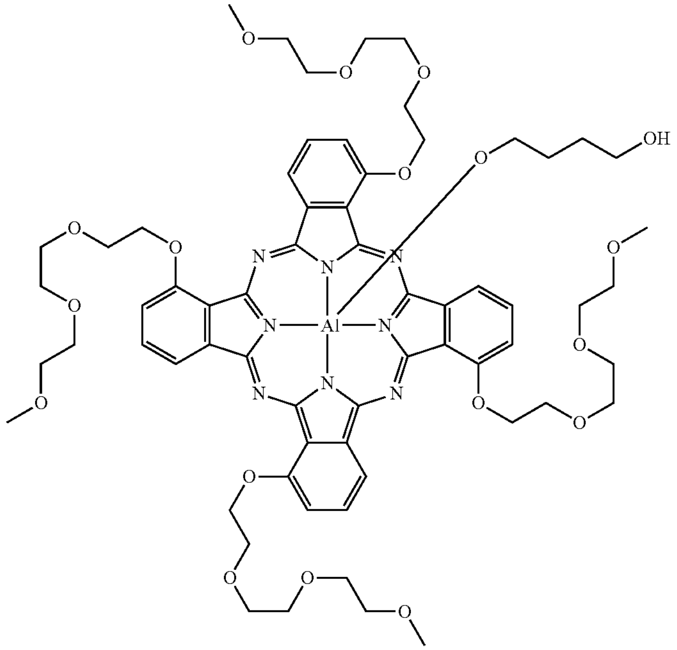
Fluorescent dye 51

TABLE 1-6-continued
Fluorescent dye 52
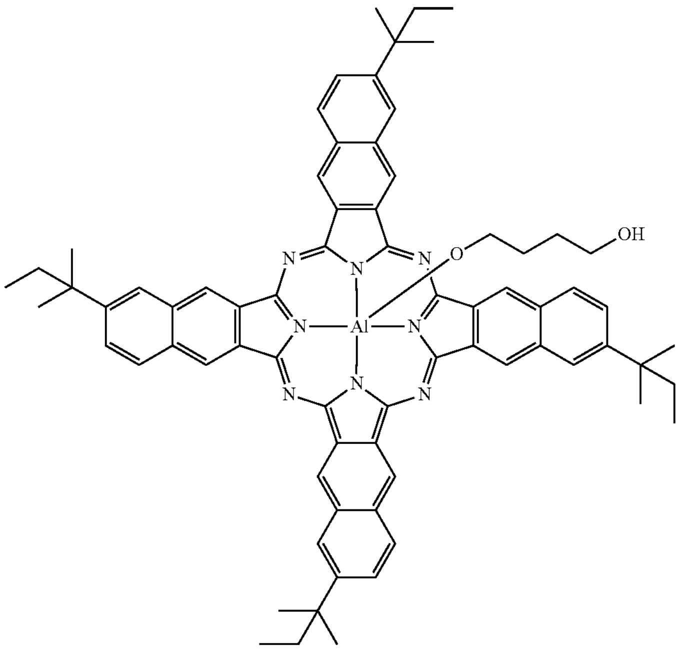
Fluorescent dye 53
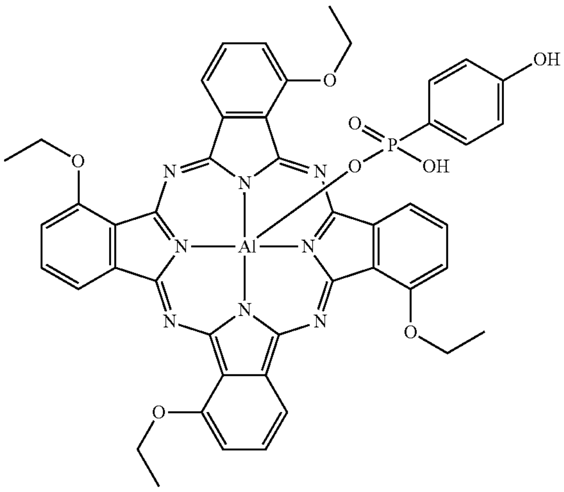

TABLE 1-7
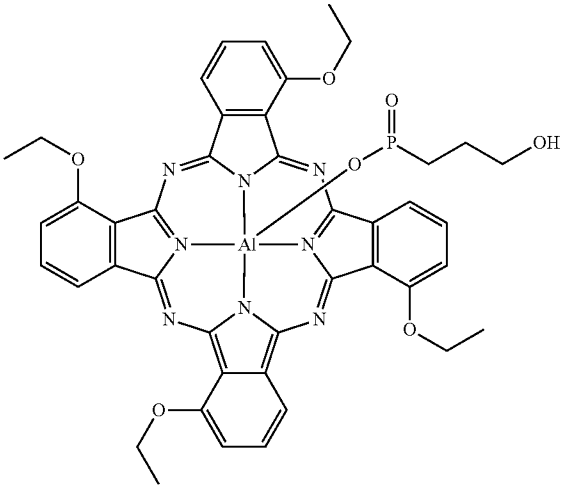
Fluorescent dye 54
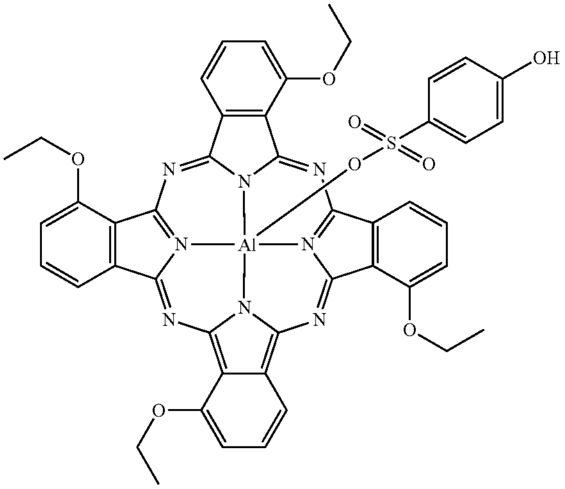
Fluorescent dye 55
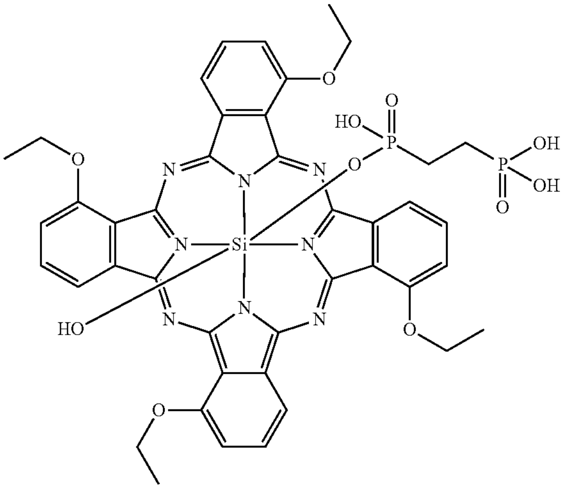
Fluorescent dye 56

TABLE 1-7-continued
Fluorescent dye 57
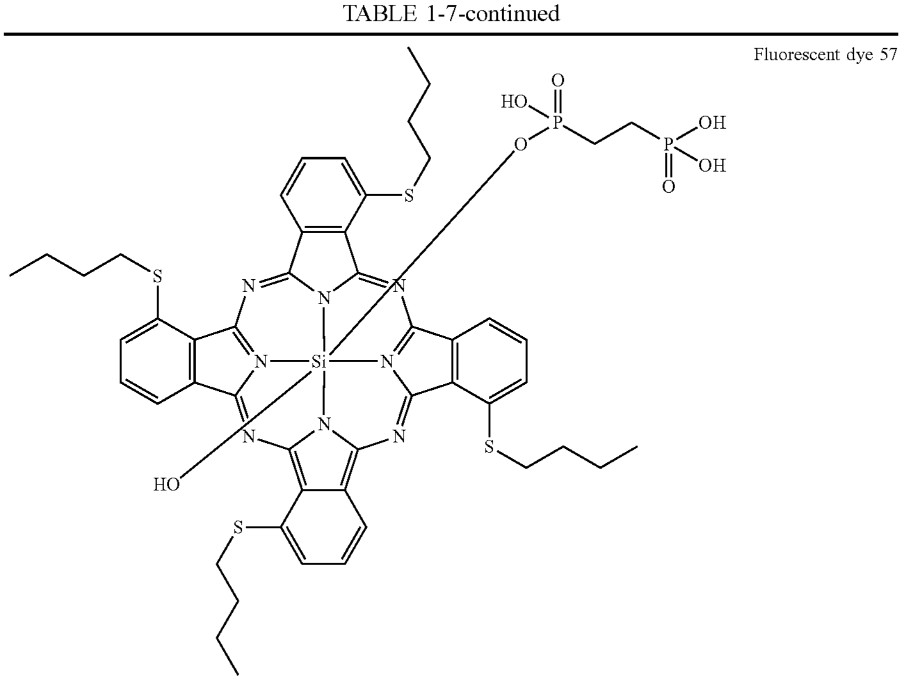
Fluorescent dye 58
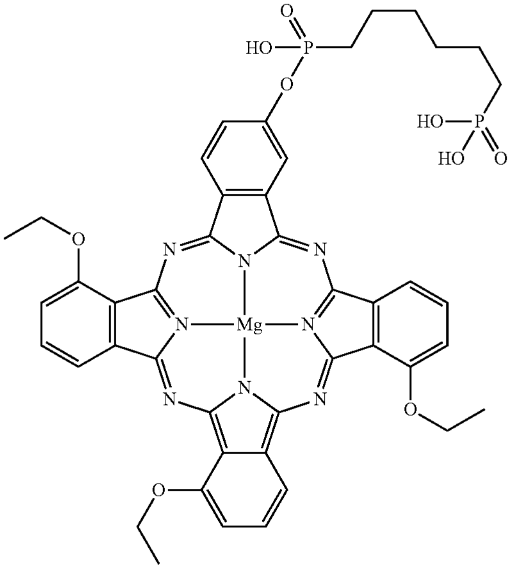

TABLE 1-7-continued
Fluorescent dye 59
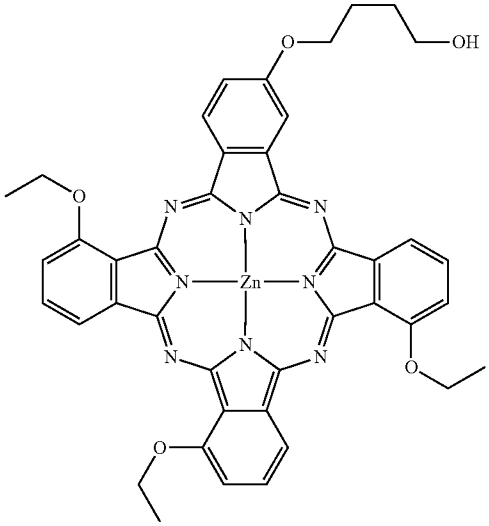
TABLE 1-8
Fluorescent dye 60
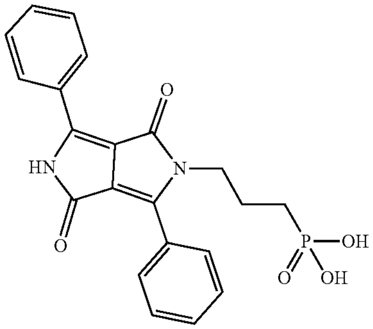 [SMILES: O=C1NC(c2ccccc2)=C2C(=O)N(CCCP(=O)(O)O)C(c3ccccc3)=C12]
Fluorescent dye 61
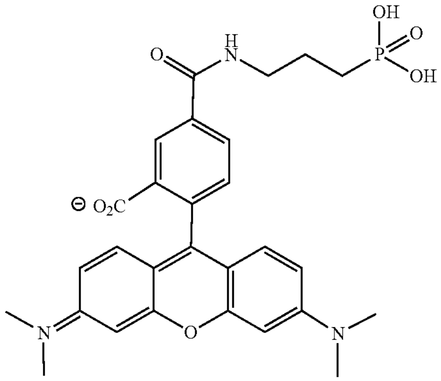

TABLE 1-8-continued

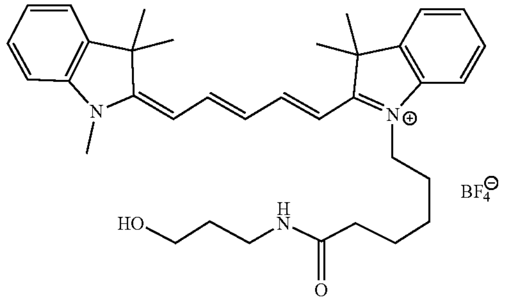

Fluorescent dye 62

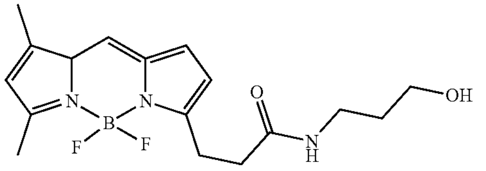

Fluorescent dye 63

In the above-exemplified fluorescent dyes, fluorescent dyes 42 to 59 are each a fluorescent dye having the skeleton of the phthalocyanine dye. A fluorescent dye 60 is a fluorescent dye having the skeleton of a diketopyrrolopyrrole dye. A fluorescent dye 61 is a fluorescent dye having the skeleton of a xanthene dye. A fluorescent dye 62 is a fluorescent dye having the skeleton of a cyanine dye. A fluorescent dye 63 is a fluorescent dye having the skeleton of a boron-dipyrromethene dye.

While not particularly limited, in one embodiment, the fluorescent labeling agent preferably contains a fluorescent dye having the skeleton of the phthalocyanine dye from the viewpoint of stability such as durability.

EXAMPLES

Hereinafter, the present invention will be described based on examples, but the present invention is not limited by the examples. "Parts" in the examples indicates "parts by mass".

(Mass Analysis)

Masses were analyzed with a mass analyzer (TOF-MS: autoflex 11 manufactured by Bruker Daltonics).

<I> Fluorescent Dye

Manufacturing Example 1

<Manufacturing Method of Compound A-1>

An ammonia gas was introduced into a solution of 50 parts of quinoline and 1 part of anhydrous aluminum chloride, furthermore, 5 parts of 3-ethoxyphthalonitrile was added thereto, and these components were reacted at 180° C. for seven hours. This reaction liquid is cooled to room temperature, and then 200 parts of methanol and 200 parts of a 10% hydrochloric acid aqueous solution were added thereto. Next, a precipitated solid was filtered, and the solid was washed with 200 parts of water. The washed solid was dried at 80° C., thereby obtaining 4.7 parts of a compound A-1 shown in Table 2 (yield: 88.4%).

Manufacturing Examples 2 to 11

<Manufacturing Methods of Compounds A-2 to A-10>

Compounds A-2 to A-10 shown in Table 2 were each manufactured in the same manner as in the manufacturing of the compound A-1 except that 3-ethoxyphthalonitrile and anhydrous aluminum chloride used in the manufacturing method of the compound A-1 were changed to a phthalonitrile derivative and a metal source shown in Table 2. The phthalonitrile derivative and the metal source were used in the same molar quantities as those of 3-ethoxyphthalonitrile and anhydrous aluminum chloride in the manufacturing of the compound A-1, respectively.

TABLE 2-1
| | Phthalonitrile derivative | Metal source | Compound A |
|---|---|---|---|
| Manufacturing Example 1 | 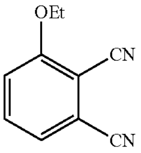 [SMILES: CCOc1cccc(C#N)c1C#N] | $AlCl_3$ | A-1 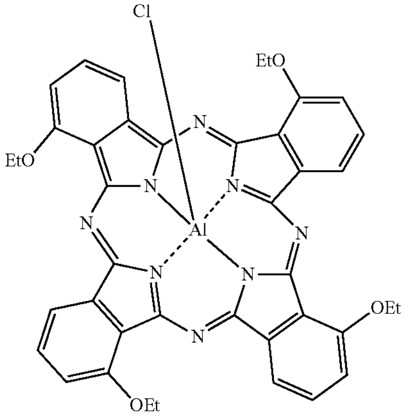 |
| Manufacturing Example 2 | 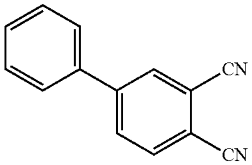 [SMILES: N#Cc1ccc(-c2ccccc2)cc1C#N] | $AlCl_3$ | A-2 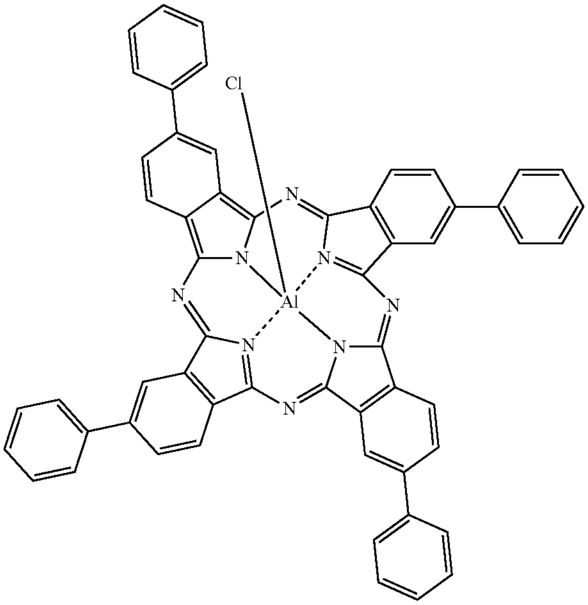 |

TABLE 2-1-continued
| | Phthalonitrile derivative | Metal source | Compound A |
|---|---|---|---|
| Manufacturing Example 3 | 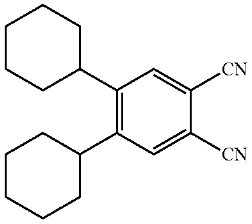 [SMILES: N#Cc1cc(C2CCCCC2)c(C2CCCCC2)cc1C#N] | $AlCl_3$ | A-3 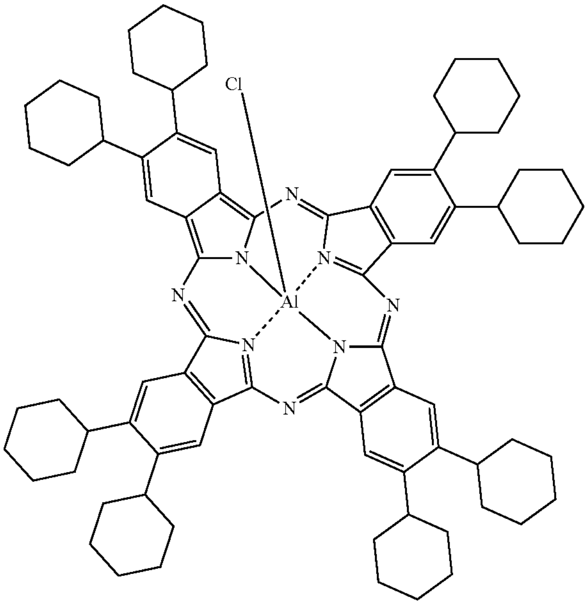 |
| Manufacturing Example 4 | 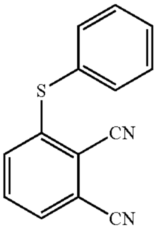 [SMILES: N#Cc1cccc(Sc2ccccc2)c1C#N] | $AlCl_3$ | A-4 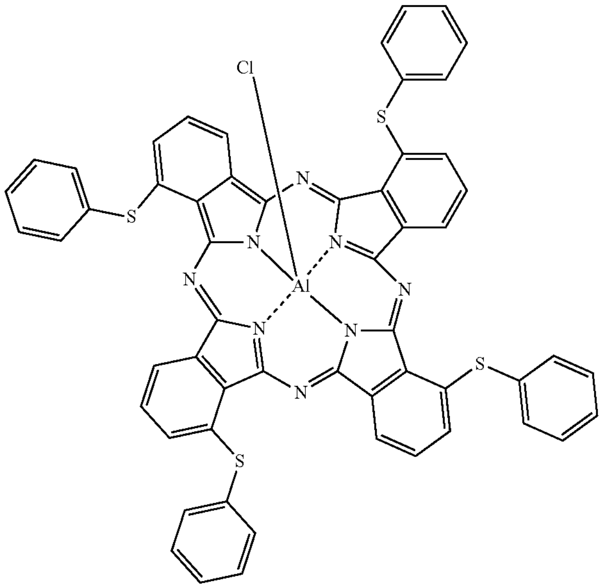 |

TABLE 2-1-continued
| | Phthalonitrile derivative | Metal source | Compound A |
|---|---|---|---|
| Manufacturing Example 5 | 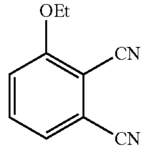 [SMILES: CCOc1cccc(C#N)c1C#N] | $SiCl_4$ | A-5 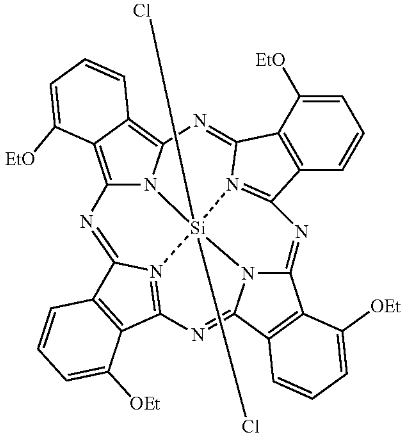 |
TABLE 2-2
| | Phthalonitrile derivative | Metal source | Compound A |
|---|---|---|---|
| Manufacturing Example 6 | 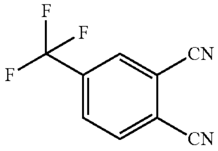 [SMILES: N#Cc1ccc(C(F)(F)F)cc1C#N] | $AlCl_3$ | A-6 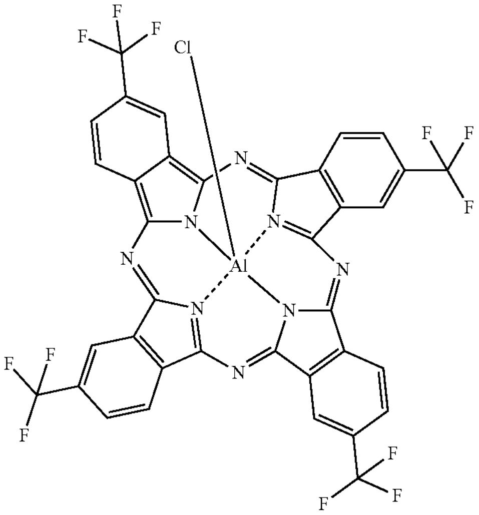 |

TABLE 2-2-continued
| | Phthalonitrile derivative | Metal source | Compound A |
|---|---|---|---|
| Manufacturing Example 7 | 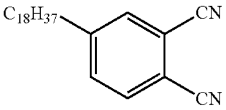 | $AlCl_3$ | A-7 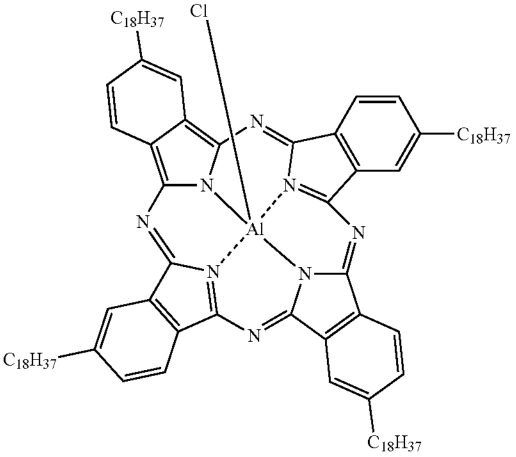 |
| Manufacturing Example 8 | 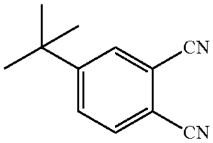 | $AlCl_3$ | A-8 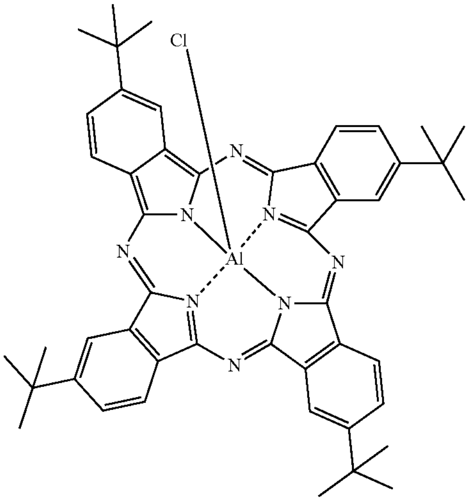 |

TABLE 2-2-continued
| | Phthalonitrile derivative | Metal source | Compound A |
|---|---|---|---|
| Manufacturing Example 9 | 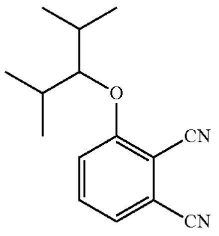 [SMILES: CC(C)C(Oc1cccc(C#N)c1C#N)C(C)C] | $AlCl_3$ | A-9 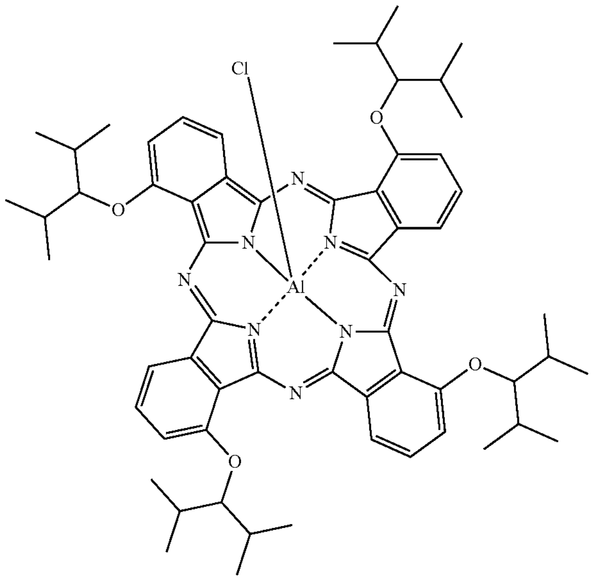 |
| Manufacturing Example 10 | 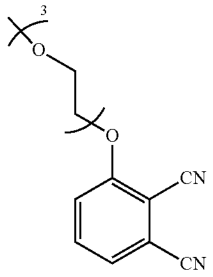 | $AlCl_3$ | A-10 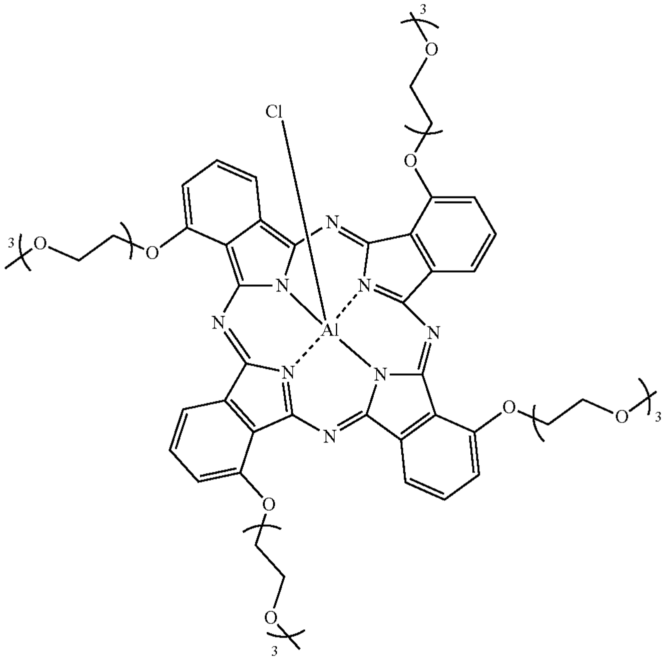 |

Manufacturing Example 11

<Manufacturing Method of Compound B-1>

An aqueous solution obtained by dissolving 0.45 parts of potassium hydroxide in 1 part of water was fully added to a solution obtained by dissolving 3 parts of the compound A-1 in 10 parts of N-methyl-2-pyrrolidone (NMP). These components were reacted at 110° C. for seven hours. This reaction liquid is cooled to room temperature, and then 100 parts of water was added thereto. Next, a precipitated solid was filtered, and the solid was washed with 100 parts of water. The washed solid was dried at 80° C., thereby obtaining 2.9 parts of a compound B-1 shown in Table 3 (yield: 99.2%).

Manufacturing Examples 12 to 15

<Manufacturing Methods of Compounds B-2 to B-5>

Compounds B-2 to B-5 shown in Table 3 were each manufactured in the same manner as in the manufacturing of the compound B-1 except that the compound A-1 used in the manufacturing method of the compound B-1 was changed to a compound A shown in Table 3. The compound A was used in the same molar quantity as that of the compound A-1 in the manufacturing of the compound B-1.

TABLE 3

| | Compound A | Compound B |
|---|---|---|
| Manufacturing Example 11 | A-1 | B-1<br>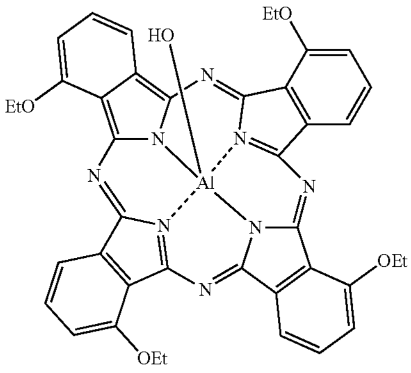 |
| Manufacturing Example 12 | A-2 | B-2<br>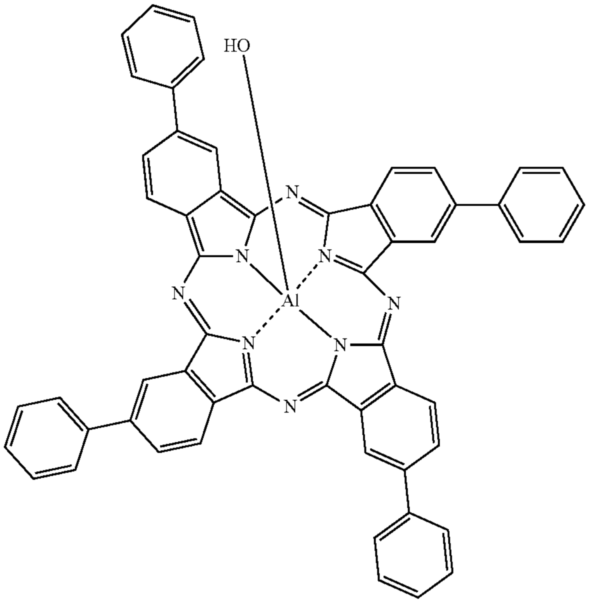 |

TABLE 3-continued
| | Compound A | Compound B |
|---|---|---|
| Manufacturing Example 13 | A-3 | B-3<br>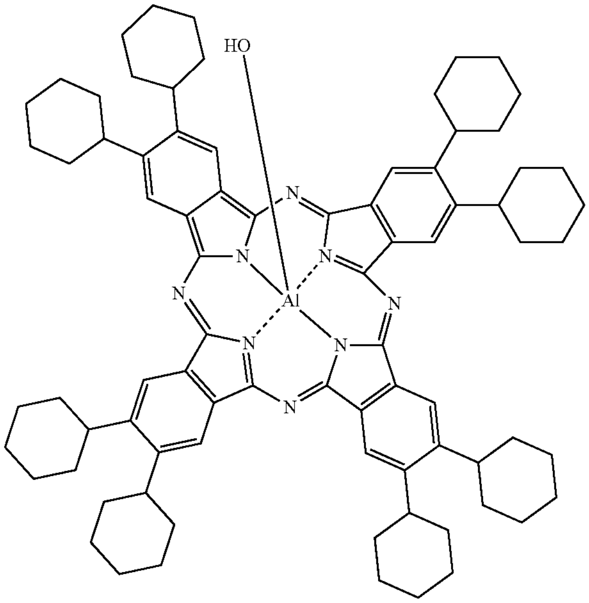 |
| Manufacturing Example 14 | A-4 | B-4<br>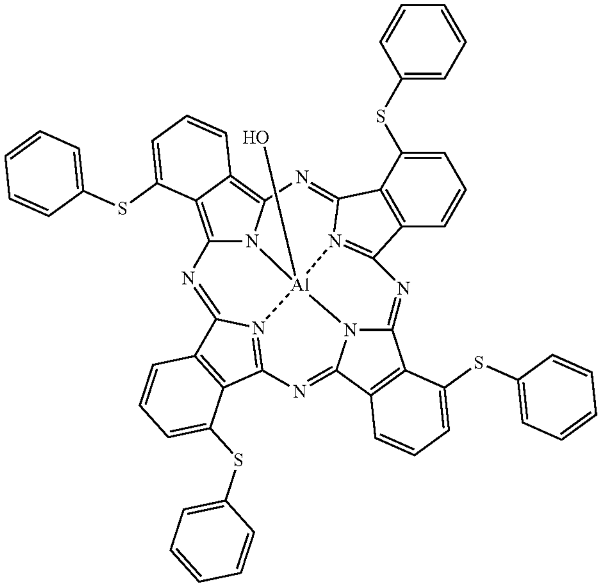 |

TABLE 3-continued

| | Compound A | Compound B |
|---|---|---|
| Manufacturing Example 15 | A-5 | B-5 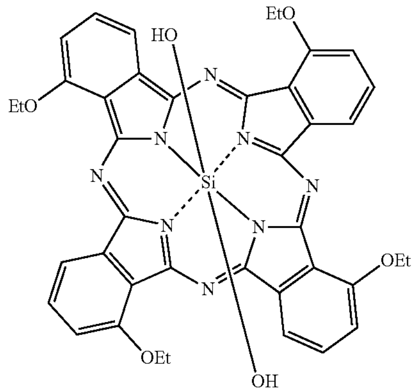 |

Manufacturing Example 16

<Manufacturing Method of Compound C-1>

An ammonia gas was introduced into a solution of 50 parts of quinoline and 1 part of anhydrous aluminum chloride, and, furthermore, 3.8 parts of 3-ethoxyphthalonitrile and 1.1 parts of 4-fluorophthalonitrile were added thereto. These components were reacted at 180° C. for seven hours. This reaction liquid is cooled to room temperature, and then 200 parts of methanol and 200 parts of a 10% hydrochloric acid aqueous solution were added thereto. Next, a precipitated solid was filtered, and the solid was washed with 200 parts of water. The washed solid (crude product) was purified using medium-pressure liquid chromatography (Smart Flash AKROS manufactured by Yamazen Corporation). The obtained purified product was dried at 80° C., thereby obtaining 1.6 parts of a compound C-1 shown in Table 4 (yield: 30.5%).

Manufacturing Examples 17 to 19

<Manufacturing Methods of Compounds C-2 to C-4>

Compounds C-2 to C-4 shown in Table 4 were each manufactured in the same manner as in the manufacturing of the compound C-1 except that anhydrous aluminum chloride used in the manufacturing method of the compound C-1 was changed to a metal source shown in Table 4. The metal source was used in the same molar quantity as that of anhydrous aluminum chloride in the manufacturing of the compound C-1.

TABLE 4

| | Metal source | Compound C |
|---|---|---|
| Manufacturing Example 16 | $AlCl_3$ | 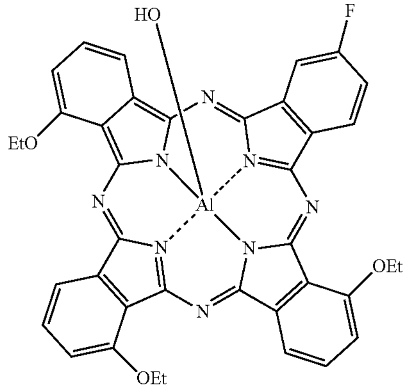 C-1 |

TABLE 4-continued

| | Metal source | Compound C |
|---|---|---|
| Manufacturing Example 17 | $SiCl_4$ | 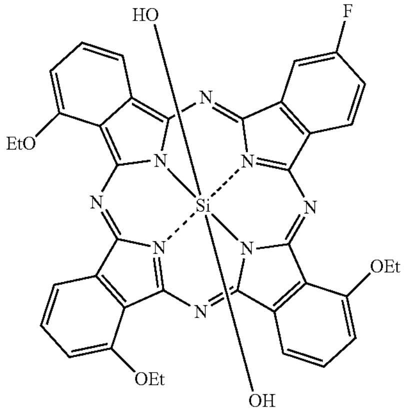 C-2 |
| Manufacturing Example 18 | $MgCl_2$ | 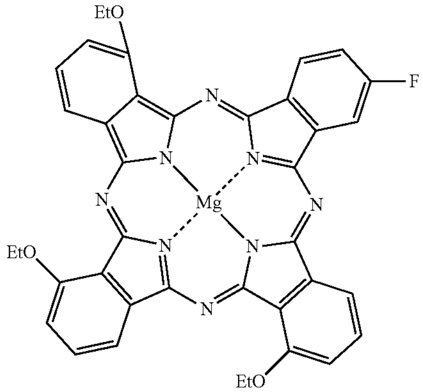 C-3 |
| Manufacturing Example 19 | $ZnCl_2$ | 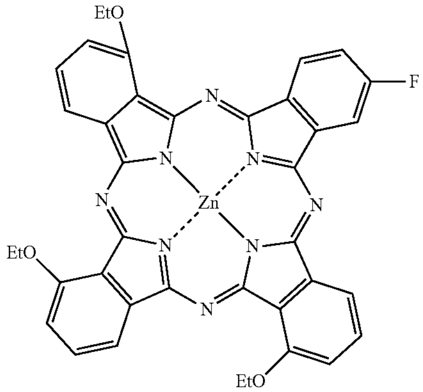 C-4 |

Example 1

<Manufacturing Method of Fluorescent Dye 1>

One part of the compound B-1 and 0.6 parts of 3-aminopropyldimethylethoxysilane were dissolved in pyridine, and this solution was refluxed at 115° C. for three hours to obtain a reaction liquid. After pyridine was removed from the reaction liquid using an evaporator, a mixed solution of 10 parts of ethanol and 50 parts of water was added thereto. Next, a precipitated solid was filtered, and the solid was washed with 50 parts of water. The washed solid was dried at 80° C., thereby obtaining 0.39 parts of a fluorescent dye 1 shown in Table 1 (yield: 33.7%). As a result of a mass analysis, a molecular ion peak was detected at m/z=848.64 (theoretical value: 847.99), and it was identified that the fluorescent dye had the structure of the fluorescent dye 1 shown in Table 1.

Examples 2 to 5

<Manufacturing Methods of Fluorescent Dyes 2 to 5>

Fluorescent dyes 2 to 5 shown in Table 1 were each manufactured in the same manner as in the manufacturing of the fluorescent dye 1 except that the compound B-1 used in the manufacturing method of the fluorescent dye 1 was changed to a compound B shown in Table 5. The compound B was used in the same molar quantity as that of the compound B-1 in the manufacturing of the fluorescent dye 1. The structures of the obtained fluorescent dyes 2 to 5 were identified by mass analyses, and it was confirmed that the fluorescent dyes had a structure shown in Table 1. Table 11 shows the analysis results of mass spectra.

TABLE 5

| | Fluorescent dye | Compound B |
|---|---|---|
| Example 1 | Fluorescent dye 1 | B-1 |
| Example 2 | Fluorescent dye 2 | B-2 |
| Example 3 | Fluorescent dye 3 | B-3 |
| Example 4 | Fluorescent dye 4 | B-4 |
| Example 5 | Fluorescent dye 5 | B-5 |

Example 6

<Manufacturing Method of Fluorescent Dye 6>

0.7 Parts of the compound A-1 and 0.4 parts of 4-(3-aminopropyl)benzenesulfonic acid were dissolved in 50 parts of dimethyl sulfoxide, furthermore, 0.3 parts of 1,8-diazabicyclo[5.4.0]-7-undecene was added thereto, and these components were reacted at 90° C. for five hours. This reaction liquid is cooled to room temperature, and then 100 parts of water and 10 parts of common salt were added thereto. Next, a precipitated solid was filtered, and the solid was washed with 50 parts of water. The washed solid was dried at 80° C., thereby obtaining 0.36 parts of a fluorescent dye 6 shown in Table 1 (yield: 41.6%). As a result of a mass analysis, a molecular ion peak was detected at m/z=916.57 (theoretical value: 915.96), and it was identified that the fluorescent dye had the structure of the fluorescent dye 6 shown in Table 1.

Examples 7 to 14

<Manufacturing Methods of Fluorescent Dyes 7 to 14>

Fluorescent dyes 7 to 14 shown in Table 1 were each manufactured in the same manner as in the manufacturing of the fluorescent dye 6 except that the compound A-1 and 4-(3-aminopropyl)benzenesulfonic acid used in the manufacturing method of the fluorescent dye 6 were changed to a compound A and an acidic compound shown in Table 6. The compound A and the acidic compound were used in the same molar quantities as those of the compound A-1 and 4-(3-aminopropyl)benzenesulfonic acid in the manufacturing of the fluorescent dye 6, respectively. The structures of the obtained fluorescent dyes 7 to 14 were identified by mass analyses, and it was confirmed that the fluorescent dyes had a structure shown in Table 1. Table 11 shows the analysis results of mass spectra.

TABLE 6

| | Fluorescent dye | Compound A | Acidic compound |
|---|---|---|---|
| Example 6 | Fluorescent dye 6 | A-1 | 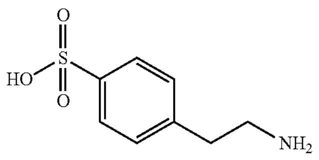 |
| Example 7 | Fluorescent dye 7 | A-6 | 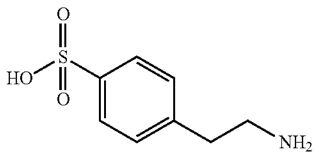 |
| Example 8 | Fluorescent dye 8 | A-7 | 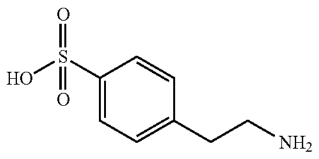 [SMILES: NCCc1ccc(S(=O)(=O)O)cc1] |
| Example 9 | Fluorescent dye 9 | A-8 | 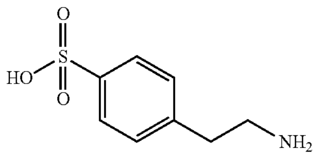 [SMILES: NCCc1ccc(S(=O)(=O)O)cc1] |
| Example 10 | Fluorescent dye 10 | A-1 | 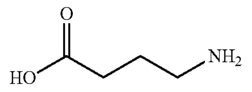 |
| Example 11 | Fluorescent dye 11 | A-1 | 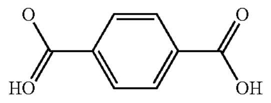 [SMILES: O=C(O)c1ccc(C(=O)O)cc1] |

TABLE 6-continued

| | Fluorescent dye | Compound A | Acidic compound |
|---|---|---|---|
| Example 12 | Fluorescent dye 12 | A-9 | 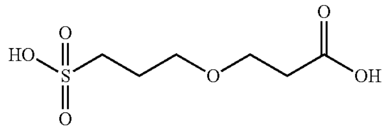 [SMILES: O=C(O)CCOCCCS(=O)(=O)O] |
| Example 13 | Fluorescent dye 13 | A-10 | 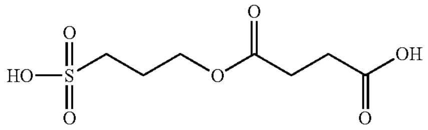 [SMILES: O=C(O)CCC(=O)OCCCS(=O)(=O)O] |
| Example 14 | Fluorescent dye 14 | A-1 | 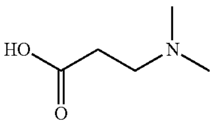 |

Example 15

<Manufacturing Method of Fluorescent Dye 15>

0.5 Parts of the compound A-1 and 0.29 parts of (2-carboxyethyl)phenylphosphinic acid were dissolved in 20 parts of dimethyl sulfoxide, and this solution was reacted at 80° C. for eight hours. This reaction liquid is cooled to room temperature, and then 50 parts of water and 10 parts of common salt were added thereto. Next, a precipitated solid was filtered, and the solid was washed with 50 parts of water. The washed solid was dried at 80° C., thereby obtaining 0.46 parts of a fluorescent dye 15 shown in Table 1 (yield: 74.4%). As a result of a mass analysis, a molecular ion peak was detected at m/z=929.46 (theoretical value: 928.88), and it was identified that the fluorescent dye had the structure of the fluorescent dye 15 shown in Table 1.

Examples 16 to 18

<Manufacturing Methods of Fluorescent Dyes 16 to 18>

Fluorescent dyes 16 to 18 shown in Table 1 were each manufactured in the same manner as in the manufacturing of the fluorescent dye 15 except that the compound A-1 and (2-carboxyethyl)phenylphosphinic acid used in the manufacturing method of the fluorescent dye 15 were changed to a compound A and an acidic compound shown in Table 7. The compound A and the acidic compound were used in the same molar quantities as those of the compound A-1 and (2-carboxyethyl)phenylphosphinic acid in the manufacturing of the fluorescent dye 15, respectively. The structures of the obtained fluorescent dyes 16 to 18 were identified by mass analyses, and it was confirmed that the fluorescent dyes had a structure shown in Table 1. Table 11 shows the analysis results of mass spectra.

TABLE 7

| | Fluorescent dye | Compound A | Acidic compound |
|---|---|---|---|
| Example 15 | Fluorescent dye 15 | A-1 | 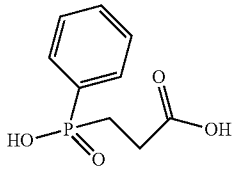 [SMILES: O=C(O)CCP(=O)(O)c1ccccc1] |
| Example 16 | Fluorescent dye 16 | A-5 | 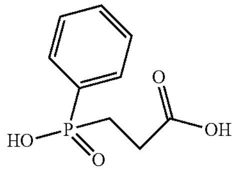 [SMILES: O=C(O)CCP(=O)(O)c1ccccc1] |
| Example 17 | Fluorescent dye 17 | A-1 | 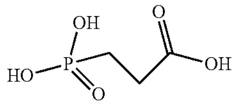 |

TABLE 7-continued

| | Fluorescent dye | Compound A | Acidic compound |
|---|---|---|---|
| Example 18 | Fluorescent dye 18 | A-1 | 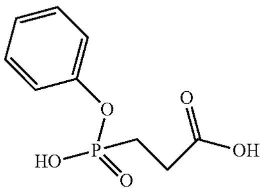 [SMILES: O=C(O)CCP(=O)(O)Oc1ccccc1] |

Example 19

<Manufacturing Method of Fluorescent Dye 19>

0.5 Parts of the fluorescent dye 1, 0.8 parts of methyl iodide, and 0.8 parts of potassium carbonate were dissolved in 50 parts of tetrahydrofuran, and this solution was reacted at 25° C. for five hours. After tetrahydrofuran was removed from the reaction liquid using an evaporator, 20 parts of tetrahydrofuran and 60 parts of water were added thereto. Next, a precipitated solid was filtered, and the solid was washed with 60 parts of water. The washed solid was dried at 80° C., thereby obtaining 0.21 parts of a fluorescent dye 19 shown in Table 1 (yield: 33.3%). As a result of a mass analysis, a molecular ion peak was detected at m/z (positive) =892.25 (theoretical value: 891.08), and it was identified that the fluorescent dye had the structure of the fluorescent dye 19 shown in Table 1.

Examples 20 to 23

<Manufacturing Methods of Fluorescent Dyes 20 to 23>

Fluorescent dyes 20 to 23 shown in Table 1 were each manufactured in the same manner as in the manufacturing of the fluorescent dye 19 except that methyl iodide and the fluorescent dye 1 used in the manufacturing method of the fluorescent dye 19 were changed to an iodized compound and an amine shown in Table 8. The iodized compound and the amine were used in the same molar quantities as those of methyl iodide and the fluorescent dye 1 in the manufacturing of the fluorescent dye 19, respectively. The structures of the obtained fluorescent dyes 20 to 23 were identified by mass analyses, and it was confirmed that the fluorescent dyes had a structure shown in Table 1. Table 11 shows the analysis results of mass spectra.

TABLE 8

| | Fluorescent dye | Iodized compound | Amines |
|---|---|---|---|
| Example 19 | Fluorescent dye 19 | $CH_3I$ | Fluorescent dye 1 |
| Example 20 | Fluorescent dye 20 | $C_2H_4I$ | Fluorescent dye 2 |
| Example 21 | Fluorescent dye 21 | 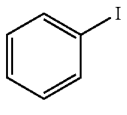 | Fluorescent dye 3 |
| Example 22 | Fluorescent dye 22 | $C_{18}H_{37}I$ | Fluorescent dye 4 |
| Example 23 | Fluorescent dye 23 | $CH_3I$ | Fluorescent dye 5 |

Example 24

<Manufacturing Method of Fluorescent Dye 24>

0.06 Parts of the fluorescent dye 1 and 0.007 parts of succinic anhydride were dissolved in 5 parts of N-methyl-2-pyrrolidone (NMP), and this solution was reacted at 90° C. for four hours. After NMP was removed from the reaction liquid using a centrifugal evaporator, 5 parts of water was added thereto. Next, a precipitated solid was filtered, and the solid was washed with 5 parts of water. The washed solid was dried at 80° C., thereby obtaining 0.041 parts of a fluorescent dye 24 shown in Table 1 (yield: 61.1%). As a result of a mass analysis, a molecular ion peak was detected at m/z=949.07 (theoretical value: 948.06), and it was identified that the fluorescent dye had the structure of the fluorescent dye 24 shown in Table 1.

Examples 25 to 30

<Manufacturing Methods of Fluorescent Dyes 25 to 30>

Fluorescent dyes 25 to 30 shown in Table 1 were each manufactured in the same manner as in the manufacturing of the fluorescent dye 24 except that succinic anhydride and the fluorescent dye 1 used in the manufacturing method of the fluorescent dye 24 were changed to a succinic anhydride derivative and an amine shown in Table 9. The succinic anhydride derivative and the amine were used in the same molar quantities as those of succinic anhydride and the fluorescent dye 1 in the manufacturing of the fluorescent dye 24, respectively. The structures of the obtained fluorescent dyes 25 to 30 were identified by mass analyses, and it was confirmed that the fluorescent dyes had a structure shown in Table 1. Table 11 shows the analysis results of mass spectra.

TABLE 9

| | Fluorescent dye | Succinic anhydride derivative | Amines |
|---|---|---|---|
| Example 24 | Fluorescent dye 24 | 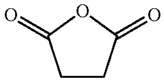 | Fluorescent dye 1 |
| Example 25 | Fluorescent dye 25 | 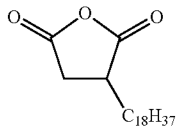 | Fluorescent dye 1 |
| Example 26 | Fluorescent dye 26 | 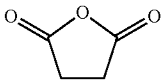 | Fluorescent dye 6 |

TABLE 9-continued

| | Fluorescent dye | Succinic anhydride derivative | Amines |
|---|---|---|---|
| Example 27 | Fluorescent dye 27 | 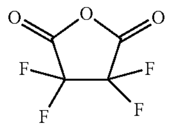 [SMILES: O=C1OC(=O)C(F)(F)C1(F)F] | Fluorescent dye 7 |
| Example 28 | Fluorescent dye 28 | 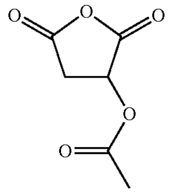 | Fluorescent dye 8 |
| Example 29 | Fluorescent dye 29 | 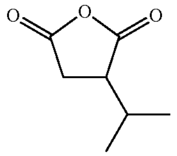 | Fluorescent dye 9 |
| Example 30 | Fluorescent dye 30 | 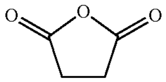 | Fluorescent dye 10 |

Example 31

<Manufacturing Method of Fluorescent Dye 31>

1.0 Part of the compound C-1 and 0.6 parts of (2-carboxyethyl)phenylphosphinic acid were dissolved in 50 parts of dimethyl sulfoxide, furthermore. 0.4 parts of 1,8-diazabicyclo[5.4.0]-7-undecene was added thereto, and then this solution was reacted at 90° C. for eight hours. This reaction liquid is cooled to room temperature, and then 100 parts of water was added thereto. Next, a precipitated solid was filtered, and the solid was washed with 50 parts of water. The obtained solid (crude product) was purified using medium-pressure liquid chromatography (Smart Flash AKROS manufactured by Yamazen Corporation). The obtained purified product was dried at 80° C., thereby obtaining 0.72 parts of a fluorescent dye 31 shown in Table 1 (yield: 60.1%). As a result of a mass analysis, a molecular ion peak was detected at m/z=901.46 (theoretical value: 900.82), and it was identified that the fluorescent dye had the structure of the fluorescent dye 31 shown in Table 1.

Examples 32 to 37

<Manufacturing Methods of Fluorescent Dyes 32 to 37>

Fluorescent dyes 32 to 37 shown in Table 1 were each manufactured in the same manner as in the manufacturing of the fluorescent dye 31 except that the compound C-1 and (2-carboxyethyl)phenylphosphinic acid used in the manufacturing method of the fluorescent dye 31 were changed to a compound C and an acidic compound shown in Table 10. The compound C and the acidic compound were used in the same molar quantities as those of the compound C-1 and (2-carboxyethyl)phenylphosphinic acid in the manufacturing of the fluorescent dye 31, respectively. The structures of the obtained fluorescent dyes 32 to 37 were identified by mass analyses, and it was confirmed that the fluorescent dyes had a structure shown in Table 1. Table 11 shows the analysis results of mass spectra.

TABLE 10

| | Fluorescent dye | Comound C | Acidic compound |
|---|---|---|---|
| Example 31 | Fluorescent dye 31 | C-1 | 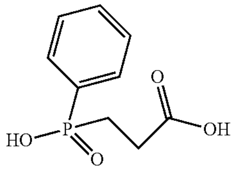 [SMILES: O=C(O)CCP(=O)(O)c1ccccc1] |
| Example 32 | Fluorescent dye 32 | C-1 | 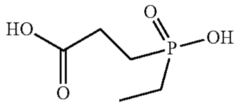 |
| Example 33 | Fluorescent dye 33 | C-1 | 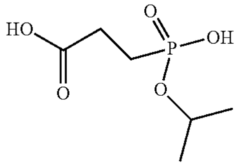 |
| Example 34 | Fluorescent dye 34 | C-2 | 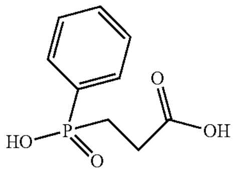 |

TABLE 10-continued

| | Fluorescent dye | Comound C | Acidic compound |
|---|---|---|---|
| Example 35 | Fluorescent dye 35 | C-1 | 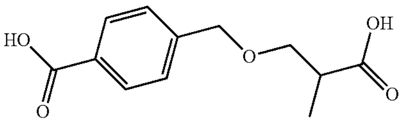 [SMILES: CC(COCc1ccc(C(=O)O)cc1)C(=O)O] |
| Example 36 | Fluorescent dye 36 | C-3 | 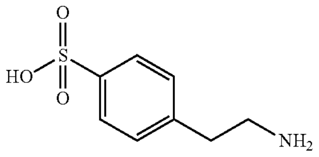 [SMILES: NCCc1ccc(S(=O)(=O)O)cc1] |
| Example 37 | Fluorescent dye 37 | C-4 | 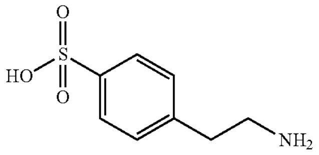 [SMILES: NCCc1ccc(S(=O)(=O)O)cc1] |

Example 38

<Manufacturing Method of Fluorescent Dye 38>

1.0 Part of Pigment RED 255, which is a diketopyrrolopyrrole-based dye, (manufactured by Tokyo Chemical Industry Co., Ltd.), 0.6 parts of 4-bromobutyric acid, and 0.1 parts of sodium hydroxide (60%) were dissolved in 50 parts of N,N-dimethyl formamide, and this solution was reacted at 90° C. for four hours. This reaction liquid is cooled to room temperature, and then 100 parts of water was added thereto. Next, a precipitated solid was filtered, and the solid was washed with 50 parts of water. The washed solid (crude product) was purified using medium-pressure liquid chromatography (Smart Flash AKROS manufactured by Yamazen Corporation). The obtained purified product was dried at 80° C., thereby obtaining 0.70 parts of a fluorescent dye 38 shown in Table 1 (yield: 53.9%). As a result of a mass analysis, a molecular ion peak was detected at m/z=375.28 (theoretical value: 374.40), and it was identified that the fluorescent dye had the structure of the fluorescent dye 38 shown in Table 1.

Example 39

<Manufacturing Method of Fluorescent Dye 39>

1.0 Part of 5-carboxyfluorescein (manufactured by Tokyo Chemical Industry Co., Ltd.), 0.3 parts of N,N-dimethyl-1,3-propanediamine, and 0.1 parts of para-toluenesulfonic acid were dissolved in 50 parts of xylene, and this solution was reacted at 140° C. for 24 hours. After this reaction liquid was cooled to room temperature, xylene was removed from the reaction liquid using an evaporator, and 50 parts of a petroleum ether was added thereto. Next, an insoluble matter was removed by suction filtration, and then the petroleum ether was removed using an evaporator, thereby obtaining a solid. This solid was dried at 80° C., thereby obtaining 0.57 parts of a fluorescent dye 39 shown in Table 1 (yield: 46.6%). As a result of a mass analysis, a molecular ion peak was detected at m/z=461.37 (theoretical value: 460.49), and it was identified that the fluorescent dye had the structure of the fluorescent dye 39 shown in Table 1.

Example 40

<Manufacturing Method of Fluorescent Dye 40>

1.0 Part of Rhodamin B (manufactured by Tokyo Chemical Industry Co., Ltd.), 0.2 parts of N,N-dimethyl-1,3-propanediamine, and 0.1 parts of para-toluenesulfonic acid were dissolved in 50 parts of xylene, and this solution was reacted at 140° C. for 24 hours. After this reaction liquid was cooled to room temperature, xylene was removed from the reaction liquid using an evaporator, and 50 parts of a petroleum ether was added thereto. Next, an insoluble matter was removed by suction filtration, and then the petroleum ether was removed using an evaporator, thereby obtaining a solid. This solid was dried at 80° C., thereby obtaining 0.46 parts of a fluorescent dye 40 shown in Table 1 (yield: 39.1%). As a result of a mass analysis, a molecular ion peak was detected at m/z=564.02 (theoretical value: 563.18), and it was identified that the fluorescent dye had the structure of the fluorescent dye 40 shown in Table 1.

Example 41

<Manufacturing Method of Fluorescent Dye 41>

1.0 Part of BDPFL, which is a BODIPY-based dye, (manufactured by Tokyo Chemical Industry Co., Ltd.) and 0.3 parts of N,N-dimethyl-1,3-propanediamine were dissolved in 50 parts of xylene, and this solution was reacted at 140° C. for 24 hours. After this reaction liquid was cooled to room temperature, xylene was removed from the reaction liquid using an evaporator, and 50 parts of a petroleum ether was added thereto. Next, an insoluble matter was removed by suction filtration, and then the petroleum ether was removed using an evaporator, thereby obtaining a solid. This solid was dried at 80° C., thereby obtaining 0.38 parts of a fluorescent dye 41 shown in Table 1 (yield: 29.3%). As a result of a mass analysis, a molecular ion peak was detected at m/z=379.11 (theoretical value: 378.27), and it was identified that the fluorescent dye had the structure of the fluorescent dye 41 shown in Table 1.

TABLE 11

| | Theoretical value | Measurement value |
|---|---|---|
| Fluorescent dye 1 | 847.99 | 848.64 |
| Fluorescent dye 2 | 976.17 | 976.98 |
| Fluorescent dye 3 | 1328.94 | 1329.51 |
| Fluorescent dye 4 | 1104.41 | 1105.66 |
| Fluorescent dye 5 | 866.10 | 867.34 |
| Fluorescent dye 6 | 915.96 | 916.57 |
| Fluorescent dye 7 | 1011.74 | 1012.79 |
| Fluorescent dye 8 | 1749.69 | 1750.47 |
| Fluorescent dye 9 | 964.18 | 965.32 |
| Fluorescent dye 10 | 817.84 | 818.46 |
| Fluorescent dye 11 | 880.85 | 880.67 |
| Fluorescent dye 12 | 1207.48 | 1208.41 |
| Fluorescent dye 13 | 1075.05 | 1075.94 |
| Fluorescent dye 14 | 831.87 | 832.76 |
| Fluorescent dye 15 | 928.88 | 929.46 |
| Fluorescent dye 16 | 946.99 | 947.99 |
| Fluorescent dye 17 | 868.78 | 869.74 |
| Fluorescent dye 18 | 944.88 | 945.61 |
| Fluorescent dye 19 | 891.08 | 892.25 |
| Fluorescent dye 20 | 1061.34 | 1062.57 |
| Fluorescent dye 21 | 1558.24 | 1559.08 |
| Fluorescent dye 22 | 1862.87 | 1863.71 |
| Fluorescent dye 23 | 909.19 | 909.89 |
| Fluorescent dye 24 | 948.06 | 949.07 |
| Fluorescent dye 25 | 1200.55 | 1201.47 |
| Fluorescent dye 26 | 1016.03 | 1017.08 |
| Fluorescent dye 27 | 1183.78 | 1184.55 |
| Fluorescent dye 28 | 1907.80 | 1908.78 |
| Fluorescent dye 29 | 1106.34 | 1107.22 |
| Fluorescent dye 30 | 917.92 | 918.97 |
| Fluorescent dye 31 | 900.82 | 901.46 |
| Fluorescent dye 32 | 852.78 | 853.63 |
| Fluorescent dye 33 | 882.81 | 883.75 |
| Fluorescent dye 34 | 918.93 | 919.61 |
| Fluorescent dye 35 | 924.91 | 925.30 |
| Fluorescent dye 36 | 882.25 | 883.10 |

TABLE 11-continued

| | Theoretical value | Measurement value |
|---|---|---|
| Fluorescent dye 37 | 923.33 | 924.46 |
| Fluorescent dye 38 | 374.40 | 375.28 |
| Fluorescent dye 39 | 460.49 | 461.37 |
| Fluorescent dye 40 | 563.18 | 564.02 |
| Fluorescent dye 41 | 378.27 | 379.11 |

Manufacturing Example 20

<Manufacturing Method of Compound A-11>

An ammonia gas was introduced into a solution of 50 parts of quinoline and 1 part of anhydrous aluminum chloride, furthermore, 5 parts of 3,6-bis(phenylthio)phthalonitrile was added thereto, and these components were reacted at 180° C. for seven hours. This reaction liquid is cooled to room temperature, and then 200 parts of methanol and 200 parts of a 10% hydrochloric acid aqueous solution were added thereto. Next, a precipitated solid was filtered, and the solid was washed with 200 parts of water. The washed solid was dried at 80° C., thereby obtaining a compound A-11 shown in Table 12 (yield: 72.8%).

Manufacturing Examples 21 and 22

<Manufacturing Methods of Compounds A-12 and A-13>

Compounds A-12 and A-13 shown in Table 12 were each manufactured in the same manner as in the manufacturing of the compound A-11 except that 3,6-bis(phenylthio)phthalonitrile used in the manufacturing method of the compound A-11 was changed to a phthalonitrile derivative shown in Table 12. The phthalonitrile derivative was used in the same molar quantity as that of 3,6-bis(phenylthio)phthalonitrile in the manufacturing of the compound A-11.

TABLE 12

| | Phthalonitrile derivative | Compound A |
|---|---|---|
| Manufacturing Example 20 | 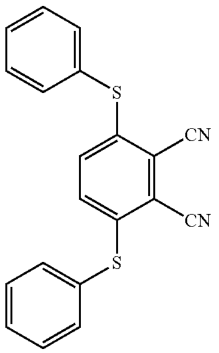 [SMILES: N#Cc1c(Sc2ccccc2)ccc(Sc2ccccc2)c1C#N] | 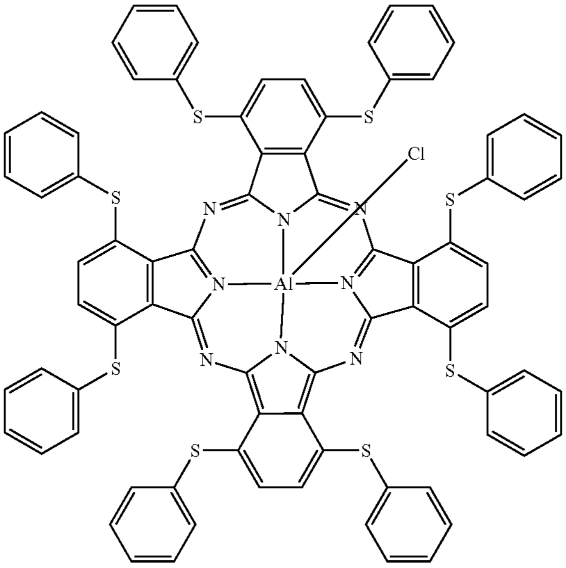 A-11 |

TABLE 12-continued

| | Phthalonitrile derivative | Compound A |
|---|---|---|
| Manufacturing Example 21 | 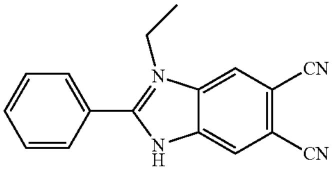 | 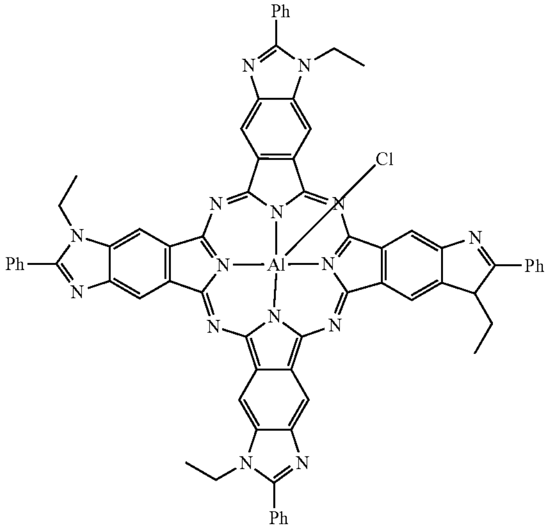<br>A-13 |
| Manufacturing Example 22 | 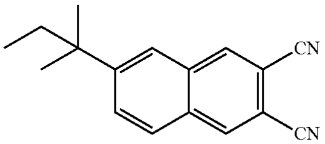 [SMILES: CCC(C)(C)c1ccc2cc(C#N)c(C#N)cc2c1] | 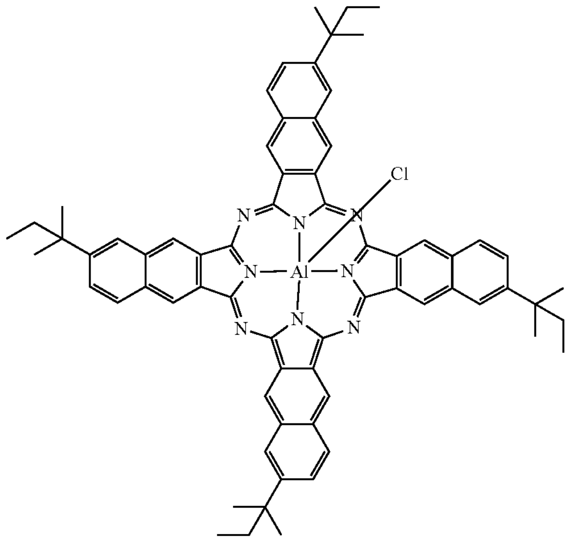<br>A-13 |

Example 42

<Manufacturing Method of Fluorescent Dye 42>

0.7 Parts of the compound A-1 and 0.4 parts of 1,2-ethylenediphosphonic acid were dissolved in 50 parts of dimethyl sulfoxide, furthermore, 0.3 parts of 1,8-diazabicyclo[5.4.0]-7-undecene was added thereto, and then this solution was reacted at 90° C. for five hours. This reaction liquid is cooled to room temperature, and then 100 parts of water and 10 parts of common salt were added thereto. Next, a precipitated solid was filtered, and the solid was washed with 50 parts of water. The washed solid was dried at 80° C., thereby obtaining 0.42 parts of a fluorescent dye 42 shown in Table 1 (yield: 50.6%). As a result of a mass analysis, a molecular ion peak was detected at m/z=905.35 (theoretical value: 905.21), and it was identified that the fluorescent dye had the structure of the fluorescent dye 42 shown in Table 1.

Examples 43 to 55

<Manufacturing Methods of Fluorescent Dyes 43 to 55>

Fluorescent dyes 43 to 55 shown in Table 1 were each manufactured in the same manner as in the manufacturing of the fluorescent dye 6 except that the compound A-1 and 1,2-ethylenediphosphonic acid used in the manufacturing method of the fluorescent dye 1 were changed to a compound A and an axial ligand shown in Table 13. The compound A and the axial ligand were used in the same molar quantities as those of the compound A-1 and 1,2-ethylenediphosphonic acid in the manufacturing of the fluorescent dye 42, respectively. The structures of the obtained fluorescent dyes 43 to 55 were identified by analyses using a mass analyzer, and it was confirmed that the fluorescent dyes had a structure shown in Table 1. Table 13 showed the analysis results of mass spectra.

TABLE 13-1

| | Axial ligand | Compound A | Fluorescent dye | MALDI-TOF-MS [M + H]$^+$ |
|---|---|---|---|---|
| Example 42 | 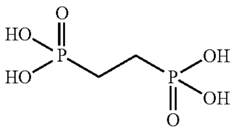 | A-1 | Fluorescent dye 42 | Theoretical value: 905.21 Actually measured value: 905.35 |
| Example 43 | 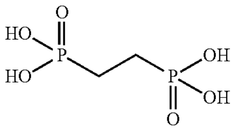 | A-3 | Fluorescent dye 43 | Theoretical value: 1383.73 Actually measured value: 1383.55 |
| Example 44 | 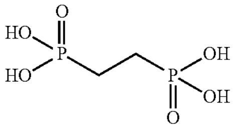 | A-11 | Fluorescent dye 44 | Theoretical value: 953.35 Actually measured value: 953.00 |
| Example 45 | 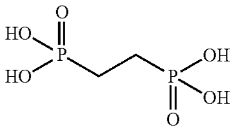 | A-8 | Fluorescent dye 45 | Theoretical value: 1593.13 Actually measured value: 1592.98 |
| Example 46 | 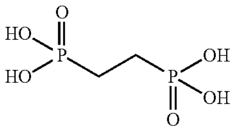 | A-12 | Fluorescent dye 46 | Theoretical value: 1305.38 Actually measured value: 1305.57 |

TABLE 13-2

| | Axial ligand | Compound A | Fluorescent dye | MALDI-TOF-MS [M + H]$^+$ |
|---|---|---|---|---|
| Example 47 | 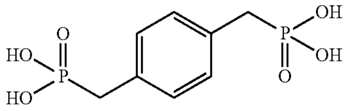 [SMILES: O=P(O)(O)Cc1ccc(CP(=O)(O)O)cc1] | A-1 | Fluorescent dye 47 | Theoretical value: 981.24 Actually measured value: 981.02 |
| Example 48 | 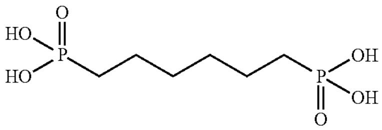 [SMILES: O=P(O)(O)CCCCCCP(=O)(O)O] | A-1 | Fluorescent dye 48 | Theoretical value: 961.27 Actually measured value: 961.28 |
| Example 49 | 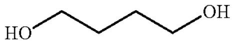 | A-1 | Fluorescent dye 49 | Theoretical value: 805.30 Actually measured value: 805.11 |
| Example 50 | 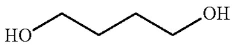 | A-6 | Fluorescent dye 50 | Theoretical value: 901.14 Actually measured value: 901.43 |
| Example 51 | 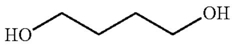 | A-10 | Fluorescent dye 51 | Theoretical value: 1277.55 Actually measured value: 1277.13 |

TABLE 13-3

| | Axial ligand | Compound A | Fluorescent dye | MALDI-TOF-MS [M + H]$^+$ |
|---|---|---|---|---|
| Example 52 | 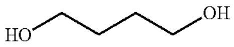 | A-13 | Fluorescent dye 52 | Theoretical value: 1109.57 Actually measured value: 1109.83 |

TABLE 13-3-continued

| | Axial ligand | Compound A | Fluorescent dye | MALDI-TOF-MS [M + H]$^+$ |
|---|---|---|---|---|
| Example 53 | 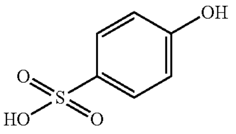 [SMILES: O=S(=O)(O)c1ccc(O)cc1] | A-1 | Fluorescent dye 53 | Theoretical value: 889.24<br>Actually measured value: 889.81 |
| Example 54 | 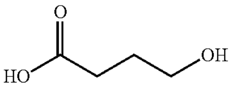 | A-1 | Fluorescent dye 54 | Theoretical value: 819.28<br>Actually measured value: 819.83 |
| Example 55 | 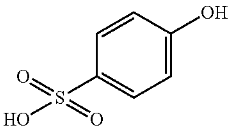 [SMILES: O=S(=O)(O)c1ccc(O)cc1] | A-1 | Fluorescent dye 55 | Theoretical value: 889.23<br>Actually measured value: 889.55 |

Manufacturing Example 23

<Manufacturing of Compound D-1>

Five parts of 4-butylthio-1,3-diiminoisoindoline and 8.8 parts of silicon tetrachloride were added to 200 parts of sulfolane and 15.7 parts of 1,8-diazabicyclo[5,4,0]-7-undecene (DBU), and these components were heated and stirred at 160° C. to 170° C. for eight hours. Next, the reaction liquid was cooled to room temperature (25° C.), and 200 parts of methanol was added thereto. Next, the precipitated deposit (solid) was filtered, the solid was washed with a mixed solution of methanol and water (mass ratio=4:1) and then dried, thereby obtaining 2.6 parts of a compound D-1 shown in Table 14 (yield: 63.6%). As a result of a mass analysis, a molecular ion peak was detected at m/z=751.65 (theoretical value: 751.24), and it was confirmed that the compound had the structure of the compound D-1 shown in Table 14.

TABLE 14

| | Isoindoline derivative | Compound D |
|---|---|---|
| Manufacturing Example 23 | 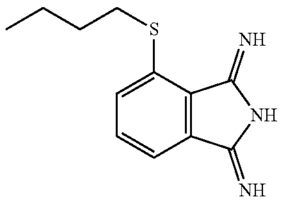 [SMILES: CCCCSc1cccc2c1C(=N)NC2=N] | 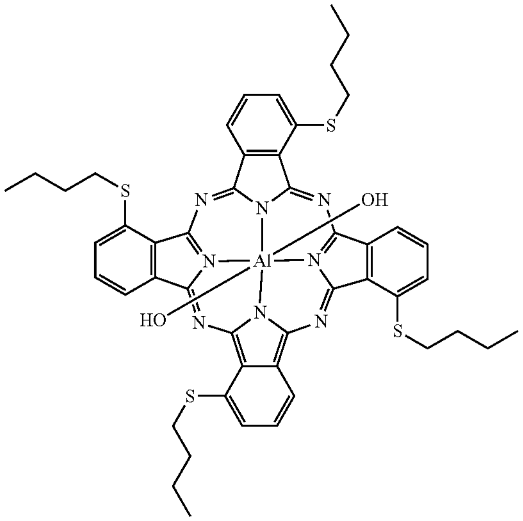<br>D-1 |

Example 56

<Manufacturing Method of Fluorescent Dye 56>

1.0 Part of the compound B-5 and 0.5 parts of 1,2-ethylenediphosphonic acid were dissolved in 50 parts of dimethyl sulfoxide, furthermore, 0.3 parts of 1,8-diazabicyclo[5.4.0]-7-undecene was added thereto, and these were reacted at 90° C. for five hours. This reaction liquid is cooled to room temperature, and then 100 parts of water and 10 parts of common salt were added thereto. Next, a precipitated solid was filtered, and the solid was washed with 50 parts of water. The washed solid was dried at 80° C., thereby obtaining 0.52 parts of a fluorescent dye 1 shown in Table 1 (yield: 42.3%). As a result of a mass analysis, a molecular ion peak was detected at m/z=923.47 (theoretical value: 923.21), and it was identified that the fluorescent dye had the structure of the fluorescent dye 56 shown in Table 1.

Example 57

<Manufacturing Method of Fluorescent Dye 57>

A fluorescent dye 57 shown in Table 1 was manufactured in the same manner as in the manufacturing of the fluorescent dye 56 except that the compound B-5 used in the manufacturing method of the fluorescent dye 1 was changed to compound D-1. The compound D-1 was used in the same molar quantity as that of the compound B-5 in the manufacturing of the fluorescent dye 56. The structure of the obtained fluorescent dye 57 was identified by analyses using a mass analyzer, and it was confirmed that the fluorescent dyes had a structure shown in Table 1. Table 15 showed the analysis results of mass spectra.

TABLE 15

| | Axial ligand | Compound B or D | Fluorescent dye | MALDI-TOF-MS[M + H]$^+$ |
|---|---|---|---|---|
| Example 56 | 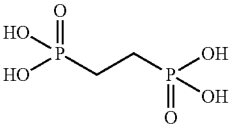 | B-5 | Fluorescent dye 56 | Theoretical value: 923.21 Actually measured value: 923.47 |
| Example 57 | 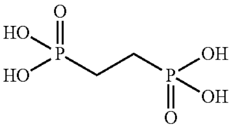 | D-1 | Fluorescent dye 57 | Theoretical value: 1099.24 Actually measured value: 1099.85 |

Example 58

<Manufacturing Method of Fluorescent Dye 58>

0.7 Parts of the compound C-3 and 0.7 parts of 1,2-hexylenediphosphonic acid were dissolved in 50 parts of dimethyl sulfoxide, furthermore, 0.3 parts of 1,8-diazabicyclo[5.4.0]-7-undecene was added to this solution, and these were reacted at 90° C. for five hours. This reaction liquid is cooled to room temperature, and then 100 parts of water and 10 parts of common salt were added thereto. Next, a precipitated solid was filtered, and the solid was washed with 50 parts of water. The washed solid was dried at 80° C., thereby obtaining 0.39 parts of a fluorescent dye 1 shown in Table 1 (yield: 42.3%). As a result of a mass analysis, a molecular ion peak was detected at m/z=913.66 (theoretical value: 913.24), and it was identified that the fluorescent dye had the structure of the fluorescent dye 58 shown in Table 1.

Example 59

<Manufacturing Method of Fluorescent Dye 59>

A fluorescent dye 59 shown in Table 1 was manufactured in the same manner as in the manufacturing of the fluorescent dye 58 except that the compound C-3 and 1,2-hexylenediphosphonic acid used in the manufacturing method of the fluorescent dye 58 were changed to a compound C-4 and a ring substituent shown in Table 16. The compound C-4 was used in the same molar quantity as that of the compound C-3 in the manufacturing of the fluorescent dye 17. The structure of the obtained fluorescent dye 59 was identified by analyses using a mass analyzer, and it was confirmed that the fluorescent dyes had a structure shown in Table 1. Table 16 showed the analysis results of mass spectra.

Example 60

<Manufacturing Method of Fluorescent Dye 60>

1.0 Part of Pigment RED 255, which is a diketopyrrolopyrrole-based dye, (Tokyo Chemical Industry Co., Ltd.), 0.6 parts of 3-aminopropylphosphonic acid, and 0.1 parts of sodium hydroxide (60% dispersion) were dissolved in 50 parts of N,N-dimethyl formamide, and this solution was reacted at 90° C. for four hours. This reaction liquid is cooled to room temperature, and then 100 parts of water was added thereto. Next, a precipitated solid was filtered, and the solid was washed with 50 parts of water. The washed solid (crude product) was purified using medium-pressure liquid chromatography (Smart Flash AKROS manufactured by Yamazen Corporation). The obtained purified product was dried at 80° C., thereby obtaining 0.65 parts of a fluorescent dye 60 shown in Table 1 (yield: 45.5%). As a result of a mass analysis, a molecular ion peak was detected at m/z=411.52 (theoretical value: 411.10), and it was identified that the fluorescent dye had the structure of the fluorescent dye 60 shown in Table 1.

Example 61

<Manufacturing Method of Fluorescent Dye 61>

1.0 Part of 5-carboxyfluorescein (Tokyo Chemical Industry Co., Ltd.), 0.7 parts of 3-aminopropylphosphonic acid, and 0.1 parts of para-toluenesulfonic acid were dissolved in 50 parts of xylene, and this solution was reacted at 140° C. for 24 hours. After this reaction liquid was cooled to room temperature, xylene was removed from the reaction liquid using an evaporator, and 50 parts of a petroleum ether was added thereto. Next, an insoluble matter was removed by suction filtration, and then the petroleum ether was removed using an evaporator, thereby obtaining a solid. This solid was dried at 80° C., thereby obtaining 0.75 parts of a fluorescent dye 61 shown in Table 1 (yield: 51.2%). As a result of a mass analysis, a molecular ion peak was detected at m/z=551.02 (theoretical value: 551.18), and it was identified that the fluorescent dye had the structure of the fluorescent dye 61 shown in Table 1.

TABLE 16

| | Ring substituent | Compound B | Fluorescent dye | MALDI-TOF-MS[M + H]$^+$ |
|---|---|---|---|---|
| Example 58 | 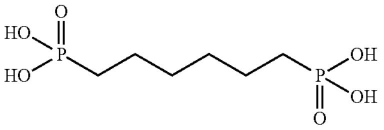 [SMILES: O=P(O)(O)CCCCCCP(=O)(O)O] | C-3 | Fluorescent dye 58 | Theoretical value: 913.24<br>Actually measured value: 913.66 |
| Example 59 | 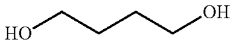 | C-4 | Fluorescent dye 59 | Theoretical value: 797.21<br>Actually measured value: 797.18 |

Example 62

<Manufacturing Method of Fluorescent Dye 62>

1.0 Part of Cy5-NHS ester (Funakoshi Co., Ltd.), 0.5 parts of 3-aminopropanol, and 0.5 parts of triethylamine were dissolved in 50 parts of DMF, and this solution was reacted at room temperature for 12 hours. 50 Parts of water was added to this reaction liquid, a precipitated deposit (solid) was filtered, and, furthermore, the solid was washed with water. The washed solid was dried at 80° C., thereby obtaining 0.70 parts of a fluorescent dye 62 shown in Table 1 (yield: 86.4%). As a result of a mass analysis, a molecular ion peak was detected at m/z=541.18 (theoretical value: 541.36), and it was identified that the fluorescent dye had the structure of the fluorescent dye 62 shown in Table 1.

Example 63

<Manufacturing Method of Fluorescent Dye 63>

1.0 Part of BDPFL, which is a BODIPY-based dye, (manufactured by Tokyo Chemical Industry Co., Ltd.) and 0.3 parts of 3-aminopropanol were dissolved in 50 parts of xylene, and this solution was reacted at 140° C. for 24 hours. After this reaction liquid was cooled to room temperature, xylene was removed from the reaction liquid using an evaporator, and 50 parts of a petroleum ether was added thereto. Next, a precipitated insoluble matter was removed by suction filtration, and then the petroleum ether was removed from the reaction liquid using an evaporator, thereby obtaining a solid. This solid was dried at 80° C., thereby obtaining 0.64 parts of a fluorescent dye 63 shown in Table 1 (yield: 70.6%). As a result of a mass analysis, a molecular ion peak was detected at m/z=350.01 (theoretical value: 350.18), and it was identified that the fluorescent dye had the structure of the fluorescent dye 63 shown in Table 1.

Comparative Example 1

As a comparative compound 1, the compound A-1 was used.

Comparative Example 2

As a comparative compound 2, the compound A-9 was used.

In Comparative Examples 3 to 11 to be described below, comparative compounds 3 to 11 shown in Table 17 were manufactured.

TABLE 17

| | |
|---|---|
| 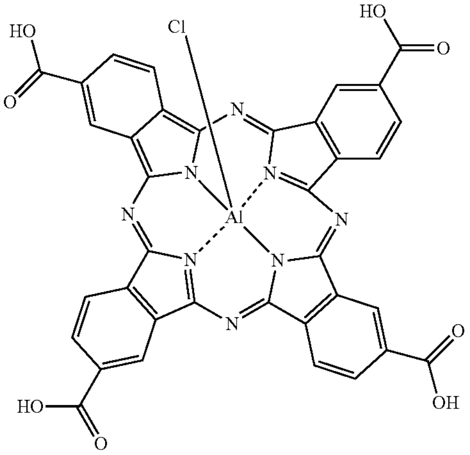 | Comparative compound 3 |
| 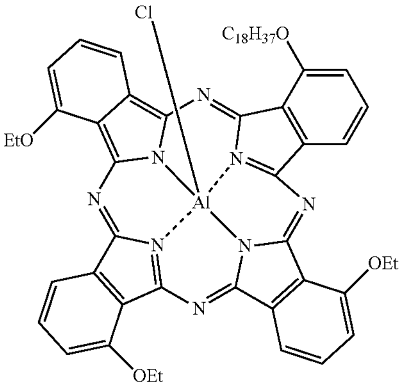 | Comparative compound 4 |

TABLE 17-continued
Comparative compound 5
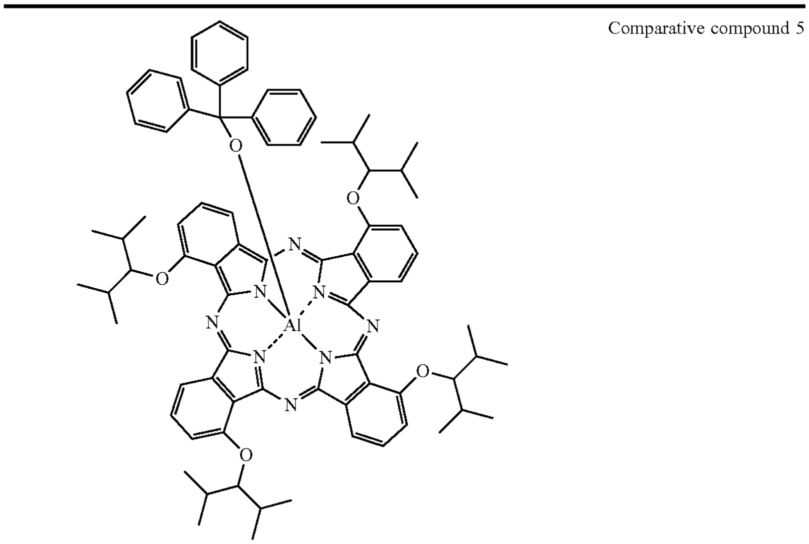
Comparative compound 6
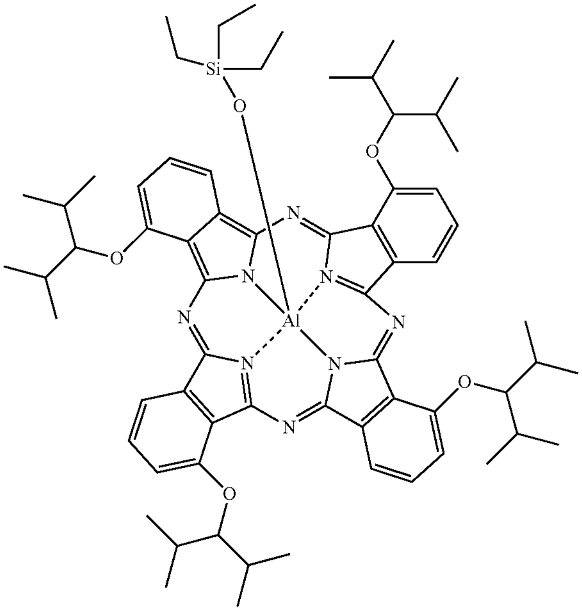
Comparative compound 7
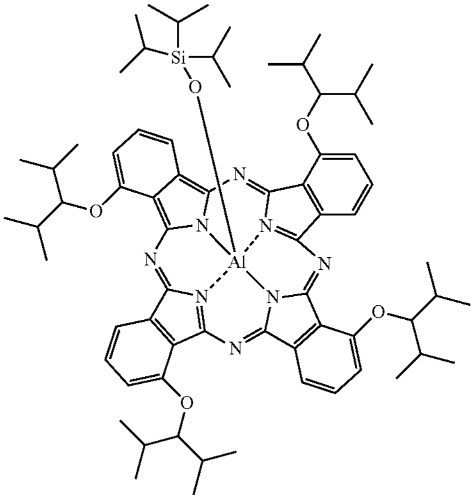

TABLE 17-continued
Comparative compound 8
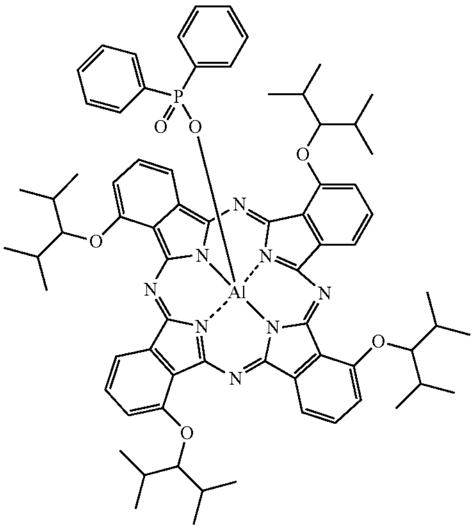
Comparative compound 9
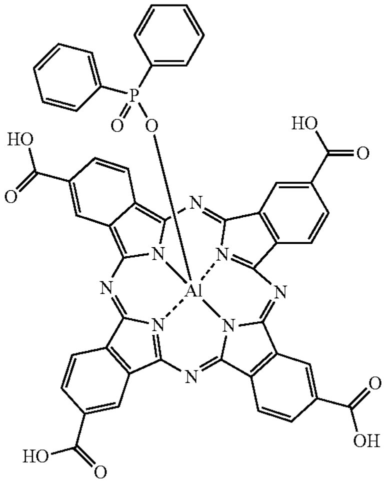
Comparative compound 10
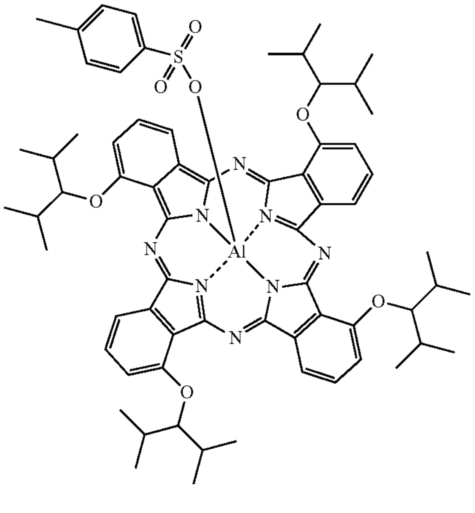

TABLE 17-continued

| | |
|---|---|
| 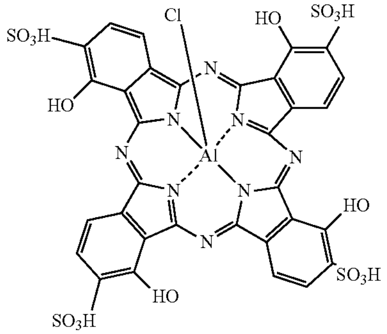 | Comparative compound 11 |

Comparative Example 3

<Manufacturing Method of Comparative Compound 3>

7.0 Parts of aluminum chloride, 39 parts of urea, 0.2 parts of ammonium molybdate, and 25 parts of trimellitic anhydride were dissolved in 40 parts of N-methyl-2-pyrrolidone (NMP), and this solution was stirred at 139° C. for nine hours. This reaction liquid is cooled to room temperature, and then 100 parts of water was added thereto. Next, a precipitated solid was filtered, and the solid was washed with 50 parts of water. The washed solid was dried at 80° C., thereby obtaining 14.5 parts of a comparative compound 3 shown in Table 17 (yield: 59.3%). As a result of a mass analysis, a molecular ion peak was detected at m/z=751.84 (theoretical value: 751.00), and it was identified that the comparative compound had the structure of the comparative compound 3 shown in Table 17.

Comparative Example 4

<Manufacturing Method of Comparative Compound 4>

An ammonia gas was introduced into a solution of 30 parts of quinoline and 0.7 parts of anhydrous aluminum chloride, furthermore, 1.5 parts of 3-ethoxyphthalonitrile and 2.1 parts of 4-octadecyloxyphthalonitrile were added thereto, and this solution was reacted at 180° C. for seven hours. This reaction liquid is cooled to room temperature, and then 200 parts of methanol and 200 parts of a 10% hydrochloric acid aqueous solution were added thereto. Next, a precipitated solid was filtered, and the solid was washed with 200 parts of water. The washed solid (crude product) was purified using medium-pressure liquid chromatography (Smart Flash AKROS manufactured by Yamazen Corporation). The obtained purified product was dried at 80° C., thereby obtaining 0.36 parts of a comparative compound 4 shown in Table 17 (yield: 12.6%). As a result of a mass analysis, a molecular ion peak was detected at m/z=976.44 (theoretical value: 975.61), and it was identified that the comparative compound had the structure of the comparative compound 4 shown in Table 17.

Comparative Example 5

<Manufacturing Method of Comparative Compound 5>

1.0 Part of the compound A-9 and 0.35 parts of triphenylsilanol were dissolved in 20 parts of dimethyl sulfoxide, and this solution was reacted at 80° C. for eight hours. This reaction liquid is cooled to room temperature, and then 50 parts of water and 10 parts of common salt were added thereto. Next, a precipitated solid was filtered, and the solid was washed with 50 parts of water. The washed solid was dried at 80° C., thereby obtaining 1.00 part of a comparative compound 5 shown in Table 17 (yield: [8]0.5%). As a result of a mass analysis, a molecular ion peak was detected at m/z=1282.53 (theoretical value: 1271.67), and it was identified that the comparative compound had the structure of the comparative compound 5 shown in Table 17.

Comparative Examples 6 to 9

<Manufacturing Methods of Comparative Compounds 6 to 9>

Comparative compounds 6 to 9 shown in Table 17 were each manufactured in the same manner as in the manufacturing of the comparative compound 5 except that the compound A-9 and triphenylsilanol used in the manufacturing method of the comparative compound 5 were changed to a halogen and an acidic compound shown in Table 18. The halogen and the acidic compound were used in the same molar quantities as those of the compound A-9 and triphenylsilanol in the manufacturing of the comparative compound 5, respectively. The structures of the obtained comparative compounds 6 to 9 were identified by mass analyses, and it was confirmed that the fluorescent dyes had a structure shown in Table 17. Table 19 shows the analysis results of mass spectra.

TABLE 18

| | Halogens | Acidic compound | Comparative compound |
|---|---|---|---|
| Comparative example 5 | Compound A-9 | 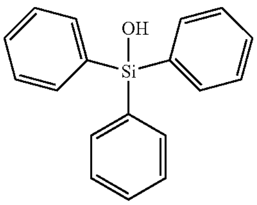 [SMILES: O[Si](c1ccccc1)(c1ccccc1)c1ccccc1] | Comparative compound 5 |
| Comparative example 6 | Compound A-9 | 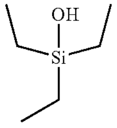 | Comparative compound 6 |
| Comparative example 7 | Compound A-9 | 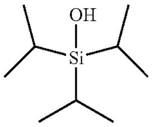 | Comparative compound 7 |
| Comparative example 8 | Compound A-9 | 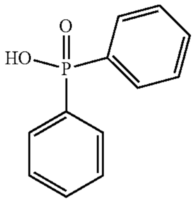 [SMILES: O=P(O)(c1ccccc1)c1ccccc1] | Comparative compound 8 |
| Comparative example 9 | Comparative compound 3 | 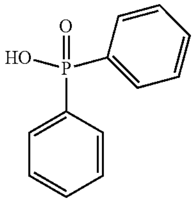 [SMILES: O=P(O)(c1ccccc1)c1ccccc1] | Comparative compound 9 |

Comparative Example 10

<Manufacturing Method of Comparative Compound 10>

2.0 Parts of the compound A-9 and 1.0 part of para-toluenesulfonic acid were dissolved in 50 parts of dimethyl sulfoxide, furthermore, 0.3 parts of 1,8-diazabicyclo[5.4.0]-7-undecene was added to this solution, and these were reacted at 90° C. for five hours. This reaction liquid is cooled to room temperature, and then 100 parts of water was added thereto. Next, a precipitated solid was filtered, and the solid was washed with 50 parts of water. The washed solid was dried at 80° C., thereby obtaining 1.35 parts of a comparative compound 10 shown in Table 17 (yield: 60.0%). As a result of a mass analysis, a molecular ion peak was detected at m/z=933.67 (theoretical value: 932.74), and it was identified that the comparative compound had the structure of the comparative compound 10 shown in Table 17.

Comparative Example 11

<Manufacturing Method of Comparative Compound 11>

One part of the compound A-1 was added to a mixed solution of 9.2 parts of concentrated sulfuric acid and 5.5 parts of 25% fuming sulfuric acid, and this solution was heated and stirred at 50° C. for four hours. After this reaction liquid was cooled, 80 parts of ice was added thereto, and the precipitated deposit (solid) was filtered. Furthermore, the filtered solid was suspended in 50 parts of tetrahydrofuran, and deposition was filtered again. The filtered solid was washed with 50 parts of tetrahydrofuran, and the washed solid was dried, thereby obtaining 0.5 parts of a crude product. The crude product was purified using medium-pressure liquid chromatography (Smart Flash AKROS manufactured by Yamazen Corporation), thereby obtaining 0.2 parts of a comparative compound 11 (yield: 16.0%). As a result of a mass analysis, a molecular ion peak was detected at m/z=939.65 (theoretical value: 940.75), and it was identified that the comparative compound had the structure of the comparative compound 11 shown in Table 17.

The analysis results of the mass spectra of the comparative compounds 3 to 11 manufactured in Comparative Examples 3 to 11 will be shown.

TABLE 19

| | Theoretical value | Measurement value |
|---|---|---|
| Comparative compound 3 | 751.00 | 751.84 |
| Comparative compound 4 | 975.61 | 976.44 |
| Comparative compound 5 | 1271.67 | 1282.53 |
| Comparative compound 6 | 1127.54 | 1128.49 |
| Comparative compound 7 | 1169.62 | 1170.82 |
| Comparative compound 8 | 1231.45 | 1232.37 |
| Comparative compound 9 | 932.74 | 933.67 |
| Comparative compound 10 | 1167.46 | 1168.37 |
| Comparative compound 11 | 940.75 | 939.65 |

Comparative Example 12

As a comparative compound 12, XenoLight DIR (manufactured by Summit Pharmaceuticals International Corporation), which is a cyanine dye, was used. This compound corresponds to a conventional fluorescent labeling agent having a long-chain alkylene group and is accumulated in phospholipids through a hydrophobic interaction.

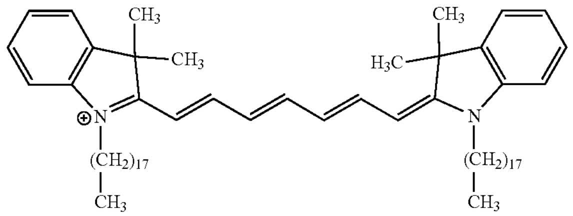

Comparative Example 13

As a comparative compound 13, Rhodamine B (manufactured by Tokyo Chemical Industry Co., Ltd.) was used.

<II> Dye Solution

Example 64

<Preparation of Dye Solution 1>

1.696 mg of the fluorescent dye 1 was dissolved in 10 ml of dimethyl sulfoxide. This solution was filtered using a nylon membrane filter having a pore diameter of 0.2 μm and then diluted 100 times with dimethyl sulfoxide, thereby preparing a dye solution 1 of the fluorescent dye 1.

Examples 65 to 126

<Preparation of Dye Solutions 2 to 63>

Dye solutions 2 to 63 were each prepared in the same manner as in the preparation of the dye solution 1 except that the fluorescent dye 1 and dimethyl sulfoxide used in the preparation of the dye solution 1 were changed to a fluorescent dye and a solvent shown in Table 20. Each fluorescent dye was used in the same molar quantity as that of the fluorescent dye 1, and each solvent was used in the same volume as that of dimethyl sulfoxide.

Comparative Examples 12 to 24

<Preparation of Dye Solutions 64 to 76>

Dye solutions 64 to 76 were each prepared in the same manner as in the preparation of the dye solution 1 except that the fluorescent dye 1 and dimethyl sulfoxide used in the preparation of the dye solution 1 were changed to a fluorescent dye and a solvent shown in Table 20. Each fluorescent dye was used in the same molar quantity as that of the fluorescent dye 1, and each solvent was used in the same volume as that of dimethyl sulfoxide.

TABLE 20-1

| | Dye solution | Fluorescent dye | Solvent |
|---|---|---|---|
| Example 64 | Dye solution 1 | Fluorescent dye 1 | DMSO |
| Example 65 | Dye solution 2 | Fluorescent dye 2 | DMSO |
| Example 66 | Dye solution 3 | Fluorescent dye 3 | DMSO |
| Example 67 | Dye solution 4 | Fluorescent dye 4 | DMSO |
| Example 68 | Dye solution 5 | Fluorescent dye 5 | DMSO |
| Example 69 | Dye solution 6 | Fluorescent dye 6 | DMSO |
| Example 70 | Dye solution 7 | Fluorescent dye 7 | DMSO |
| Example 71 | Dye solution 8 | Fluorescent dye 8 | DMSO |
| Example 72 | Dye solution 9 | Fluorescent dye 9 | DMSO |
| Example 73 | Dye solution 10 | Fluorescent dye 10 | DMSO |
| Example 74 | Dye solution 11 | Fluorescent dye 11 | DMSO |
| Example 75 | Dye solution 12 | Fluorescent dye 12 | DMSO |
| Example 76 | Dye solution 13 | Fluorescent dye 13 | DMSO |
| Example 77 | Dye solution 14 | Fluorescent dye 14 | DMSO |
| Example 78 | Dye solution 15 | Fluorescent dye 15 | DMSO |
| Example 79 | Dye solution 16 | Fluorescent dye 16 | DMSO |
| Example 80 | Dye solution 17 | Fluorescent dye 17 | DMSO |
| Example 81 | Dye solution 18 | Fluorescent dye 18 | DMSO |
| Example 82 | Dye solution 19 | Fluorescent dye 19 | DMSO |
| Example 83 | Dye solution 20 | Fluorescent dye 20 | DMSO |
| Example 84 | Dye solution 21 | Fluorescent dye 21 | DMSO |
| Example 85 | Dye solution 22 | Fluorescent dye 22 | DMSO |
| Example 86 | Dye solution 23 | Fluorescent dye 23 | DMSO |
| Example 87 | Dye solution 24 | Fluorescent dye 24 | DMSO |
| Example 88 | Dye solution 25 | Fluorescent dye 25 | DMSO |
| Example 89 | Dye solution 26 | Fluorescent dye 26 | DMSO |
| Example 90 | Dye solution 27 | Fluorescent dye 27 | DMSO |
| Example 91 | Dye solution 28 | Fluorescent dye 28 | DMSO |
| Example 92 | Dye solution 29 | Fluorescent dye 29 | DMSO |
| Example 93 | Dye solution 30 | Fluorescent dye 30 | DMSO |
| Example 94 | Dye solution 31 | Fluorescent dye 31 | DMSO |
| Example 95 | Dye solution 32 | Fluorescent dye 32 | DMSO |

TABLE 20-2

| | Fluorescent labeling agent | Fluorescent dye | Solvent |
|---|---|---|---|
| Example 96 | Dye solution 33 | Fluorescent dye 33 | DMSO |
| Example 97 | Dye solution 34 | Fluorescent dye 34 | DMSO |
| Example 98 | Dye solution 35 | Fluorescent dye 35 | DMSO |
| Example 99 | Dye solution 36 | Fluorescent dye 36 | DMSO |
| Example 100 | Dye solution 37 | Fluorescent dye 37 | DMSO |
| Example 101 | Dye solution 38 | Fluorescent dye 38 | DMSO |
| Example 102 | Dye solution 39 | Fluorescent dye 39 | DMSO |
| Example 103 | Dye solution 40 | Fluorescent dye 40 | DMSO |
| Example 104 | Dye solution 41 | Fluorescent dye 41 | DMSO |
| Example 105 | Dye solution 42 | Fluorescent dye 42 | DMSO |
| Example 106 | Dye solution 43 | Fluorescent dye 43 | DMSO |
| Example 107 | Dye solution 44 | Fluorescent dye 44 | DMSO |
| Example 108 | Dye solution 45 | Fluorescent dye 45 | DMSO |
| Example 109 | Dye solution 46 | Fluorescent dye 46 | DMSO |
| Example 110 | Dye solution 47 | Fluorescent dye 47 | DMSO |
| Example 111 | Dye solution 48 | Fluorescent dye 48 | DMSO |
| Example 112 | Dye solution 49 | Fluorescent dye 49 | DMSO |
| Example 113 | Dye solution 50 | Fluorescent dye 50 | DMSO |
| Example 114 | Dye solution 51 | Fluorescent dye 51 | DMSO |
| Example 115 | Dye solution 52 | Fluorescent dye 52 | DMSO |
| Example 116 | Dye solution 53 | Fluorescent dye 53 | DMSO |
| Example 117 | Dye solution 54 | Fluorescent dye 54 | DMSO |
| Example 118 | Dye solution 55 | Fluorescent dye 55 | DMSO |
| Example 119 | Dye solution 56 | Fluorescent dye 56 | DMSO |
| Example 120 | Dye solution 57 | Fluorescent dye 57 | DMSO |
| Example 121 | Dye solution 58 | Fluorescent dye 58 | DMSO |
| Example 122 | Dye solution 59 | Fluorescent dye 59 | DMSO |

TABLE 20-2-continued

| | Fluorescent labeling agent | Fluorescent dye | Solvent |
|---|---|---|---|
| Example 123 | Dye solution 60 | Fluorescent dye 60 | DMSO |
| Example 124 | Dye solution 61 | Fluorescent dye 61 | DMSO |
| Example 125 | Dye solution 62 | Fluorescent dye 62 | DMSO |
| Example 126 | Dye solution 63 | Fluorescent dye 63 | DMSO |

TABLE 20-3

| | Fluorescent labeling agent | Fluorescent dye | Solvent |
|---|---|---|---|
| Comparative Example 12 | Dye solution 64 | Fluorescent dye 1 | DMSO |
| Comparative Example 13 | Dye solution 65 | Fluorescent dye 2 | DMSO |
| Comparative Example 14 | Dye solution 66 | Fluorescent dye 3 | DMSO |
| Comparative Example 15 | Dye solution 67 | Fluorescent dye 4 | DMSO |
| Comparative Example 16 | Dye solution 68 | Fluorescent dye 5 | DMSO |
| Comparative Example 17 | Dye solution 69 | Fluorescent dye 6 | DMSO |
| Comparative Example 18 | Dye solution 70 | Fluorescent dye 7 | DMSO |
| Comparative Example 19 | Dye solution 71 | Fluorescent dye 8 | DMSO |
| Comparative Example 20 | Dye solution 72 | Fluorescent dye 9 | DMSO |
| Comparative Example 21 | Dye solution 73 | Fluorescent dye 10 | DMSO |
| Comparative Example 22 | Dye solution 74 | Fluorescent dye 11 | DMSO |
| Comparative Example 23 | Dye solution 75 | Fluorescent dye 12 | DMSO |
| Comparative Example 24 | Dye solution 76 | Fluorescent dye 13 | Water |

<Evaluation of Fluorescence Intensity of Dye Solution>

For each dye solution, the fluorescent spectrum was measured using a fluorometer (manufactured by JASCO Corporation, FP-6500). Furthermore, a fluorescence intensity in a range of fluorescent wavelengths shown in Table 22 was added to the obtained measurement value, thereby obtaining a fluorescence intensity. In addition, as excitation light at this time, a wavelength corresponding to the absorption maximum wavelength of the dye on the longest wavelength side was used.

<III> Fluorescent Labeling Agent

Example 127

<Preparation of Fluorescent Labeling Agent 1>

1.696 mg of the fluorescent dye 1 was dissolved in 10 ml of dimethyl sulfoxide. The solution was filtered with a nylon membrane filter having a pore diameter of 0.2 μm and then diluted 100 times in a RPMI 1640 medium, thereby preparing a fluorescent labeling agent 1 of the fluorescent dye 1.

Examples 128 to 189

<Preparation of Fluorescent Labeling Agents 2 to 63>

Fluorescent labeling agents 2 to 63 were each prepared in the same manner as in the preparation of the fluorescent labeling agent 1 except that the fluorescent dye 1 and dimethyl sulfoxide used in the preparation of the fluorescent labeling agent 1 were changed to a fluorescent dye and a solvent shown in Table 21. Each fluorescent dye was used in the same molar quantity as that of the fluorescent dye 1, and each solvent was used in the same volume as that of dimethyl sulfoxide.

Comparative Examples 25 to 37

<Preparation of Fluorescent Labeling Agents 64 to 76>

Fluorescent labeling agents 64 to 76 were each prepared in the same manner as in the preparation of the fluorescent labeling agent 1 except that the fluorescent dye 1 and dimethyl sulfoxide used in the preparation of the fluorescent labeling agent 1 were changed to a fluorescent dye and a solvent shown in Table 21. Each fluorescent dye was used in the same molar quantity as that of the fluorescent dye 1, and each solvent was used in the same volume as that of dimethyl sulfoxide.

TABLE 21-1

| | Fluorescent labeling agent | Fluorescent dye | Solvent |
|---|---|---|---|
| Example 127 | Dye solution 1 | Fluorescent dye 1 | DMSO |
| Example 128 | Dye solution 2 | Fluorescent dye 2 | DMSO |
| Example 129 | Dye solution 3 | Fluorescent dye 3 | DMSO |
| Example 130 | Dye solution 4 | Fluorescent dye 4 | DMSO |
| Example 131 | Dye solution 5 | Fluorescent dye 5 | DMSO |
| Example 132 | Dye solution 6 | Fluorescent dye 6 | DMSO |
| Example 133 | Dye solution 7 | Fluorescent dye 7 | DMSO |
| Example 134 | Dye solution 8 | Fluorescent dye 8 | DMSO |
| Example 135 | Dye solution 9 | Fluorescent dye 9 | DMSO |
| Example 136 | Dye solution 10 | Fluorescent dye 10 | DMSO |
| Example 137 | Dye solution 11 | Fluorescent dye 11 | DMSO |
| Example 138 | Dye solution 12 | Fluorescent dye 12 | DMSO |
| Example 139 | Dye solution 13 | Fluorescent dye 13 | DMSO |
| Example 140 | Dye solution 14 | Fluorescent dye 14 | DMSO |
| Example 141 | Dye solution 15 | Fluorescent dye 15 | DMSO |
| Example 142 | Dye solution 16 | Fluorescent dye 16 | DMSO |
| Example 143 | Dye solution 17 | Fluorescent dye 17 | DMSO |
| Example 144 | Dye solution 18 | Fluorescent dye 18 | DMSO |
| Example 145 | Dye solution 19 | Fluorescent dye 19 | DMSO |
| Example 146 | Dye solution 20 | Fluorescent dye 20 | DMSO |
| Example 147 | Dye solution 21 | Fluorescent dye 21 | DMSO |
| Example 148 | Dye solution 22 | Fluorescent dye 22 | DMSO |
| Example 149 | Dye solution 23 | Fluorescent dye 23 | DMSO |
| Example 150 | Dye solution 24 | Fluorescent dye 24 | DMSO |
| Example 151 | Dye solution 25 | Fluorescent dye 25 | DMSO |
| Example 152 | Dye solution 26 | Fluorescent dye 26 | DMSO |
| Example 153 | Dye solution 27 | Fluorescent dye 27 | DMSO |
| Example 154 | Dye solution 28 | Fluorescent dye 28 | DMSO |
| Example 155 | Dye solution 29 | Fluorescent dye 29 | DMSO |
| Example 156 | Dye solution 30 | Fluorescent dye 30 | DMSO |
| Example 157 | Dye solution 31 | Fluorescent dye 31 | DMSO |
| Example 158 | Dye solution 32 | Fluorescent dye 32 | DMSO |

TABLE 21-2

| | Fluorescent labeling agent | Fluorescent dye | Solvent |
|---|---|---|---|
| Example 159 | Dye solution 33 | Fluorescent dye 33 | DMSO |
| Example 160 | Dye solution 34 | Fluorescent dye 34 | DMSO |
| Example 161 | Dye solution 35 | Fluorescent dye 35 | DMSO |
| Example 162 | Dye solution 36 | Fluorescent dye 36 | DMSO |
| Example 163 | Dye solution 37 | Fluorescent dye 37 | DMSO |
| Example 164 | Dye solution 38 | Fluorescent dye 38 | DMSO |
| Example 165 | Dye solution 39 | Fluorescent dye 39 | DMSO |
| Example 166 | Dye solution 40 | Fluorescent dye 40 | DMSO |
| Example 167 | Dye solution 41 | Fluorescent dye 41 | DMSO |
| Example 168 | Dye solution 42 | Fluorescent dye 42 | DMSO |
| Example 169 | Dye solution 43 | Fluorescent dye 43 | DMSO |
| Example 170 | Dye solution 44 | Fluorescent dye 44 | DMSO |
| Example 171 | Dye solution 45 | Fluorescent dye 45 | DMSO |
| Example 172 | Dye solution 46 | Fluorescent dye 46 | DMSO |
| Example 173 | Dye solution 47 | Fluorescent dye 47 | DMSO |

TABLE 21-2-continued

| | Fluorescent labeling agent | Fluorescent dye | Solvent |
|---|---|---|---|
| Example 174 | Dye solution 48 | Fluorescent dye 48 | DMSO |
| Example 175 | Dye solution 49 | Fluorescent dye 49 | DMSO |
| Example 176 | Dye solution 50 | Fluorescent dye 50 | DMSO |
| Example 177 | Dye solution 51 | Fluorescent dye 51 | DMSO |
| Example 178 | Dye solution 52 | Fluorescent dye 52 | DMSO |
| Example 179 | Dye solution 53 | Fluorescent dye 53 | DMSO |
| Example 180 | Dye solution 54 | Fluorescent dye 54 | DMSO |
| Example 181 | Dye solution 55 | Fluorescent dye 55 | DMSO |
| Example 182 | Dye solution 56 | Fluorescent dye 56 | DMSO |
| Example 183 | Dye solution 57 | Fluorescent dye 57 | DMSO |
| Example 184 | Dye solution 58 | Fluorescent dye 58 | DMSO |
| Example 185 | Dye solution 59 | Fluorescent dye 59 | DMSO |
| Example 186 | Dye solution 60 | Fluorescent dye 60 | DMSO |
| Example 187 | Dye solution 61 | Fluorescent dye 61 | DMSO |
| Example 188 | Dye solution 62 | Fluorescent dye 62 | DMSO |
| Example 189 | Dye solution 63 | Fluorescent dye 63 | DMSO |

TABLE 21-3

| | Fluorescent labeling agent | Fluorescent dye | Solvent |
|---|---|---|---|
| Comparative Example 25 | Dye solution 64 | Comparative compound 1 | DMSO |
| Comparative Example 26 | Dye solution 65 | Comparative compound 2 | DMSO |
| Comparative Example 27 | Dye solution 66 | Comparative compound 3 | DMSO |
| Comparative Example 28 | Dye solution 67 | Comparative compound 4 | DMSO |
| Comparative Example 29 | Dye solution 68 | Comparative compound 5 | DMSO |
| Comparative Example 30 | Dye solution 69 | Comparative compound 6 | DMSO |
| Comparative Example 31 | Dye solution 70 | Comparative compound 7 | DMSO |
| Comparative Example 32 | Dye solution 71 | Comparative compound 8 | DMSO |
| Comparative Example 33 | Dye solution 72 | Comparative compound 9 | DMSO |
| Comparative Example 34 | Dye solution 73 | Comparative compound 10 | DMSO |
| Comparative Example 35 | Dye solution 74 | Comparative compound 11 | DMSO |
| Comparative Example 36 | Dye solution 75 | Comparative compound 12 | DMSO |
| Comparative Example 37 | Dye solution 76 | Comparative compound 13 | RPMI 1640 medium |

<Evaluation of Cell Toxicity of Fluorescent Labeling Agent>

Human epithelium cancer cells A431 were seeded in a 96-well plate ($1\times10^4$ cells/well). Next, the A431 were cultured for 24 hours using an RPMI 1640 medium to which 10% fetal bovine serum (FBS) and 1% penicillin-streptomycin had been added in an incubator (37° C., 5% $CO_2$-containing Air, humidified environment). As the RPMI 1640 medium, an RPMI-164-Medium manufactured by Sigma-Aldrich Inc. was used.

After cultivation, the medium was removed, the fluorescent labeling agents prepared in Examples 83 to 123 and Comparative Examples 25 to 37 and an RPMI 1640 medium containing 1% dimethyl sulfoxide (DMSO medium solution) were added thereto. These were left to stand in the incubator for one hour and then washed in the RPMI 1640 medium. 10 μL of a cell counting kit-8 (manufactured by Dojindo Laboratories.) was added to each well and left to stand in the incubator (37° C., 5% $CO_2$-containing Air, humidified environment) for one hour. Next, the absorbance at 450 nm was measured using a plate reader (SPARK, manufactured by Tecan Trading AG).

The relative value of the absorbance of each fluorescent labeling agent when the absorbance of the well to which the DMSO medium solution had been added was regarded as one was calculated and evaluated based on the following standards. When the relative value was evaluated as "P", it can be said that the fluorescent labeling agent does not exhibit cell toxicity. At the time of calculating the relative value of the absorbance of the fluorescent labeling agent, a value obtained by subtracting the absorbance before the addition of the cell counting kit-8 (manufactured by Dojindo Laboratories.) from the measured absorbance was used. The evaluation results are shown in Table 22.

(Evaluation Standards)

P (Pass): 0.8 or more

F (Failure): Less than 0.8

<Evaluation of Fluorescence Intensity of Fluorescent Labeling Agent>

Human epithelium cancer cells A431 were seeded in a 96-well plate ($1\times10^4$ cells/well). Next, the A431 were cultured for 24 hours using an RPMI 1640 medium to which 10% fetal bovine serum (FBS) and 1% penicillin-streptomycin had been added in an incubator (37° C., 5% $CO_2$-containing Air, humidified environment).

After cultivation, the medium was removed, and the fluorescent labeling agents prepared in Examples 127 to 167 and Comparative Examples 25 to 37 were added thereto and left to stand in the incubator for one hour. Next, these were washed in the RPMI 1640 medium. The fluorescence intensities were evaluated in fluorescence wavelength ranges shown in Table 22 using the plate reader (SPARK, manufactured by Tecan Trading AG).

FIG. 1 shows the evaluation results of the fluorescence intensities of the fluorescent labeling agents 1, 15, 19, 24, 25, 68, and 75. It was possible to confirm that the fluorescent labeling agents 1, 15, 19, 24, and 25 (examples), which are the embodiment of the present invention, exhibit high fluorescence intensities compared with the fluorescent labeling agents 68 and 75 (comparative examples) prepared using the comparative compounds.

<Evaluation of Property of Fluorescent Dye being Accumulated in Phospholipids>

The property of each dye being accumulated in phospholipids was calculated from the fluorescence intensity integral value obtained from the fluorescent spectrum of the dye solution and the fluorescence intensity obtained from the fluorescence intensity of the fluorescent labeling agent using an expression (1). The relative value of the property of each fluorescent labeling agent being accumulated in phospholipids when the property of the comparative compound 12 being accumulated in phospholipids was regarded as one was calculated and evaluated based on the following standards. In a case where the relative value is evaluated as 3 or more, it can be said that each fluorescent dye has a favorable property of being accumulated in phospholipids.

(Evaluation Standards)

4: The property of being accumulated in phospholipids is 4 or more.

3: The property of being accumulated in phospholipids is 2 or more and less than 4.

2: The property of being accumulated in phospholipids is 1 or more and less than 2.

1: The property of being accumulated in phospholipids is less than 1.

Property of being accumulated in phospholipids=fluorescence intensity of fluorescent labeling agent/fluorescence intensity of dye solution (1)

The evaluation results of the property of being accumulated in phospholipids are shown in Table 22.

It was possible to confirm that the fluorescent labeling agents (examples), which are the embodiment of the present invention, exhibit an excellent property of being accumulated in phospholipids compared with the fluorescent labeling agents (comparative examples) prepared using the comparative compounds.

<Evaluation of Visibility of Cell>

Human epithelium cancer cells A431 were seeded in a 96-well plate ($1\times10^4$ cells/well). The A431 were cultured for 24 hours using an RPMI 1640 medium to which 10% fetal bovine serum (FBS) and 1% penicillin-streptomycin had been added in an incubator (37° C., 5% $CO_2$-containing Air, humidified environment).

After cultivation, the medium was removed, and the fluorescent labeling agents prepared in Examples 127 to 189 and Comparative Examples 25 to 37 were added thereto and left to stand in the incubator for one hour. Next, these were washed in the RPMI 1640 medium. The dark field images and fluorescent images of the cells were observed using a fluorescent microscope (manufactured by Keyence Corporation, BZ-X800) equipped with an excitation filter for an appropriate wavelength and a fluorescent filter and evaluated based on the following standards. The evaluation results are shown in Table 22.

(Evaluation Standards)

P (Pass): Clear

F (Failure): Unclear

TABLE 22-1

| | | | | | Evaluation | | |
|---|---|---|---|---|---|---|---|
| | Fluorescent dye | Dye solution | Fluorescent labeling agent | Fluorescent wavelength (nm) | Cell toxicity | Property of being accumulated in phospholipids | Cell visibility |
| Example 127 | Fluorescent dye 1 | Dye solution 1 | Fluorescent labeling agent 1 | 780-800 | P | 4 | P |
| Example 128 | Fluorescent dye 2 | Dye solution 2 | Fluorescent labeling agent 2 | 780-800 | P | 4 | P |
| Example 129 | Fluorescent dye 3 | Dye solution 3 | Fluorescent labeling agent 3 | 780-800 | P | 4 | P |
| Example 130 | Fluorescent dye 4 | Dye solution 4 | Fluorescent labeling agent 4 | 780-800 | P | 4 | P |
| Example 131 | Fluorescent dye 5 | Dye solution 5 | Fluorescent labeling agent 5 | 780-800 | P | 3 | P |
| Example 132 | Fluorescent dye 6 | Dye solution 6 | Fluorescent labeling agent 6 | 780-800 | P | 4 | P |
| Example 133 | Fluorescent dye 7 | Dye solution 7 | Fluorescent labeling agent 7 | 780-800 | P | 4 | P |
| Example 134 | Fluorescent dye 8 | Dye solution 8 | Fluorescent labeling agent 8 | 780-800 | P | 4 | P |
| Example 135 | Fluorescent dye 9 | Dye solution 9 | Fluorescent labeling agent 9 | 780-800 | P | 4 | P |
| Example 136 | Fluorescent dye 10 | Dye solution 10 | Fluorescent labeling agent 10 | 780-800 | P | 4 | P |
| Example 137 | Fluorescent dye 11 | Dye solution 11 | Fluorescent labeling agent 11 | 780-800 | P | 4 | P |
| Example 138 | Fluorescent dye 12 | Dye solution 12 | Fluorescent labeling agent 12 | 780-800 | P | 4 | P |
| Example 139 | Fluorescent dye 13 | Dye solution 13 | Fluorescent labeling agent 13 | 780-800 | P | 4 | P |
| Example 140 | Fluorescent dye 14 | Dye solution 14 | Fluorescent labeling agent 14 | 780-800 | P | 4 | P |
| Example 141 | Fluorescent dye 15 | Dye solution 15 | Fluorescent labeling agent 15 | 780-800 | P | 4 | P |
| Example 142 | Fluorescent dye 16 | Dye solution 16 | Fluorescent labeling agent 16 | 780-800 | P | 4 | P |
| Example 143 | Fluorescent dye 17 | Dye solution 17 | Fluorescent labeling agent 17 | 780-800 | P | 4 | P |
| Example 144 | Fluorescent dye 18 | Dye solution 18 | Fluorescent labeling agent 18 | 780-800 | P | 4 | P |
| Example 145 | Fluorescent dye 19 | Dye solution 19 | Fluorescent labeling agent 19 | 780-800 | P | 4 | P |
| Example 146 | Fluorescent dye 20 | Dye solution 20 | Fluorescent labeling agent 20 | 780-800 | P | 4 | P |
| Example 147 | Fluorescent dye 21 | Dye solution 21 | Fluorescent labeling agent 21 | 780-800 | P | 4 | P |
| Example 148 | Fluorescent dye 22 | Dye solution 22 | Fluorescent labeling agent 22 | 780-800 | P | 4 | P |
| Example 149 | Fluorescent dye 23 | Dye solution 23 | Fluorescent labeling agent 23 | 780-800 | P | 3 | P |
| Example 150 | Fluorescent dye 24 | Dye solution 24 | Fluorescent labeling agent 24 | 780-800 | P | 4 | P |
| Example 151 | Fluorescent dye 25 | Dye solution 25 | Fluorescent labeling agent 25 | 780-800 | P | 4 | P |
| Example 152 | Fluorescent dye 26 | Dye solution 26 | Fluorescent labeling agent 26 | 780-800 | P | 4 | P |
| Example 153 | Fluorescent dye 27 | Dye solution 27 | Fluorescent labeling agent 27 | 780-800 | P | 4 | P |

TABLE 22-1-continued

| | Fluorescent dye | Dye solution | Fluorescent labeling agent | Fluorescent wavelength (nm) | Evaluation Cell toxicity | Property of being accumulated in phospholipids | Cell visibility |
|---|---|---|---|---|---|---|---|
| Example 154 | Fluorescent dye 28 | Dye solution 28 | Fluorescent labeling agent 28 | 780-800 | P | 4 | P |
| Example 155 | Fluorescent dye 29 | Dye solution 29 | Fluorescent labeling agent 29 | 780-800 | P | 4 | P |
| Example 156 | Fluorescent dye 30 | Dye solution 30 | Fluorescent labeling agent 30 | 780-800 | P | 4 | P |
| Example 157 | Fluorescent dye 31 | Dye solution 31 | Fluorescent labeling agent 31 | 780-800 | P | 4 | P |
| Example 158 | Fluorescent dye 32 | Dye solution 32 | Fluorescent labeling agent 32 | 780-800 | P | 4 | P |

TABLE 22-2

| | Fluorescent dye | Dye solution | Fluorescent labeling agent | Fluorescent wavelength (nm) | Evaluation Cell toxicity | Property of being accumulated in phospholipids | Cell visibility |
|---|---|---|---|---|---|---|---|
| Example 160 | Fluorescent dye 34 | Dye solution 34 | Fluorescent labeling agent 34 | 780-800 | P | 4 | P |
| Example 161 | Fluorescent dye 35 | Dye solution 35 | Fluorescent labeling agent 35 | 780-800 | P | 4 | P |
| Example 162 | Fluorescent dye 36 | Dye solution 36 | Fluorescent labeling agent 36 | 780-800 | P | 4 | P |
| Example 163 | Fluorescent dye 37 | Dye solution 37 | Fluorescent labeling agent 37 | 780-800 | P | 4 | P |
| Example 164 | Fluorescent dye 38 | Dye solution 38 | Fluorescent labeling agent 38 | 630-650 | P | 4 | P |
| Example 165 | Fluorescent dye 39 | Dye solution 39 | Fluorescent labeling agent 39 | 560-570 | P | 4 | P |
| Example 166 | Fluorescent dye 40 | Dye solution 40 | Fluorescent labeling agent 40 | 630-650 | P | 4 | P |
| Example 167 | Fluorescent dye 41 | Dye solution 41 | Fluorescent labeling agent 41 | 560-570 | P | 4 | P |
| Example 168 | Fluorescent dye 42 | Dye solution 42 | Fluorescent labeling agent 42 | 780-800 | P | 4 | P |
| Example 169 | Fluorescent dye 43 | Dye solution 43 | Fluorescent labeling agent 43 | 780-800 | P | 4 | P |
| Example 170 | Fluorescent dye 44 | Dye solution 44 | Fluorescent labeling agent 44 | 780-800 | P | 4 | P |
| Example 171 | Fluorescent dye 45 | Dye solution 45 | Fluorescent labeling agent 45 | 780-800 | P | 4 | P |
| Example 172 | Fluorescent dye 46 | Dye solution 46 | Fluorescent labeling agent 46 | 780-800 | P | 4 | P |
| Example 173 | Fluorescent dye 47 | Dye solution 47 | Fluorescent labeling agent 47 | 780-800 | P | 4 | P |
| Example 174 | Fluorescent dye 48 | Dye solution 48 | Fluorescent labeling agent 48 | 780-800 | P | 4 | P |
| Example 175 | Fluorescent dye 49 | Dye solution 49 | Fluorescent labeling agent 49 | 780-800 | P | 4 | P |
| Example 176 | Fluorescent dye 50 | Dye solution 50 | Fluorescent labeling agent 50 | 780-800 | P | 4 | P |
| Example 177 | Fluorescent dye 51 | Dye solution 51 | Fluorescent labeling agent 51 | 780-800 | P | 4 | P |
| Example 178 | Fluorescent dye 52 | Dye solution 52 | Fluorescent labeling agent 52 | 780-800 | P | 4 | P |
| Example 179 | Fluorescent dye 53 | Dye solution 53 | Fluorescent labeling agent 53 | 780-800 | P | 4 | P |
| Example 180 | Fluorescent dye 54 | Dye solution 54 | Fluorescent labeling agent 54 | 780-800 | P | 4 | P |
| Example 181 | Fluorescent dye 55 | Dye solution 55 | Fluorescent labeling agent 55 | 780-800 | P | 4 | P |
| Example 182 | Fluorescent dye 56 | Dye solution 56 | Fluorescent labeling agent 56 | 780-800 | P | 4 | P |
| Example 183 | Fluorescent dye 57 | Dye solution 57 | Fluorescent labeling agent 57 | 780-800 | P | 4 | P |
| Example 184 | Fluorescent dye 58 | Dye solution 58 | Fluorescent labeling agent 58 | 780-800 | P | 4 | P |
| Example 185 | Fluorescent dye 59 | Dye solution 59 | Fluorescent labeling agent 59 | 780-800 | P | 4 | P |

TABLE 22-2-continued

| | Fluorescent dye | Dye solution | Fluorescent labeling agent | Fluorescent wavelength (nm) | Evaluation Cell toxicity | Property of being accumulated in phospholipids | Cell visibility |
|---|---|---|---|---|---|---|---|
| Example 186 | Fluorescent dye 60 | Dye solution 60 | Fluorescent labeling agent 60 | 630-650 | P | 4 | P |
| Example 187 | Fluorescent dye 61 | Dye solution 61 | Fluorescent labeling agent 61 | 630-650 | P | 4 | P |
| Example 188 | Fluorescent dye 62 | Dye solution 62 | Fluorescent labeling agent 62 | 780-800 | P | 4 | P |
| Example 189 | Fluorescent dye 63 | Dye solution 63 | Fluorescent labeling agent 63 | 560-570 | P | 4 | P |

TABLE 22-3

| | Fluorescent dye | Dye solution | Fluorescent labeling agent | Fluorescent wavelength (nm) | Evaluation Cell toxicity | Property of being accumulated in phospholipids | Cell visibility |
|---|---|---|---|---|---|---|---|
| Comparative Example 26 | Comparative compound 2 | Dye solution 65 | Fluorescent labeling agent 43 | 780-800 | P | 1 | F |
| Comparative Example 27 | Fluorescent dye 3 | Dye solution 66 | Fluorescent labeling agent 44 | 780-800 | P | 1 | F |
| Comparative Example 28 | Fluorescent dye 4 | Dye solution 67 | Fluorescent labeling agent 45 | 780-800 | P | 1 | F |
| Comparative Example 29 | Fluorescent dye 5 | Dye solution 68 | Fluorescent labeling agent 46 | 780-800 | P | 1 | F |
| Comparative Example 30 | Fluorescent dye 6 | Dye solution 69 | Fluorescent labeling agent 47 | 780-800 | P | 1 | F |
| Comparative Example 31 | Fluorescent dye 7 | Dye solution 70 | Fluorescent labeling agent 48 | 780-800 | P | 1 | F |
| Comparative Example 32 | Fluorescent dye 8 | Dye solution 71 | Fluorescent labeling agent 49 | 780-800 | P | 1 | F |
| Comparative Example 33 | Fluorescent dye 9 | Dye solution 72 | Fluorescent labeling agent 50 | 780-800 | P | 1 | F |
| Comparative Example 34 | Fluorescent dye 10 | Dye solution 73 | Fluorescent labeling agent 51 | 780-800 | P | 1 | F |
| Comparative Example 35 | Fluorescent dye 11 | Dye solution 74 | Fluorescent labeling agent 52 | 780-800 | P | 1 | F |
| Comparative Example 36 | Fluorescent dye 12 | Dye solution 75 | Fluorescent labeling agent 53 | 780-800 | P | 1 | F |
| Comparative Example 37 | Fluorescent dye 13 | Dye solution 76 | Fluorescent labeling agent 54 | 630-650 | P | 1 | F |

The evaluation results of the visibility of the cells labeled with the fluorescent labeling agents 1, 15, 19, 24, 25, 68, and 75 are sequentially shown in FIGS. 2 to 8 (magnification: 10 times, optical uptake time: 1 second).

Figure 9:
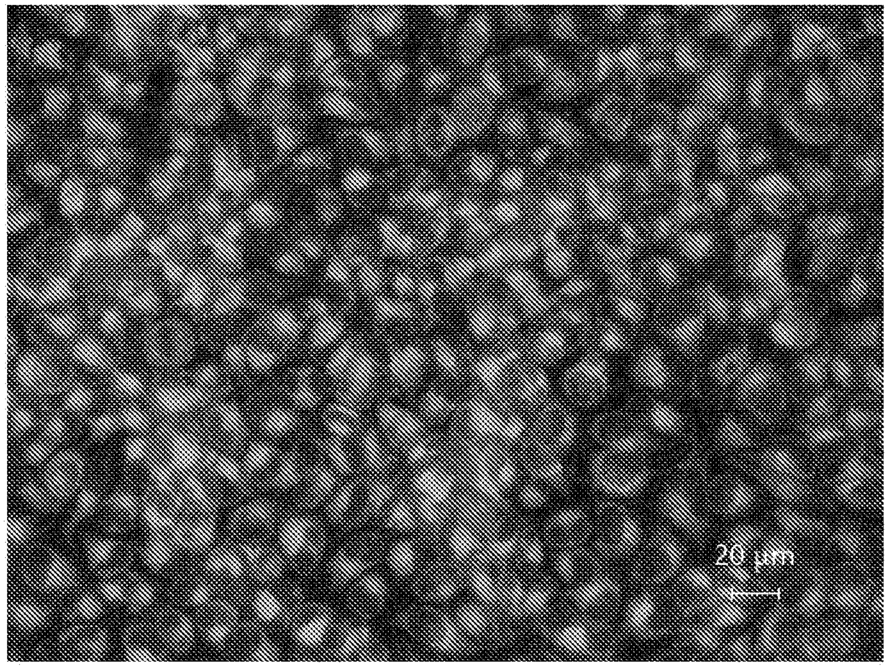
FIG. 9 is a fluorescence micrograph of a cell labeled with the fluorescent labeling agent 42.
Figure 10:
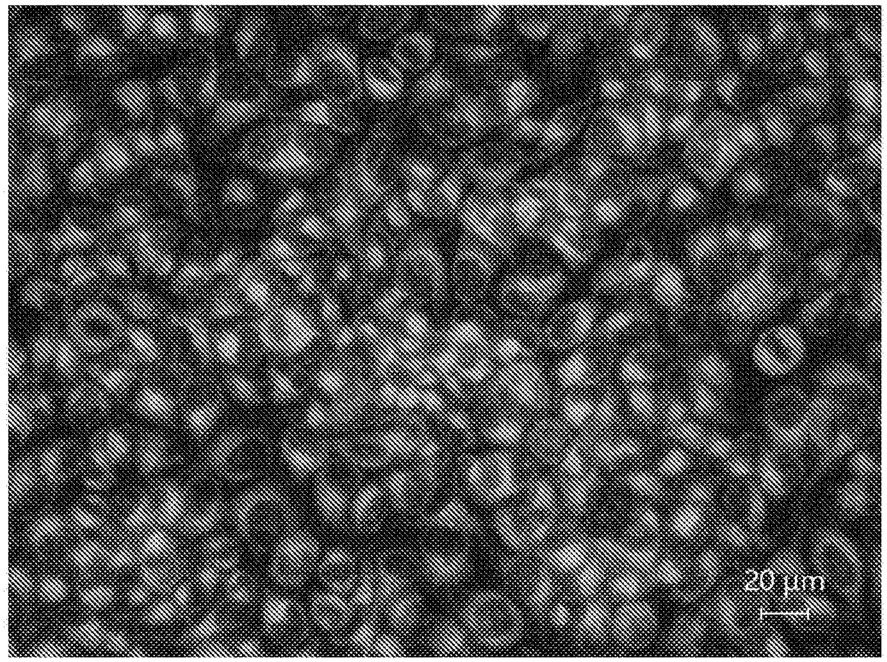
FIG. 10 is a fluorescence micrograph of a cell labeled with the fluorescent labeling agent 53.

The evaluation results of the visibility of the cells labeled with the fluorescent labeling agents 42 and 53 are sequentially shown in FIGS. 9 to 10 (magnification: 40 times, optical uptake time: 1 second).

Figure 7:
FIG. 7 is a fluorescence micrograph of a cell labeled with the fluorescent labeling agent 68.
Figure 8:
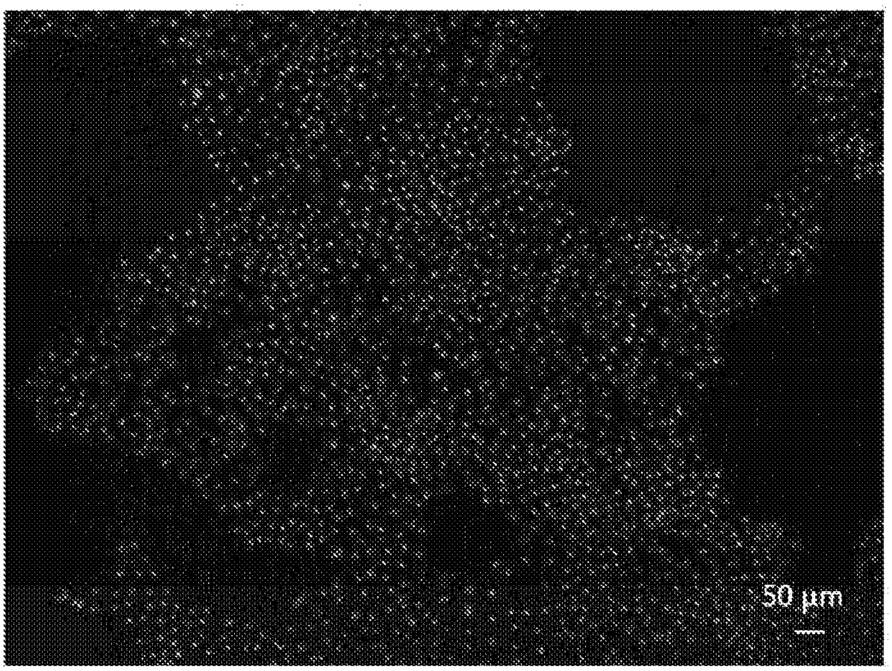
FIG. 8 is a fluorescence micrograph of a cell labeled with the fluorescent labeling agent 75.

As is clear from the comparison between FIGS. 7 and 8 corresponding to the comparative examples and FIGS. 2 to 6, 9, and 10 corresponding to the examples, it was observed that, according to the fluorescent labeling agent of the embodiment of the present invention, higher fluorescence intensities were exhibited due to specific substituents. As described above, it is found that the fluorescent labeling agent of the embodiment of the present invention (examples) is excellent in terms of the property of being accumulated in cells compared with the comparative compounds and thereby enables the obtainment of superior visibility. From what has been described above, it has been clarified that the fluorescent labeling agent according to the embodiment of the present invention has excellent characteristics as a fluorescent labeling agent.

The invention claimed is:

1. A fluorescent labeling agent comprising:

a fluorescent dye containing a phthalocyanine dye represented by the following general formula (2), General Formula (2)

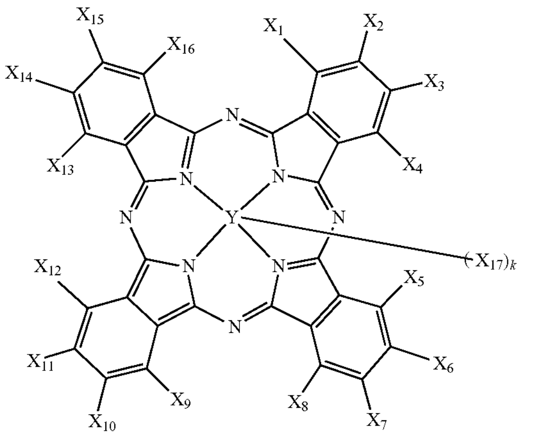

here, $X_1$-$X_{16}$ each independently represent —Z—$R_1$—$R_2$—$R_3$, a hydrogen atom, a substituted or unsubstituted alkyl group, a substituted or unsubstituted aryl group, a substituted or unsubstituted cycloalkyl group, a substituted or unsubstituted alkenyl group, a substituted or unsubstituted heterocyclic group, -AB, —$SO_3M_5$, or —$COOM_6$, in the -AB, A represents a Group 16 element, B represents a hydrogen atom, a substituted or unsubstituted alkyl group, a substituted or unsubstituted aryl group, a substituted or unsubstituted cycloalkyl group, or a substituted or unsubstituted heterocyclic group, the $M_5$ and $M_6$ each independently represent a monovalent cation, or in the $X_1$-$X_{16}$, adjacent substituents may be linked to each other to form a ring, $X_{17}$ represents —Z—$R_1$—$R_2$—$R_3$, a substituted or unsubstituted alkoxy group, a substituted or unsubstituted aryloxy group, —OP(═O)$X_{18}X_{19}$, —OC(═O)$X_{20}$, —OS(═O)$_2X_{21}$, or —OSi$X_{22}X_{23}X_{24}$, the $X_{18}$ and $X_{19}$ each independently represent a hydrogen atom, a hydroxyl group, a substituted or unsubstituted alkyl group, a substituted or unsubstituted aryl group, a substituted or unsubstituted alkoxy group, a substituted or unsubstituted aryloxy group, or a substituted or unsubstituted heterocyclic group, the $X_{20}$ represents a hydrogen atom, a substituted or unsubstituted alkyl group, a substituted or unsubstituted aryl group, or a substituted or unsubstituted heterocyclic group, the $X_{21}$ represents a hydroxyl group, a substituted or unsubstituted alkyl group, a substituted or unsubstituted aryl group, or a substituted or unsubstituted heterocyclic group, the $X_{22}$-$X_{24}$ each independently represent a substituted or unsubstituted alkyl group, a substituted or unsubstituted aryl group, or a substituted or unsubstituted heterocyclic group, Y represents a trivalent to pentavalent metal atom, and k is an integer, in a case where Y is a trivalent metal atom, k is 1, and, in a case where Y is a tetravalent or pentavalent metal atom, k is 2, here, at least one of $X_1$-$X_{17}$ is —Z—$R_1$—$R_2$—$R_3$, Z represents a direct bond, a substituted or unsubstituted alkylene group, or a substituted or unsubstituted arylene group, $R_1$ represents —OP(═O)$R_4$—, —OC(═O)—, —OS(═O)$_2$—, —C(═O)—, or —C(═O)NH—, $R_2$ represents a group selected from the group consisting of unsubstituted alkylene groups, substituted or unsubstituted arylene groups, and substituted or unsubstituted heterocyclic groups, or represents a group provided by combining these groups, $R_3$ represents —$COOM_1$, —$NR_7R_8$, —$OM_2$, or —P(═O)($OM_3$)$OM_4$, the $R_4$ represents a hydrogen atom, a hydroxyl group, a substituted or unsubstituted alkyl group, a substituted or unsubstituted aryl group, a substituted or unsubstituted alkoxy group, a substituted or unsubstituted aryloxy group, or a substituted or unsubstituted heterocyclic group, the $R_7$-$R_8$ each independently represent a hydrogen atom, a substituted or unsubstituted alkyl group, or a substituted or unsubstituted aryl group, and the $M_1$, $M_2$, $M_3$, and $M_4$ each independently represent a hydrogen atom or a monovalent cation.

2. The fluorescent labeling agent according to claim 1 that is a phospholipid accumulation-type fluorescent labeling agent.

3. The fluorescent labeling agent according to claim 1, wherein $X_{17}$ in the general formula (2) is —Z—$R_1$—$R_2$—$R_3$.

4. A compound represented by the following general formula (3),

General Formula (3)

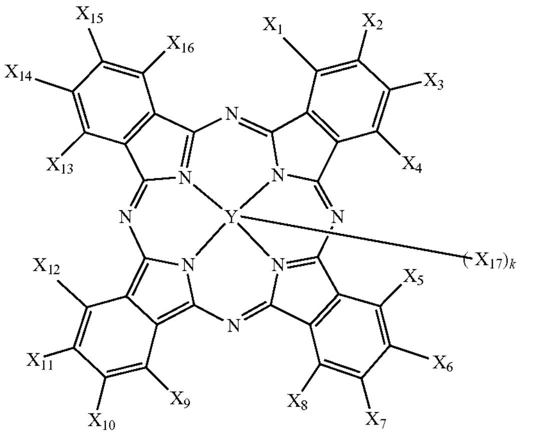

here, $X_1$-$X_{16}$ each independently represent —Z—$R_1$—$R_2$—$R_3$, a hydrogen atom, a substituted or unsubstituted alkyl group, a substituted or unsubstituted aryl group, a substituted or unsubstituted cycloalkyl group, a substituted or unsubstituted alkenyl group, a substituted or unsubstituted heterocyclic group, -AB, —$SO_3M_5$, or —$COOM_6$, in the -AB, A represents a Group 16 element, B represents a hydrogen atom, a substituted or unsubstituted alkyl group, a substituted or unsubstituted aryl group, a substituted or unsubstituted cycloalkyl group, or a substituted or unsubstituted heterocyclic group, the $M_5$ and $M_6$ each independently represent a monovalent cation, or in the $X_1$-$X_{16}$, adjacent substituents may be linked to each other to form a ring, $X_{17}$ represents —Z—$R_1$—$R_2$—$R_3$, a substituted or unsubstituted alkoxy group, a substituted or unsubstituted aryloxy group, —OP(═O)$X_{18}X_{19}$, —OC(═O)$X_2$O, —OS(═O)$_2X_{21}$, or —OSi$X_{22}X_{23}X_{24}$, the $X_{18}$ and $X_{19}$ each independently represent a hydrogen atom, a hydroxyl group, a substituted or unsubstituted alkyl group, a substituted or unsubstituted aryl group, a substituted or unsubstituted alkoxy group, a substituted or unsubstituted aryloxy group, or a substituted or unsubstituted heterocyclic group, the $X_{20}$ represents a hydrogen atom, a substituted or unsubstituted alkyl group, a substituted or unsubstituted aryl group, or a substituted or unsubstituted heterocyclic group, the $X_{21}$ represents a hydroxyl group, a substituted or unsubstituted alkyl group, a substituted or unsubstituted aryl group, or a substituted or unsubstituted heterocyclic group, the $X_{22}$-$X_{24}$ each independently represent a substituted or unsubstituted alkyl group, a substituted or unsubstituted aryl group, or a substituted or unsubstituted heterocyclic group, Y represents a trivalent to pentavalent metal atom, and k is an integer, in a case where Y is a trivalent metal atom, k is 1, and, in a case where Y is a tetravalent or pentavalent metal atom, k is 2, here, at least one of $X_1$-$X_{17}$ is —Z—$R_1$—$R_2$—$R_3$, here, Z represents a direct bond, a substituted or unsubstituted alkylene group, or a substituted or unsubstituted arylene group, $R_1$ represents —OP(═O)$R_4$—, —OC(═O)—, —OS(═O)$_2$—, —C(═O)—, or —C(═O)NH—, $R_2$ represents a group selected from the group consisting of unsubstituted alkylene groups, substituted or unsubstituted arylene groups, and substituted or unsubstituted heterocyclic groups, or represents a group provided by combining these groups, $R_3$ represents —COO$M_1$, —N$R_7R_8$, —O$M_2$, or P(═O)(O$M_3$)O$M_4$, the $R_4$ represents a hydrogen atom, a hydroxyl group, a substituted or unsubstituted alkyl group, a substituted or unsubstituted aryl group, a substituted or unsubstituted alkoxy group, a substituted or unsubstituted aryloxy group, or a substituted or unsubstituted heterocyclic group, the $R_7$-$R_8$ each independently represent a hydrogen atom, a substituted or unsubstituted alkyl group, or a substituted or unsubstituted aryl group, and the $M_1$, $M_2$, $M_3$, and $M_4$ each independently represent a hydrogen atom or a monovalent cation.

5. The fluorescent labeling agent of claim 1, wherein in General Formula (2), $X_{17}$ represents —Z—$R_1$—$R_2$—$R_3$, Z represents a direct bond, $R_1$ represents —OP(═O)$R_4$—, $R_3$ represents —COO$M_1$, and the $M_1$ represents a hydrogen atom or a monovalent cation.

* * * * *